United States Patent
Brodney et al.

(10) Patent No.: US 10,028,962 B2
(45) Date of Patent: *Jul. 24, 2018

(54) 2-AMINO-6-METHY1-4,4A,5,6-TETRAHYDROPYRANO[3,4-D][1,3]THIAZIN-8A(8H)-YL-1,3-THIAZOL-4-YL AMIDES

(71) Applicant: Pfizer Inc., New York, NY (US)

(72) Inventors: Michael Aaron Brodney, Newton, MA (US); Elizabeth Mary Beck, Oxford (GB); Christopher Ryan Butler, Canton, MA (US); Lei Zhang, Auburndale, MA (US); Brian Thomas O'Neill, Haddam, CT (US); Gabriela Barreiro, São Paulo (BR); Erik Alphie LaChapelle, Uncasville, CT (US); Bruce Nelsen Rogers, Belmont, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/629,215

(22) Filed: Jun. 21, 2017

(65) Prior Publication Data
US 2017/0304312 A1 Oct. 26, 2017

Related U.S. Application Data

(63) Continuation of application No. 15/427,350, filed on Feb. 8, 2017, now Pat. No. 9,744,173, which is a continuation of application No. 15/215,193, filed on Jul. 20, 2016, now Pat. No. 9,605,007, which is a continuation of application No. 15/019,342, filed on Feb. 9, 2016, now Pat. No. 9,428,523, which is a continuation of application No. 14/682,151, filed on Apr. 9, 2015, now Pat. No. 9,315,520.

(60) Provisional application No. 62/119,862, filed on Feb. 24, 2015, provisional application No. 61/977,774, filed on Apr. 10, 2014.

(51) Int. Cl.
| | | |
|---|---|---|
| *C07D 519/00* | (2006.01) | |
| *C07D 513/04* | (2006.01) | |
| *A61K 31/542* | (2006.01) | |

(52) U.S. Cl.
CPC .................. *A61K 31/542* (2013.01)

(58) Field of Classification Search
CPC ... C07D 519/00; C07D 513/04; A61K 31/542
USPC ......................................... 544/48; 514/224.2
See application file for complete search history.

(56) References Cited

U.S. PATENT DOCUMENTS

| | | | |
|---|---|---|---|
| 5,750,349 A | 5/1998 | Suzuki et al. | |
| 7,115,600 B2 | 10/2006 | Wager et al. | |
| 7,285,293 B2 | 10/2007 | Castillo et al. | |
| 7,975,664 B2 | 7/2011 | Himsel et al. | |
| 8,158,620 B2 | 4/2012 | Suzuki et al. | |
| 8,198,269 B2 | 6/2012 | Motoki et al. | |
| 8,278,441 B2 | 10/2012 | Mergott et al. | |
| 8,729,071 B2 | 5/2014 | Scott et al. | |
| 8,822,456 B2 | 9/2014 | Brodney et al. | |
| 8,865,706 B2 | 10/2014 | Brodney et al. | |
| 8,933,221 B2 | 1/2015 | Brodney et al. | |
| 8,962,616 B2 | 2/2015 | Brodney et al. | |
| 9,045,498 B2 | 6/2015 | Brodney et al. | |
| 9,045,499 B2 | 6/2015 | Brodney et al. | |
| 9,192,612 B2 | 11/2015 | Brodney et al. | |
| 9,198,917 B2 | 12/2015 | Brodney et al. | |
| 9,233,981 B1 | 1/2016 | Brodney et al. | |
| 9,260,455 B2 | 2/2016 | Brodney et al. | |
| 9,315,520 B2* | 4/2016 | Brodney | C07D 513/04 |
| 9,403,846 B2 | 8/2016 | Brodney et al. | |
| 9,428,523 B2* | 8/2016 | Brodney | C07D 519/00 |

(Continued)

FOREIGN PATENT DOCUMENTS

| | | |
|---|---|---|
| EP | 0994728 | 10/1998 |
| EP | 127584 | 10/2004 |

(Continued)

OTHER PUBLICATIONS

Haan, J., et al., "Amyloid in Central Nervous System Disease", Clinical Neurology and Neurosurgery, 1990, pp. 305-310, 92(4).
Glenner, G., et al., "Amyloidosis of the Nervous System", Journal of Neurological Science, Dec. 1989, pp. 1-28, vol. 94.
Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).
Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).

(Continued)

*Primary Examiner* — Kahsay Habte
(74) *Attorney, Agent, or Firm* — Lisa A. Samuels

(57) ABSTRACT

The present invention is directed to compounds, tautomers and pharmaceutically acceptable salts of the compounds which are disclosed, wherein the compounds have the structure of Formula I,

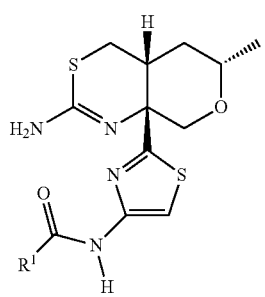

and the variable $R^1$ is as defined in the specification. Corresponding pharmaceutical compositions, methods of treatment, methods of synthesis, and intermediates are also disclosed.

40 Claims, No Drawings

(56) References Cited

U.S. PATENT DOCUMENTS

| | | | |
|---|---|---|---|
| 9,605,007 B2* | 3/2017 | Brodney | ............ C07D 513/04 |
| 9,611,264 B1 | 3/2017 | Brodney et al. | |
| 9,744,173 B2* | 8/2017 | Brodney | ............ A61K 31/542 |
| 2003/0073655 A1 | 4/2003 | Chain | |
| 2003/0195205 A1 | 10/2003 | DeNinno et al. | |
| 2004/0192898 A1 | 9/2004 | Jia et al. | |
| 2004/0220186 A1 | 11/2004 | Bell et al. | |
| 2005/0019328 A1 | 1/2005 | Schenk et al. | |
| 2005/0043354 A1 | 2/2005 | Wager et al. | |
| 2005/0048049 A1 | 3/2005 | Schenk et al. | |
| 2005/0256135 A1 | 11/2005 | Lunn et al. | |
| 2005/0267009 A1 | 12/2005 | Bernardelli et al. | |
| 2005/0267095 A1 | 12/2005 | Bernardelli et al. | |
| 2005/0267100 A1 | 12/2005 | Elliott et al. | |
| 2006/0057701 A1 | 3/2006 | Rosenthal et al. | |
| 2006/0106035 A1 | 5/2006 | Hendrix et al. | |
| 2006/0111372 A1 | 5/2006 | Hendrix et al. | |
| 2006/0178501 A1 | 8/2006 | Summers et al. | |
| 2007/0031416 A1 | 2/2007 | Shoji et al. | |
| 2007/0160616 A1 | 7/2007 | Rosenthal et al. | |
| 2007/0179175 A1 | 8/2007 | Lunn | |
| 2008/0096955 A1 | 4/2008 | Wager et al. | |
| 2008/0176925 A1 | 7/2008 | Bulter et al. | |
| 2009/0054482 A1 | 2/2009 | Chan et al. | |
| 2010/0056618 A1 | 3/2010 | Mascitti et al. | |
| 2010/0093999 A1 | 4/2010 | Motoki et al. | |
| 2010/0285145 A1 | 11/2010 | Darout et al. | |
| 2011/0009395 A1 | 1/2011 | Audia et al. | |
| 2011/0027279 A1 | 2/2011 | Chain | |
| 2011/0038861 A1 | 2/2011 | Rosenthal | |
| 2011/0046122 A1 | 2/2011 | Andreini et al. | |
| 2011/0207723 A1 | 8/2011 | Motoki et al. | |
| 2012/0245155 A1 | 9/2012 | Yoshida et al. | |
| 2013/0053373 A1 | 2/2013 | Brodney et al. | |
| 2013/0296308 A1 | 11/2013 | Brodney et al. | |
| 2014/0128382 A1 | 5/2014 | Wu et al. | |
| 2014/0163015 A1 | 6/2014 | Brodney et al. | |
| 2014/0228356 A1 | 8/2014 | Brodney et al. | |
| 2014/0323474 A1 | 10/2014 | Brodney et al. | |
| 2014/0364426 A1 | 12/2014 | Brodney et al. | |
| 2015/0087637 A1 | 3/2015 | Brodney et al. | |
| 2015/0133438 A1 | 5/2015 | Brodney et al. | |
| 2015/0224110 A1 | 8/2015 | Brodney et al. | |
| 2015/0231144 A1 | 8/2015 | Brodney et al. | |
| 2015/0239908 A1 | 8/2015 | Brodney et al. | |
| 2015/0291621 A1 | 10/2015 | Brodney et al. | |
| 2015/0376207 A1 | 12/2015 | Brodney et al. | |
| 2016/0002264 A1 | 1/2016 | Brodney et al. | |
| 2016/0152637 A1 | 6/2016 | Brodney et al. | |
| 2017/0088558 A1 | 3/2017 | Brodney et al. | |
| 2017/0151252 A1 | 6/2017 | Brodney et al. | |

FOREIGN PATENT DOCUMENTS

| | | |
|---|---|---|
| EP | 2332943 | 6/2011 |
| EP | 2511269 | 10/2012 |
| WO | 1998044955 | 10/1998 |
| WO | 2002020521 | 3/2002 |
| WO | 2003072197 | 9/2003 |
| WO | 2004032868 | 4/2004 |
| WO | 2005025616 | 3/2005 |
| WO | 2005049616 | 11/2005 |
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011009898 | 1/2011 |
| WO | 2011044181 | 4/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |
| WO | 2014045162 | 3/2014 |
| WO | 2014091352 | 6/2014 |
| WO | 2014097038 | 6/2014 |
| WO | 2014125394 | 8/2014 |
| WO | 2014125397 | 8/2014 |
| WO | 2015155626 | 10/2015 |
| WO | 2017051276 | 3/2017 |
| WO | 2017051294 | 3/2017 |
| WO | 2017051303 | 3/2017 |

OTHER PUBLICATIONS

Esterhazy, Daria, et al., "BACE2 Is a β Cell-Enriched Protease that Regulates Pancreatic β Cell Function and Mass", Cell Metabolism, Sep. 2011, pp. 365-377, 14(3).

Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).

Alberti, K.G. et al., "The Metabolic Syndrome—A New Worldwide Definition," Lancet, Sep. 24-30, 2005, pp. 1059-1062, 366(9491).

Haleblian, John K., "Characterization of Habits and Crystalline Modification of Solids and Their Pharmaceutical Applications", Journal Pharmaceutical Sciences, Aug. 1975, pp. 1269-1288, 64(8).

Finnin, Barrie, et al., "Transdermal Penetration Enhancers" Applications, Limitations, and Potential, Journal Pharmaceutical Sciences, Oct. 1999, pp. 955-958, 88(10).

Zhang, S. et al., "PTP1B as a Drug Target: Recent Developments in PTP1B Inhibitor Discovery", Drug Discovery Today, May 2007, pp. 373-381, 12(9/10).

Chao, Edward, et al., "SGLT2 Inhibition-A Novel Strategy for Diabetes Treatment", Nature Reviews Drug Discovery, Jul. 2010, pp. 551-559, 9(7).

Demong, D.E. et al., "Chapter 8, Glucagon Receptor Antagonists for Type II Diabetes", Annual Reports in Medicinal Chemistry 2008, pp. 119-137, vol. 43.

Jones, R.M. et al., "Chapter 7, The Emergence of GPR119 Agonists as Anti-Diabetic Agents", Annual Reports in Medicinal Chemistry 2009, pp. 149-170, vol. 44.

Zhong, M., "TGR5 as a Therapeutic Target for Treating Obesity", Current Topics in Medicinal Chemistry, 2010, pp. 386-396, 10(4).

Medina, J.C., et al., "Chapter 5, GPR40 (FFAR1) Modulators", Annual Reports in Medicinal Chemistry 2008, pp. 75-85, vol. 43.

Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).

Spek, A.L., "Single-Crystal Structure Validation with the Program Platon", Journal of Applied Crystallography, Feb. 2003, pp. 7-13, 36(1).

Macrae, Clare, et al., "Mercury: Visualization and Analysis of Crystal Structures", Journal of Applied Crystallography, Jun. 2006, pp. 453-457, 39(3).

(56) References Cited

OTHER PUBLICATIONS

Hooft, Rob, et al., "Determination of Absolute Structure Using Bayesian Statistics on Bijvoet differences", Journal of Applied Crystallography, Feb. 2008, pp. 96-103, 41(1).
Flack, H.D., "On Enantiomorph-Polarity Estimation", Acta Cryst., 1983, pp. 876-881, vol. A39.
England, et al., "An Improved Synthesis of a Novel α1A Partial Agonist Including a New Two-Step Synthesis of Fluoropyrazole", Tetrahedron Letters, May 26, 2010, pp. 2849-2851, 51(21).
Kharitonenkov, A. et al., "FGF21: A Novel Prospect for the Treatment of Metabolic Diseases", Current Opinion in Investigational Drugs, Apr. 2009, pp. 359-364, 10(4).
Denmark, S.E., et al., "Allylation of Carbonyls: Methodology and Stereochemistry", Modem Carbonyl Chemistry, 2000, Chapter 10, pp. 299-401.
Miyaura, N., et al., "Palladium-Catalyzed Cross-Coupling Reactions of Organobom Compounds", Chemical Review, Nov. 1995, pp. 2457-2483, 95(7).
Olsen, R., et al., "Secretase Inhibitors and Modulators for the Treatment of Alzheimer's Disease", Annual Reports in Medicinal Chemistry, 2007, pp. 27-47, vol. 42.
International Application No. PCT/IB2012/054198, filed Aug. 17, 2012, International Search Report and Written Opinion, dated Jan. 23, 2013, 14 pages.
Sheppeck, J.E. II, et al., "A Convenient and Scaleable Procedure for Removing the Fmoc Group in Solution", Tetrahedron Letters, 2000, pp. 5329-5333, vol. 41(28).
Suzuki, Akira, "Recent advances in the cross-coupling reactions of organoboron derivatives with organic electrophiles 1995-1998", Journal Organometallic Chemistry, 1999, pp. 147-168, vol. 576.
International Application No. PCT/IB2013/053178, filed Apr. 22, 2013, International Written Opinion and Search Report, dated Jul. 3, 2013, 10 pages.
English equivalent U.S. Pat. No. 8,158,620; Suzuki, et al., filed Jan. 16, 2009 for WO 2009091016, published Jun. 23, 2007.
International Application No. PCT/IB2013/058402, filed Sep. 9, 2013, International Search Report and Written Opinion, dated Dec. 16, 2013, 11 pages.
International Application No. PCT/IB2013/060456, filed Nov. 27, 2013, International Search Report, dated Feb. 21, 2014, 8 pages.
PCT/IB2013/060633 application filed Dec. 4, 2013.
PCT/IB2013/058402 application filed Sep. 9, 2013.
PCT/IB2013/060456 application filed Nov. 27, 2013.
PCT/IB2014/058760 application filed Feb. 3, 2014.
PCT/IB2014/058777 application filed Feb. 4, 2014.
Guidance for Industry, Q3C-Tables and List, U.S. Department of Health and Human Services, Food and Drug Administration, Center for Drug Evaluation and Research (CDER), Center for Biologics Evaluation and Research (CBER), Nov. 2003, ICH, Revision I.
International Application No. PCT/IB2014/0558760 filed Feb. 3, 2014, International Preliminary Report on Patentability, dated Aug. 18, 2015, 7 pages.
International Application No. PCT/IB2014/0558777 filed Feb. 4, 2014, International Preliminary Report on Patentability, dated Aug. 18, 2015, 7 pages.
International Application No. PCT/IB2014/0558760 filed Feb. 3, 2014, International Search Report and Written Opinion, dated Mar. 13, 2014, 10 pages.
International Application No. PCT/IB2013/060456, filed Nov. 27, 2013, International Preliminary Report on Patentability, dated Jun. 16, 2015, 5 pages.
International Application No. PCT/IB2013/060633, filed Dec. 4, 2013, International Preliminary Report on Patentability, dated Jun. 23, 2015.
International Application No. PCT/IB2013/060633, filed Dec. 4, 2013, International Search Report and Written Opinion, dated Mar. 24, 2014.
International Application No. PCT/IB2015/052279, filed Mar. 27, 2015, International Search Report and Written Opinion, dated Jun. 24, 2015, 10 pages.
International Patent Application No. PCT/IB2014/058777, filed Feb. 4, 2014, International Search Report and Written Opinion, dated Mar. 25, 2014, 11 pages.
International Application No. PCT/IB2016/055399, filed Sep. 9, 2016, International Search Report and Written Opinion, dated Nov. 2, 2016, 14 pages.
International Application No. PCT/IB2016/055580, filed Sep. 19, 2016, International Search Report and Written Opinion, dated Oct. 24, 2016, 12 pages.
International Application No. PCT/IB2016/055536, filed Sep. 19, 2016, International Search Report and Written Opinion, dated Oct. 25, 2016, 10 pages.
Shimshek, Derya R., et al., "Pharmacological BACE1 and BACE2 inhibition induces hair depigmentation by inhibiting PMEL17 processing in mice", Scientific Reports, [6:21917] Feb. 25, 2016, pp. 1-13.

\* cited by examiner

2-AMINO-6-METHYl-4,4A,5,6-TETRAHYDROPYRANO[3,4-D][1,3]THIAZIN-8A(8H)-YL-1,3-THIAZOL-4-YL AMIDES

This application is a continuation application of U.S. patent application Ser. No. 15/427,350, filed Feb. 8, 2017, which is a continuation application of U.S. patent application Ser. No. 15/215,193, filed Jul. 20, 2016 which is a continuation application of U.S. patent application Ser. No. 15/019,342, filed Feb. 9, 2016, which claims the benefit of continuation application U.S. patent application Ser. No. 14/682,151, filed Apr. 9, 2015, which claims the benefit of U.S. Provisional Patent Application No. 62/119,862, filed on Feb. 24, 2015 and U.S. Provisional Patent Application No. 61/977,774, filed on Apr. 10, 2014, the disclosures of which are hereby incorporated by reference in their entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's Disease (AD) and other neurodegenerative and/or neurological disorders, as well as the treatment of diabetes in mammals, including humans. More particularly, this invention relates to thioamidine compounds and pharmaceutically acceptable salts thereof useful for the treatment of neurodegenerative and/or neurological disorders, such as AD and Down's Syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4):305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's Disease (AD), which is the most common cause of cognitive decline in the elderly (Hardy & Allsop, Trends Pharmacol Sci., 1991; 12(10):383-8; Selkoe, Behav. Brain Res., 2008; 192 (1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme.

Co-pending PCT application, PCT/162012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I

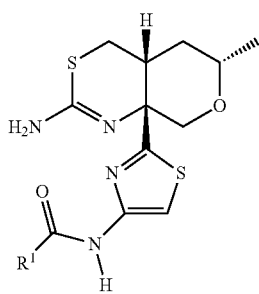

I wherein
$R^1$ is selected from the group consisting of:
phenyl optionally substituted with one to three $R^2$;
$C_{3-9}$cycloalkyl optionally substituted with one to three $R^2$; and
a 5- to 10-membered heteroaryl, having one to four heteroatoms independently selected from N, O or S, wherein at least one of the heteroatoms is N and wherein said N is optionally substituted with $R^3$; and wherein said 5- to 10-membered heteroaryl is optionally substituted on carbon with one to three $R^2$;
$R^2$ at each occurrence is independently selected from the group consisting of halogen, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$ alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; or two $R^2$ groups taken together can be a $C_{3-5}$alkylene;
$R^3$ is hydrogen, $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$ alkyl; wherein said $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; or $R^3$ and $R^2$ taken together can be a $C_{3-5}$alkylene;
or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's Disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:
(1) Methods of inhibiting BACE enzyme activity, by administering a therapeutically effective amount of a thioamidine compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendent claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

The term "alkenyl" refers to a linear or branched-chain hydrocarbyl substituent (i.e., a substituent obtained from a hydrocarbon by removal of a hydrogen) which contains at least one carbon-carbon double bond; in one embodiment containing from three to six carbon atoms. Non-limiting examples of such substituents include allyl, propenyl, butenyl, isobutenyl, butadienyl, pentenyl, pentadienyl, hexenyl, hexadienyl and the like. The term "alkenyloxy" refers to an alkenyl group attached to an oxygen radical.

The term "alkynyl" refers to a linear or branched-chain hydrocarbyl substituent (i.e., a substituent obtained from a hydrocarbon by removal of a hydrogen) which contains at least one carbon-carbon triple bond; in one embodiment containing from three to six carbon atoms. Non-limiting examples of such substituents include propynyl, butynyl, isobutynyl, pentynyl, hexynyl and the like. The term "alkynyloxy" refers to an alkynyl group attached to an oxygen radical.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms or having three to nine carbon atoms. The term "cycloalkyl" includes mono-, bi- and tricyclic saturated carbocycles, as well as bridged and fused ring carbocycles and also spiro-fused carbocyclic ring systems. The term "$C_{3-9}$cycloalkyl" means a radical of a three to nine membered ring system which includes the groups cyclopropyl, cyclobutyl, cyclopentyl, cyclohexyl, cycloheptyl, cyclooctyl, cyclononyl, bicyclopentyl, bicyclohexyl, bicycloheptyl, bicyclooctyl, bicyclononyl, spiropentyl, spirohexyl, spiroheptyl, spirooctyl and spirononyl. The term "$C_{3-6}$cycloalkyl" means a radical of a three to six membered ring system which includes the groups cyclopropyl, cyclobutyl, cyclopentyl, cyclohexyl, bicyclopentyl, bicyclohexyl, spiropentyl and spirohexyl. The term "$C_{3-6}$cycloalkoxy" refers to a three to six membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five membered heteroaromatic ring system and a six membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2

(1H)-onyl, pyridazin-2(1H)-onyl, pyrimidin-2(1H)-onyl, pyrazin-2(1H)-onyl, imidazo[1,2-a]pyridinyl, and pyrazolo [1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydro-quinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo [1,5-a]pyridinyl, 4,5,6,7-tetrahydro-1H-indazolyl and 4,5,6, 7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (———), a solid wedge (◥) or a dotted wedge (⊪⊪⊪⊪). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 2-aminodihydrothiazine form, I, and the 2-imino-tetrahydrothiazine form, Ia. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula I and Ia and, collectively and generically, are referred to as compounds of Formula I.

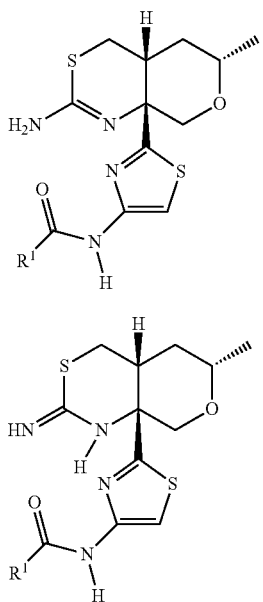

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of a first aspect of the present invention is a compound of Formula I:

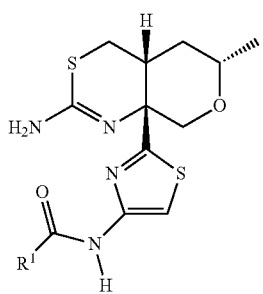

I wherein
$R^1$ is selected from the group consisting of:
phenyl optionally substituted with one to three $R^2$;
$C_{3-6}$cycloalkyl optionally substituted with one to three $R^2$; and
a 5- to 10-membered heteroaryl, having one to four heteroatoms independently selected from N, O or S, wherein at least one of the heteroatoms is N and wherein said N is optionally substituted with $R^3$; and wherein said 5- to 10-membered heteroaryl is optionally substituted on carbon with one to three $R^2$;
$R^2$ at each occurrence is independently selected from the group consisting of halogen, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$ alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, methyl, fluoromethyl, difluoromethyl, trifluoromethyl, methoxy, fluoromethoxy, difluoromethoxy and trifluoromethoxy; or two $R^2$ groups taken together can be a $C_{3-5}$alkylene;

$R^3$ is hydrogen, $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$ alkyl; wherein said $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$alkyl are each optionally substituted with one to three substituents independently selected from fluoro, chloro, hydroxy, methyl, fluoromethyl, difluoromethyl, trifluoromethyl, methoxy, fluoromethoxy, difluoromethoxy and trifluoromethoxy; or $R^3$ and $R^2$ taken together can be a $C_{3-5}$alkylene;
or a tautomer thereof or a pharmaceutically acceptable salt of said compound or tautomer.

A third embodiment of the first aspect of the present invention is the compound of the second embodiment of the first aspect wherein $R^1$ is a 5-membered heteroaryl selected from the group consisting of pyrazolyl, imidazolyl, oxazolyl, isoxazolyl, oxadiazolyl and triazolyl; each optionally substituted on carbon with one to two $R^2$; and wherein said pyrazolyl, imidazolyl and triazolyl are substituted on N with $R^3$; $R^2$ at each occurrence is independently selected from the group consisting of halogen, $C_{1-3}$alkyl, $C_{3-6}$cycloalkyl, and $C_{1-3}$alkoxy-$C_{1-3}$alkyl; wherein said $C_{1-3}$alkyl is optionally substituted with one to three fluoro; and $R^3$ is $C_{1-3}$alkyl or $C_{3-6}$cycloalkyl, wherein said $C_{1-3}$alkyl is optionally substituted with one to three fluoro; or a tautomer thereof or a pharmaceutically acceptable salt of said compound or tautomer.

A fourth embodiment of the first aspect of the present invention is the compound of the third embodiment of the first aspect wherein $R^1$ is selected from the group consisting of

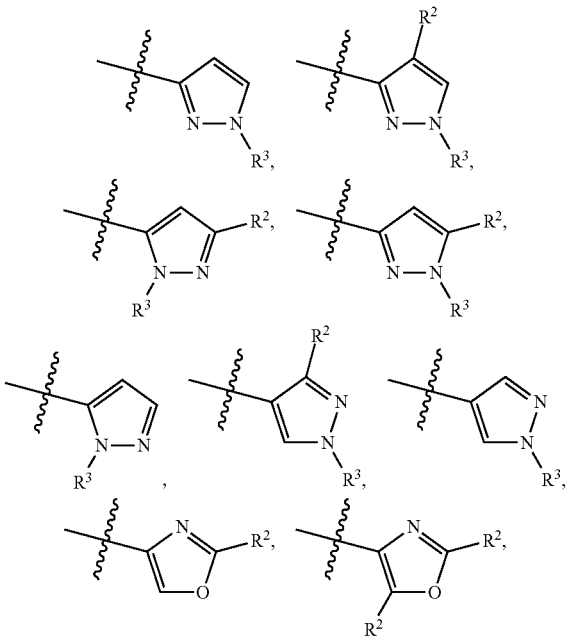

-continued

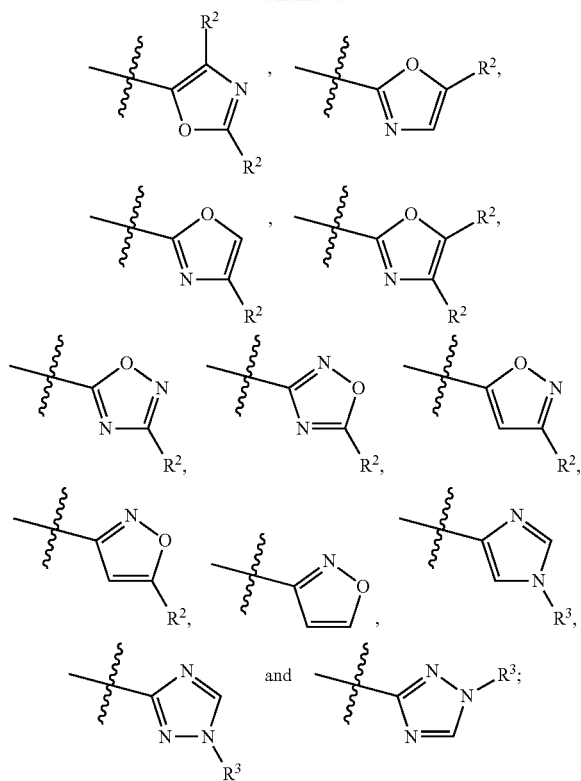

R² at each occurrence is independently selected from the group consisting of chloro, methyl, ethyl, isopropyl, isobutyl, fluoromethyl, difluoromethyl, trifluoromethyl, cyclopropyl, cyclobutyl and methoxymethyl; and R³ is methyl, ethyl, isopropyl, difluoromethyl, cyclopropyl or cyclobutyl; or a tautomer thereof or a pharmaceutically acceptable salt of said compound or tautomer.

A fifth embodiment of the first aspect of the present invention is the compound of the fourth embodiment of the first aspect wherein R¹ is selected from the group consisting of

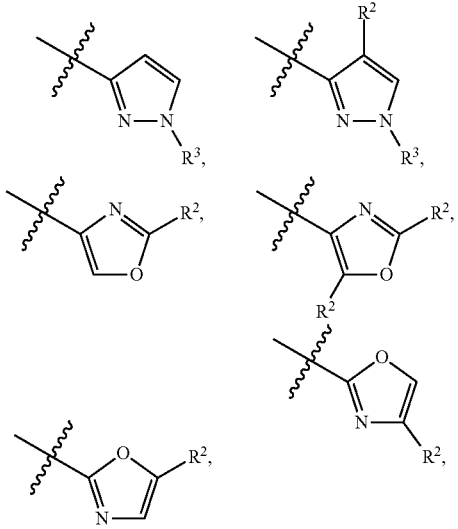

-continued

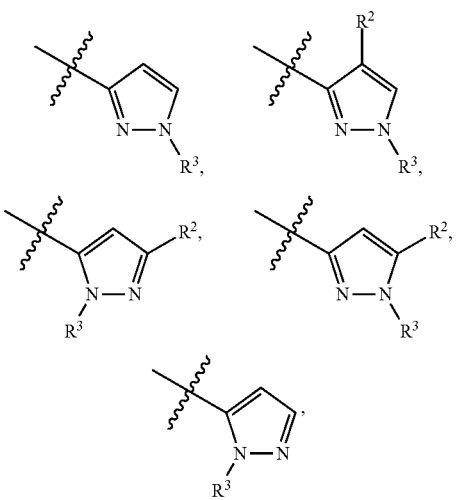

or a tautomer thereof or a pharmaceutically acceptable salt of said compound or tautomer.

A sixth embodiment of the first aspect of the present invention is the compound of the fourth embodiment of the first aspect wherein R¹ is selected from the group consisting of

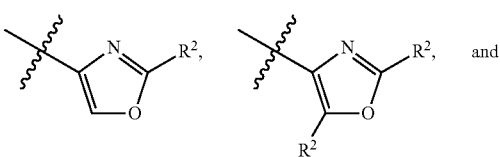

or a tautomer thereof or a pharmaceutically acceptable salt of said compound or tautomer.

A seventh embodiment of the first aspect of the present invention is the compound of the fourth embodiment of the first aspect wherein R¹ is selected from the group consisting of

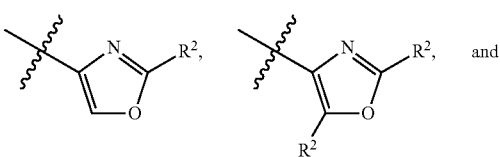

-continued

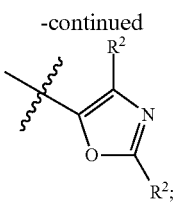

or a tautomer thereof or a pharmaceutically acceptable salt of said compound or tautomer.

An eighth embodiment of the first aspect of the present invention is the compound of the fourth embodiment of the first aspect wherein R¹ is selected from the group consisting of

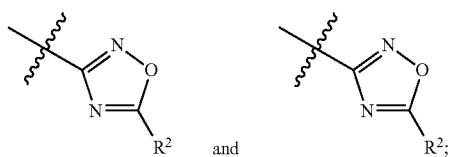

or a tautomer thereof or a pharmaceutically acceptable salt of said compound or tautomer.

A ninth embodiment of the first aspect of the present invention is the compound of the fourth embodiment of the first aspect wherein R¹ is selected from the group consisting of

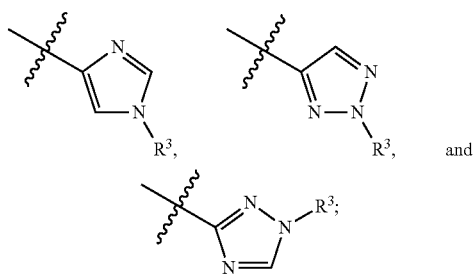

or a tautomer thereof or a pharmaceutically acceptable salt of said compound or tautomer.

A tenth embodiment of the first aspect of the present invention is the compound of the second embodiment of the first aspect wherein R¹ is a 6-membered heteroaryl selected from the group consisting of pyridinyl, pyridonyl, pyrimidinyl, pyridazinyl and pyrazinyl; each optionally substituted on carbon with one to two R²; and wherein said pyridonyl is substituted on N with R³; R² at each occurrence is independently selected from the group consisting of halogen, hydroxy, cyano, $C_{1-6}$alkyl, $C_{1-6}$alkoxy, $C_{1-6}$alkoxy-$C_{1-6}$alkyl, $C_{3-6}$cycloalkyl, $C_{3-6}$alkynyloxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{1-6}$alkoxy-$C_{1-6}$alkyl, $C_{3-6}$cycloalkyl, $C_{3-6}$alkynyloxy, 4- to 6-membered heterocycloalkyl and 4- to 6-membered heterocycloalkyl-$C_{1-6}$alkyl are optionally substituted with one to three fluoro or hydroxy; and R³ is $C_{1-3}$alkyl; or a tautomer thereof or a pharmaceutically acceptable salt of said compound or tautomer.

An eleventh embodiment of the first aspect of the present invention is the compound of the tenth embodiment of the first aspect wherein R¹ is selected from the group consisting of

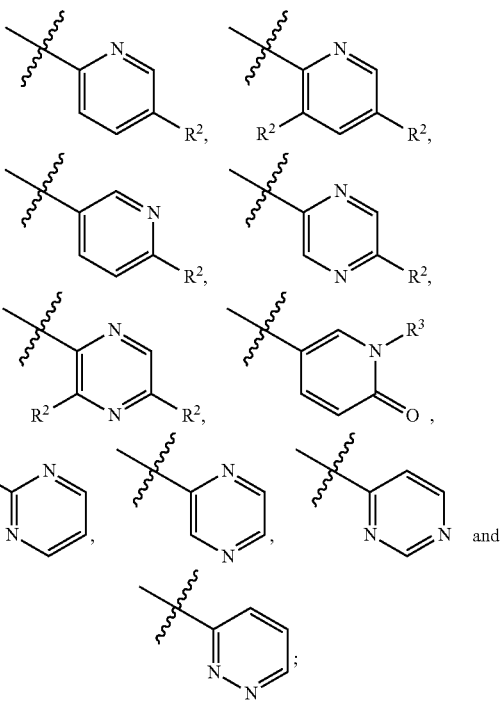

R² at each occurrence is independently selected from the group consisting of fluoro, chloro, cyano, methyl, fluoromethyl, difluoromethyl, trifluoromethyl, hydroxy, hydroxymethyl, methoxy, fluoromethoxy, difluoromethoxy, trifluoromethoxy, difluoroethoxy, methoxydifluoroethyl, difluoropropoxy, butynyloxy and cyclopropyl; and R³ is methyl; or a tautomer thereof or pharmaceutically acceptable salt of said compound or tautomer.

A twelfth embodiment of the first aspect of the present invention is the compound of the eleventh embodiment of the first aspect wherein
R¹ is

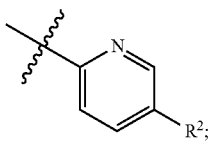

or a tautomer thereof or a pharmaceutically acceptable salt of said compound or tautomer.

An thirteenth embodiment of the first aspect of the present invention is the compound of the eleventh embodiment of the first aspect wherein
R¹ is

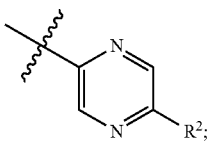

or a tautomer thereof or a pharmaceutically acceptable salt of said compound or tautomer.

A fourteenth embodiment of the first aspect of the present invention is the compound of the second embodiment of the first aspect wherein R¹ is phenyl optionally substituted with one to two R², or C$_{3-6}$cycloalkyl optionally substituted with one to two R²; or a tautomer thereof or a pharmaceutically acceptable salt of said compound or tautomer.

A fifteenth embodiment of the first aspect of the present invention is the compound of the second embodiment of the first aspect selected from the group consisting of:

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyanopyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxypyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(fluoromethyl)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoroethoxy)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoro-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethyl)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3,5-difluoropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxypyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethoxy)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(but-2-yn-1-yloxy)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethyl)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(fluoromethoxy)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyridazine-3-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-6-oxo-1,6-dihydropyridine-3-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoroethoxy)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoroethoxy)pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxy-3-methylpyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxy-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrimidine-4-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methylpyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrimidine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyclopropylpyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrazolo[1,5-a]pyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-6-(difluoromethoxy)pyridine-3-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyclopropylmethoxy)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyclopropyloxy)pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-{[(2R)-2-fluoropropyl]oxy}pyrazine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-{[(2S)-2-fluoropropyl]oxy}pyrazine-2-carboxamide; and N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide;

or a tautomer thereof or a pharmaceutically acceptable salt of said compound or tautomer.

A sixteenth embodiment of the first aspect of the present invention is the compound of the second embodiment of the first aspect selected from the group consisting of:

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-chloro-(difluoromethyl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,3-dimethyl-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-cyclobutyl-1-methyl-1H-pyrazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-ethyl-1-methyl-1H-pyrazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,3-dimethyl-1H-pyrazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-methyl-3-(trifluoromethyl)-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-5-(2-methylpropyl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5,6-dihydro-4H-pyrrolo[1,2-b]pyrazole-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-3-(propan-2-yl)-1H-pyrazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-ethyl-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,5-dimethyl-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloro-1-methyl-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-1H-pyrazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-5-carboxamide;
or a tautomer thereof or a pharmaceutically acceptable salt of said compound or tautomer.

A seventeenth embodiment of the first aspect of the present invention is the compound of the second embodiment of the first aspect selected from the group consisting of:
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(difluoromethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-cyclopropyl-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-methyl-5-(trifluoromethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-ethyl-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2,4-dimethyl-1,3-oxazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(propan-2-yl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazole-4-yl}-2-(propan-2-yl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(trifluoromethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-methyl-1,2,4-oxadiazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methyl-1,2,4-oxadiazole-3-carboxamide; and
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2,5-dimethyl-1,3-oxazole-4-carboxamide;
or a tautomer thereof or a pharmaceutically acceptable salt of said compound or tautomer.

An eighteenth embodiment of the first aspect of the present invention is the compound of the second embodiment of the first aspect selected from the group consisting of:
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyclopropyl-1,2-oxazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)-1,2-oxazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(methoxymethyl)-1,2-oxazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2-methylpropyl)-1,2-oxazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methyl-1,2-oxazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-methyl-1,2-oxazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-ethyl-1,2-oxazole-5-carboxamide; and
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,2-oxazole-3-carboxamide;
or a tautomer thereof or a pharmaceutically acceptable salt of said compound or tautomer.

A nineteenth embodiment of the first aspect of the present invention is the compound of the second embodiment of the first aspect selected from the group consisting of:

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-fluorobenzamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-(difluoromethoxy)benzamide; and
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3,3-difluorocyclobutanecarboxamide;
or a tautomer thereof or a pharmaceutically acceptable salt of said compound or tautomer.

A twentieth embodiment of the first aspect of the present invention is the compound of the second embodiment of the first aspect selected from the group consisting of:

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclobutyl-1H-imidazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-methyl-2H-1,2,3-triazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,4-triazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(propan-2-yl)-1H-imidazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,4-triazole-5-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-imidazole-4-carboxamide; and
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,3-triazole-4-carboxamide;
or a tautomer thereof or a pharmaceutically acceptable salt of said compound or tautomer.

A twenty first embodiment of the first aspect of the present invention is the compound of the first embodiment of the first aspect selected from the group consisting of:

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(2,2-difluoroethyl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(2-methoxyethyl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(prop-2-yn-1-yl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(methoxymethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(2,2,2-trifluoroethyl)-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(but-2-yn-1-yl)-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}cyclobutanecarboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-(difluoromethyl)-1,3-oxazole-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-4-methyl-1H-pyrazole-3-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyrimidine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoro-2-methoxyethyl)pyrazine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyanomethoxy)pyridine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(fluoromethyl)-5-methyl-1,3-oxazole-4-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoro-2-methoxyethyl)pyridine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoropropoxy)pyridine-2-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}bicyclo[1.1.1]pentane-1-carboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyanocyclopropanecarboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}cyclopropanecarboxamide;
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyanocyclobutanecarboxamide; and
N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methylcyclobutanecarboxamide;
or a tautomer thereof or a pharmaceutically acceptable salt of said compound or tautomer.

A twenty second embodiment of the first aspect of the present invention is the compound N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer. A twenty third embodiment of the first aspect of the present invention is the compound N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide; or a tautomer thereof or a pharmaceutically acceptable salt of said compound or tautomer. A twenty fourth embodiment of the first of the present invention is the compound N-{2-[(4aR,6S,8aR)-2-Amino- 6-methyl-4,4a,5,6-tetrahydropyrano[3,4-d][1,3]thiazin-8a (8H)-yl]-1,3-thiazol-4-yl}-5-chloropyridine-2-carboxamide; or a tautomer thereof or a pharmaceutically acceptable salt of said compound or tautomer. A twenty fifth embodiment of the first aspect of the present invention is the compound N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide; or a tautomer thereof or a pharmaceutically acceptable salt of said compound or tautomer. A twenty sixth embodiment of a first aspect of the present invention is the compound N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide; or a tautomer thereof or a pharmaceutically acceptable salt of said compound or tautomer. A twenty seventh embodiment of a first aspect of the present invention is the compound N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; or a tautomer thereof or a pharmaceutically acceptable salt of said compound or tautomer. A twenty eighth embodiment of a first aspect of the present invention is the compound N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer.

A first embodiment of a second aspect of the present invention is a pharmaceutical composition comprising a therapeutically effective amount of a compound of any one of the first to twenty eighth embodiments of the first aspect of the present invention, or a tautomer thereof or a pharmaceutically acceptable salt of said compound or tautomer, and a pharmaceutically acceptable vehicle, diluent or carrier.

Further embodiments of the present invention include methods of treatment employing the compounds of the present invention.

A first embodiment of a third aspect of the present invention is a method of inhibiting production of amyloid-β protein in a patient; the method comprising administering a therapeutically effective amount of a compound according to any one of the first through twenty eighth embodiments of the first aspect of the present invention, or a tautomer thereof or a pharmaceutically acceptable salt of said compound or tautomer to a patient in need of inhibition of production of amyloid-β protein.

A second embodiment of a third aspect of the present invention is a method of inhibiting beta-site amyloid precursor protein cleaving enzyme 1 (BACE1) in a patient, the method comprising administering a therapeutically effective amount of a compound according to any one of the first through twenty eighth embodiments of the first aspect of the present invention, or a tautomer thereof or a pharmaceutically acceptable salt of said compound or tautomer to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound according to any one of the first through twenty eighth embodiments of the first aspect of the present invention, or a tautomer thereof or a pharmaceutically acceptable salt of said compound or tautomer to a patient in need of treatment thereof.

A fourth embodiment of a third aspect of the present invention is the method of the third embodiment of the third aspect wherein the neurodegenerative disease is Alzheimer's Disease.

A fifth embodiment of a third aspect of the present invention is a method of treating or preventing diabetes in a patient, the method comprising administering a therapeutically effective amount of a compound according to any one of first through twenty eighth embodiments of the first aspect of the present invention, or a tautomer thereof or a pharmaceutically acceptable salt of said compound or tautomer to a patient in need of treatment or prevention thereof.

A sixth embodiment of a third aspect of the present invention is the method of the fifth embodiment of the third aspect wherein the diabetes is Type 2 diabetes.

Further embodiments of the present invention include the use of a compound according to any one of first through twenty eighth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., *Drug Discovery Today,* 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g., SSTR1, SSTR2, SSTR3 and SSTR5), inhibitors or modulators of PDHK2 or PDHK4, inhibitors of MAP4K4, modulators of IL1 family including IL1beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALINC®), tacrine (COGNEX®), tolserine, memoquin, huperzine A (HUP-A; Neuro-Hitech), phenserine, bisnorcymserine (also known as BNC), and INM-176;

(vi) amyloid-ß (or fragments thereof), such as $Aß_{1-15}$ conjugated to pan HLA DR-binding epitope (PADRE®), ACC-001 (Elan/Wyeth), and Affitope;

(vii) antibodies to amyloid-ß (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(xiv) serotonin (5-hydroxytryptamine) 1A (5-$HT_{1A}$) receptor antagonists, such as spiperone, levo-pindolol, lecozotan;

(xv) serotonin (5-hydroxytryptamine) 2C (5-$HT_{2C}$) receptor agonists, such as vabicaserin, and zicronapine; serotonin (5-hydroxytryptamine) 4 (5-$HT_4$) receptor agonists/antagonists, such as PRX-03140 (Epix) and PF-04995274;

(xvi) serotonin (5-hydroxytryptamine) 3C (5-$HT_{3C}$) receptor antagonists, such as Ondansetron (Zofran);

(xvii) serotonin (5-hydroxytryptamine) 6 (5-$HT_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

Scheme 1 refers to the preparation of compounds of Formula I. Referring to Scheme 1, the compound of Formula III can be prepared from the compound of Formula II via a standard peptide coupling with a carboxylic acid, and a suitable coupling reagent, for example but not limited to, O-7-azabenzotriazol-1-yl)-N,N,N',N'-tetramethyluronium hexafluorophosphate (HATU). A compound of Formula I can be prepared through removal of protecting group $P^1$. $P^1$ in this case refers to groups well known to those skilled in the art for amine protection. For example, $P^1$ may be a benzoyl group (Bz), which can be cleaved via basic conditions, including but not limited to treatment with methoxylamine hydrochloride and pyridine in ethanol. Alternatively $P^1$ may be one of many other protecting group suitable for amines, including 9-fluorenylmethoxycarbonyl (Fmoc) or tert-butoxycarbonyl (BOC) and can be cleaved under standard conditions known to one skilled in the art.

Scheme 1

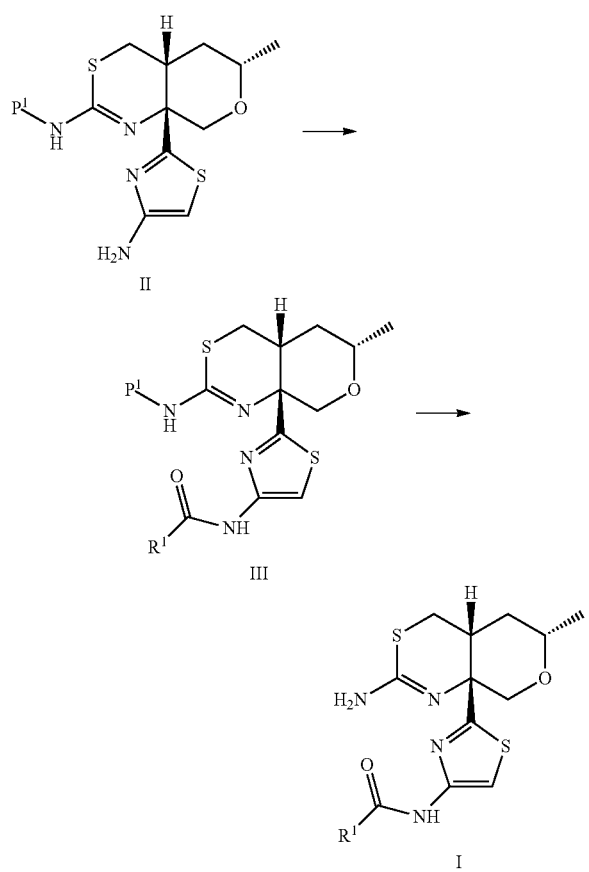

Scheme 2 refers to the preparation of compounds II wherein $P^1$ is Bz or Boc. Oxazolines of Formula IV are transformed to oxazolidines of Formula V via the addition of an appropriately metallated 2,4-dibromo-1,3-thiazole (generated, for example, through treatment with n-butyllithium) and boron trifluoride dietherate. Aminoalcohols of Formula VI are prepared through the reduction of compound V with a reducing agent, such as, but not limited to, molybdenum hexacarbonyl and sodium borohydride. Compounds of Formula VIII are then prepared via the treatment with the appropriate isothiocyanate (such as benzyl isothiocyanate), and subsequent ring closure using 1-Chloro-N,N,2-trimethylprop-1-en-1-amine (Ghosez's reagent). Conversion of the bromothiazole to the corresponding amine can be effected via a transitional metal-catalyzed coupling reaction, such as the palladium mediated amination. An example includes using a protected ammonia source, such as, but not limited to 1-(2,4-dimethoxyphenyl)methanamine and a suitable catalyst and ligand choice, for example, tris(dibenzylideneacetone)dipalladium(0) and di-tert-butyl[2',4',6'-tri(propan-2-yl)biphenyl-2-yl]phosphane. Alternatively one can utilize a copper-mediated azide coupling method. One skilled in the art will recognize that the requisite protected ammonia source will need to be deprotected to afford compounds of Formula II. In the example utilizing 1-(2,4-dimethoxyphenyl)methanamine, said deprotection can be effected via acidic hydrolysis, such as treatment with concentrated hydrochloric acid. Compound II can be converted into a compound of Formula I according to the methods of Scheme 1.

Scheme 2

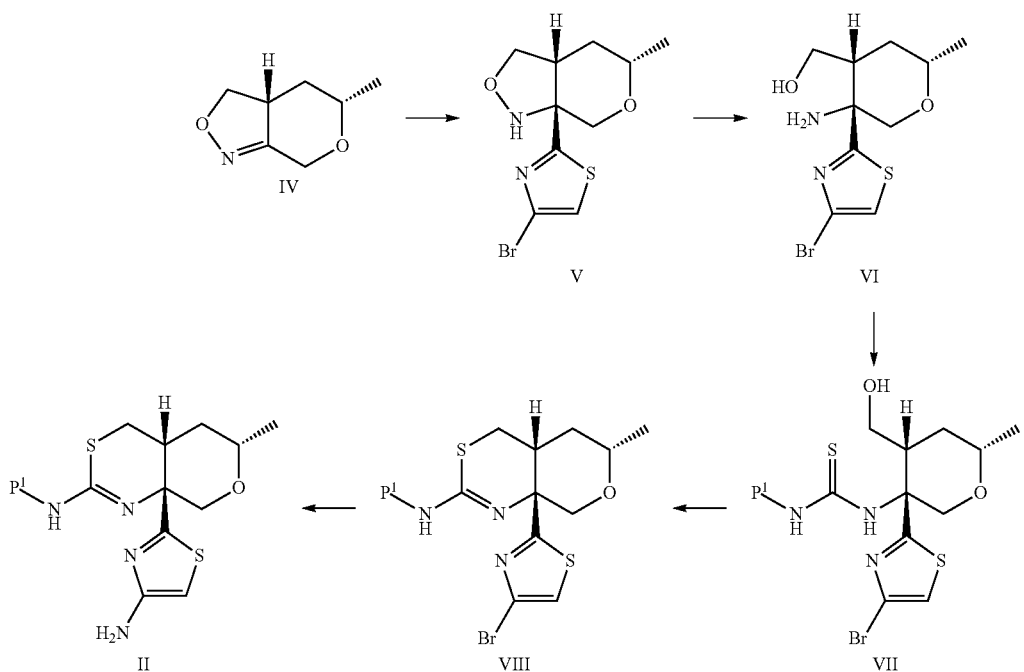

Scheme 3 refers to the preparation of compounds IV. The alkylation of compounds of Formula IX is effected using 2-bromo-1,1-diethoxyethane and sodium hydride in tetrahydrofuran. Deprotection of the diethylacetal of compounds of Formula X occurs using acidic conditions and subsequent oxime formation occurs via treatment with hydroxylamine hydrochloride to afford compounds of Formula XI. Treatment with sodium hypochlorite and triethylamine affords isoxazoline IV. A compound of Formula IV can be converted into a compound of Formula I according to the methods of Schemes 2 and 1.

Scheme 3

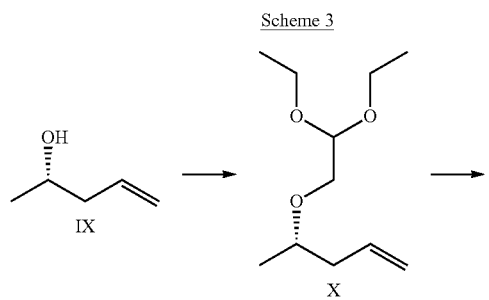

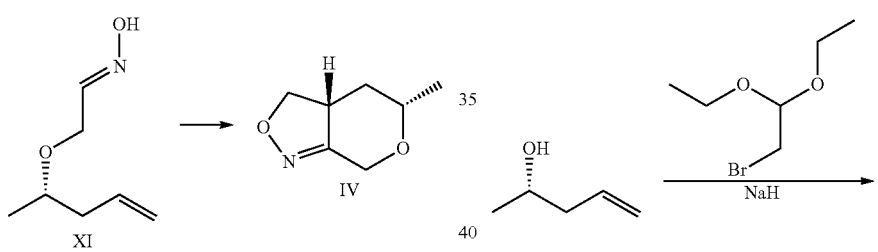

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. Where applicable in the examples, chiral separations can be carried out to separate enantiomers of certain compounds of the invention (in such examples, where applicable, the separated enantiomers can be designated as ENT-1 and ENT-2, according to their order of elution). In some examples, the optical rotation of an enantiomer can be measured using a polarimeter. According to its observed rotation data (or its specific rotation data), an enantiomer with a clockwise rotation is designated as the (+)-enantiomer and an enantiomer with a counter-clockwise rotation is designated as the (−)-enantiomer.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1

(3aR,5S)-5-Methyl-3,3a,4,5-tetrahydro-7H-pyrano[3,4-c][1,2]oxazole (P1)

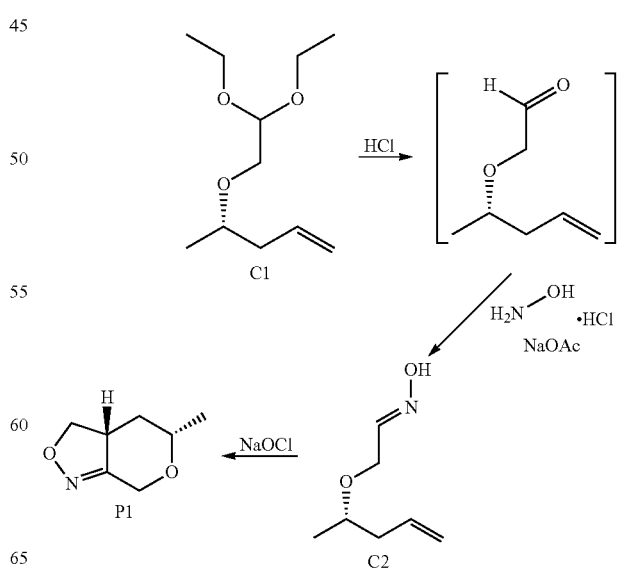

Step 1. Synthesis of (4S)-4-(2,2-diethoxyethoxy)pent-1-ene (C1)

To a suspension of sodium hydride (60% in mineral oil, 13.9 g, 0.348 mol) in tetrahydrofuran (350 mL) was added a solution of (S)-pent-4-en-2-ol (10.0 g, 0.116 mol) in tetrahydrofuran (50 mL) at 0° C. The reaction was warmed to room temperature and stirred for 30 minutes, whereupon 2-bromo-1,1-diethoxyethane (68.6 g, 0.348 mol) was added and the reaction mixture was heated to reflux for 18 hours. The reaction mixture was then cooled to 0° C., quenched with water (50 mL), and partitioned between ethyl acetate (300 mL) and water (200 mL). The organic layer was washed with saturated aqueous sodium chloride solution (2×100 mL), dried, and concentrated in vacuo. Silica gel chromatography (Eluent: 30:1 petroleum ether/ethyl acetate) provided the product as a yellow oil. Yield: 17.4 g, 86.0 mmol, 74%. $^1$H NMR (400 MHz, CDCl$_3$), δ 5.76-5.85 (m, 1H), 5.02-5.09 (m, 2H), 4.58-4.60 (m, 1H), 3.66-3.74 (m, 2H), 3.43-3.61 (m, 5H), 2.29-2.36 (m, 1H), 2.13-2.20 (m, 1H), 1.21 (t, J=7.2 Hz, 6H), 1.14 (d, J=6.4 Hz, 3H).

Step 2. Synthesis of (1E)-N-hydroxy-2-[(2S)-pent-4-en-2-yloxy]ethanimine (C2)

To a solution of C1 (17.4 g, 86.0 mmol) in tetrahydrofuran (100 mL) was added aqueous hydrochloric acid (2 M, 51.0 mL, 0.102 mol), and the reaction mixture was heated to 75° C. for 1 hour. After removal of solvent in vacuo, ethanol (100 mL) and water (20 mL) were added, followed by sodium acetate (35.17 g, 0.429 mol) and hydroxylamine hydrochloride (17.9 g, 0.257 mol). The reaction mixture was stirred at 60° C. for 18 hours, whereupon it was concentrated in vacuo; the residue was then partitioned between water and dichloromethane. The aqueous layer was extracted with dichloromethane (3×200 mL) and the combined organic layers were dried over sodium sulfate, filtered, and concentrated under reduced pressure. Silica gel chromatography (Eluent: 10:1 petroleum ether/ethyl acetate) provided the product as a yellow oil, which was used without further purification in the subsequent step. Yield: 8.6 g, 60 mmol, 70%.

Step 3. Synthesis of (3a R, 5S)-5-methyl-3,3a,4,5-tetrahydro-7H-pyrano[3,4-c][1,2]oxazole (P1)

To a solution of C2 (8.6 g, 60 mmol) and triethylamine (0.455 g, 4.50 mmol) in dichloromethane (150 mL) at room temperature was slowly added an aqueous solution of sodium hypochlorite (6%, 90 mL), at a rate that maintained the internal reaction temperature between 20° C. and 25° C. After completion of the addition, the organic layer was dried, filtered, and concentrated in vacuo. Silica gel chromatography (Eluent: 10:1 petroleum ether/ethyl acetate) provided the product as a yellow oil. Yield: 5.70 g, 40.4 mmol, 67%. LCMS m/z 142.1 [M+H$^+$], $^1$H NMR (400 MHz, CDCl$_3$), δ 4.68 (d, J=13.2 Hz, 1H), 4.59 (dd, J=10, 8 Hz, 1H), 4.18 (d, J=13.2 Hz, 1H), 3.76 (dd, J=12, 8 Hz, 1H), 3.59-3.66 (m, 1H), 3.39-3.50 (m, 1H), 2.14-2.19 (m, 1H). 1.42-1.51 (m, 1H), 1.25 (d, J=6 Hz, 3H).

Preparation P2

N-[(4aR,6S,8aR)-8a-(4-Amino-1,3-thiazol-2-yl)-6-methyl-4,4a,5,6,8,8a-hexahydropyrano[3,4-d][1,3]thiazin-2-yl]benzamide (P2)

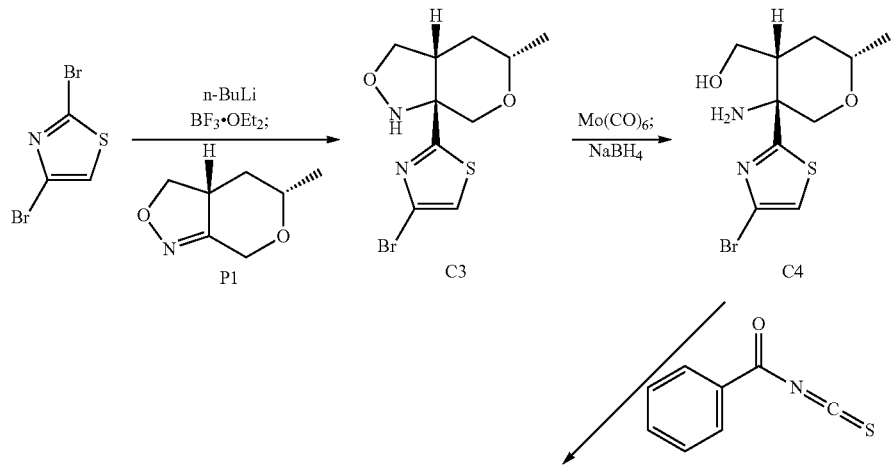

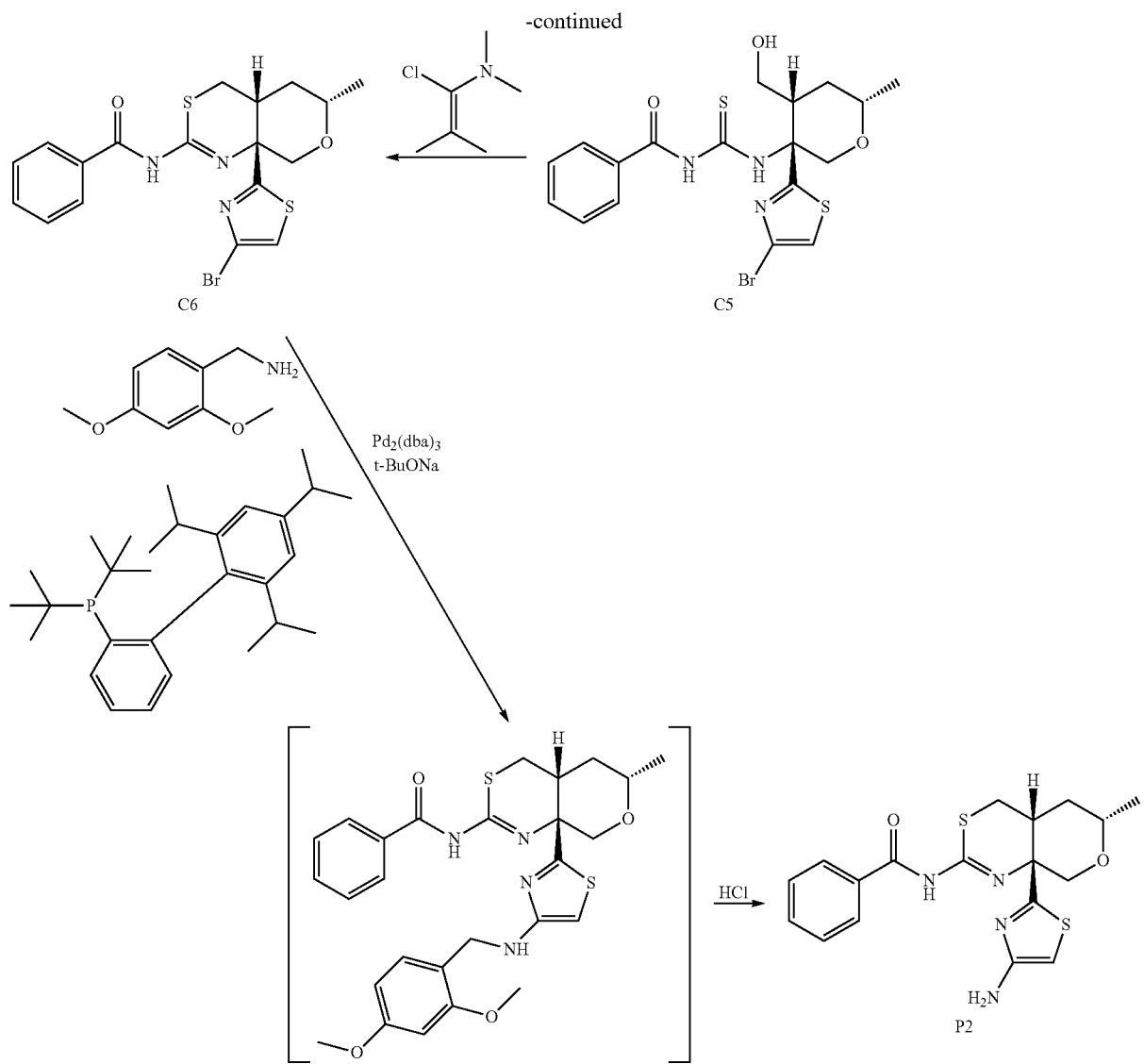

Step 1. Synthesis of (3aR,5S,7aR)-7a-(4-bromo-1,3-thiazol-2-yl)-5-methylhexahydro-1H-pyrano[3,4-c][1,2]oxazole (C3)

2,4-Dibromo-1,3-thiazole (44.7 g, 184 mmol) was dissolved in a mixture of toluene and tetrahydrofuran (10:1, 900 mL) and cooled to −78° C. To this solution was added boron trifluoride diethyl etherate (21.9 mL, 177 mmol), followed by drop-wise addition of n-butyllithium (2.5 M solution in hexanes, 68.0 mL, 170 mmol), and the reaction mixture was stirred for 30 minutes. A solution of P1 (20 g, 140 mmol) in a mixture of toluene and tetrahydrofuran (10:1, 22 mL) was then added drop-wise; the reaction temperature was maintained below −72° C. during the course of both additions. Stirring was continued for 1 hour at −78° C., whereupon the reaction was quenched via addition of saturated aqueous ammonium chloride solution. The aqueous layer was extracted three times with ethyl acetate, and the combined organic layers were washed with water and with saturated aqueous sodium chloride solution, dried over sodium sulfate, filtered, and concentrated in vacuo. Silica gel chromatography (Gradient: 0% to 100% ethyl acetate in heptane) afforded the product as a tacky amber oil. Yield: 36.34 g, 119.1 mmol, 85%. LCMS m/z 305.0, 307.0 [M+H]$^+$. $^1$H NMR (400 MHz, CDCl$_3$) δ 7.22 (s, 1H), 3.97 (AB quartet, upfield doublet is broadened, $J_{AB}$=12.6 Hz, $\Delta\nu_{AB}$=13.4 Hz, 2H), 3.67-3.76 (m, 3H), 3.38 (br ddd, J=11.8, 6.9, 4.6 Hz, 1H), 1.90 (ddd, J=14.1, 6.9, 2.1 Hz, 1H), 1.42 (ddd, J=14.1, 11.7, 11.7 Hz, 1H), 1.27 (d, J=6.2 Hz, 3H).

Step 2. Synthesis of [(2S,4R,5R)-5-amino-5-(4-bromo-1,3-thiazol-2-yl)-2-methyltetrahydro-2H-pyran-4-yl]methanol (C4)

Molybdenum hexacarbonyl (98%, 6.67 g, 24.8 mmol) was added to a solution of C3 (15.12 g, 49.54 mmol) in a mixture of acetonitrile (390 mL) and water (20 mL), and the reaction mixture was heated at reflux for 1 hour. After cooling to room temperature, the reaction mixture was chilled in an ice bath, treated portion-wise with sodium borohydride (7.50 g, 198 mmol), and allowed to stir at 0° C. for 1 hour. The mixture was then filtered through a pad of diatomaceous earth, and the pad was washed three times with dichloromethane; the organic portion of the combined filtrate and washes was washed with saturated aqueous sodium chloride solution, dried over sodium sulfate, filtered, and concentrated in vacuo. Methanol was added to the residue, then removed via concentration under reduced pressure. This methanol treatment was repeated, and the resulting residue was dissolved in dichloromethane, washed twice with 1 M aqueous sodium hydroxide solution, washed once with saturated aqueous sodium chloride solution and concentrated in vacuo, affording the product as a brown solid. Yield: 14.48 g, 47.13 mmol, 95%. LCMS m/z 307.0, 309.0 [M+H]$^+$. $^1$H NMR (400 MHz, CDCl$_3$) δ 7.22 (s, 1H), 3.79 (d, half of AB quartet, J=11.5 Hz, 1H), 3.64-3.75 (m, 3H), 3.54 (dd, half of ABX pattern, J=11.5, 4.1 Hz, 1H), 2.46-2.54 (m, 1H), 1.82-1.94 (m, 1H), 1.67-1.74 (m, 1H), 1.32 (d, J=6.2 Hz, 3H).

Step 3. Synthesis of N-{[(3R,4R,6S)-3-(4-bromo-1, 3-thiazol-2-yl)-4-(hydroxymethyl)-6-methyltetra-hydro-2H-pyran-3-yl]carbamothioyl}benzamide (C5)

Benzoyl isothiocyanate (6.92 g, 42.4 mmol) was added in a drop-wise manner to a solution of C4 (14.48 g, 47.13 mmol) in dichloromethane (420 mL), and the reaction mixture was stirred at room temperature for 24 hours. Volatiles were removed in vacuo, and the residue was purified via silica gel chromatography (Gradient: 0% to 50% ethyl acetate in heptane), providing the product as a yellow solid. Yield: 14.7 g, 31.2 mmol, 66%. $^1$H NMR (400 MHz, CDCl$_3$) δ 11.70 (br s, 1H), 8.93 (br s, 1H), 7.86-7.90 (m, 2H), 7.62-7.67 (m, 1H), 7.51-7.56 (m, 2H), 7.25 (s, 1H), 5.47 (d, J=11.9 Hz, 1H), 3.91 (d, J=12.0 Hz, 1H), 3.83 (d, J=4.4 Hz, 2H), 3.74-3.81 (m, 1H), 2.44-2.52 (m, 1H), 1.80-1.87 (m, 2H), 1.33 (d, J=6.2 Hz, 3H).

Step 4. Synthesis of N-[(4aR,6S, 8aR)-8a-(4-bromo-1,3-thiazol-2-yl)-6-methyl-4,4a,5,6,8,8a-hexahydropyrano[3,4-d][1,3]thiazin-2-yl]benzamide (C6)

1-Chloro-N,N,2-trimethylprop-1-en-1-amine (Ghosez's reagent, 7.85 mL, 59.3 mmol) was added drop-wise to a solution of C5 (9.30 g, 19.8 mmol) in dichloromethane (200 mL). After 1 hour at room temperature, the reaction mixture was partitioned between dichloromethane and saturated aqueous sodium bicarbonate solution. The organic layer was washed with saturated aqueous sodium chloride solution, dried over sodium sulfate, filtered, and concentrated in vacuo. Silica gel chromatography (Gradient: 0% to 100% ethyl acetate in heptane) provided the product as a solid. Yield: 6.90 g, 15.2 mmol, 77%. LCMS m/z 452.1, 454.1 [M+H]$^+$. $^1$H NMR (400 MHz, CDCl$_3$) δ 13.69 (br s, 1H), 8.38-8.43 (m, 2H), 7.64-7.70 (m, 1H), 7.54-7.60 (m, 2H), 7.34 (s, 1H), 4.45 (d, J=12.5 Hz, 1H), 3.93 (d, J=12.5 Hz, 1H), 3.74-3.83 (m, 1H), 3.28-3.36 (m, 1H), 3.23 (dd, J=13.5, 4.0 Hz, 1H), 2.77 (dd, J=13.5, 2.8 Hz, 1H), 1.66-1.82 (m, 2H), 1.32 (d, J=6.2 Hz, 3H).

Step 5. Synthesis of N-[(4aR,6S,8aR)-8a-(4-amino-1,3-thiazol-2-yl)-6-methyl-4,4a,5,6,8,8a-hexahydro-pyrano[3,4-d][1,3]thiazin-2-yl]benzamide (P2)

Sodium tert-butoxide (530 mg, 5.51 mmol), tris(dibenzylideneacetone)dipalladium(0) (102 mg, 0.111 mmol), and di-tert-butyl[2',4',6'-tri(propan-2-yl)biphenyl-2-yl]phosphane (141 mg, 0.332 mmol) were dissolved in degassed 1,4-dioxane (5 mL), and the reaction flask was purged with nitrogen and heated to 65° C. for 3 minutes. To this was added a solution of 1-(2,4-dimethoxyphenyl)methanamine (0.564 mL, 3.75 mmol) and C6 (1.00 g, 2.21 mmol) in 1,4-dioxane (5 mL), and the reaction mixture was heated at 95° C. for 80 minutes. It was then allowed to cool to room temperature and treated with concentrated hydrochloric acid (10 mL), whereupon it was stirred at room temperature for 1 hour. Additional concentrated hydrochloric acid (10 mL) was introduced, and the reaction was monitored until starting material had been consumed. Water (50 mL) was added, and the mixture was washed with dichloromethane (3×50 mL). The aqueous layer was poured into a 1:1 mixture of aqueous sodium hydroxide (5 M, 100 mL) and ice, and the pH was checked to ensure that it was >12. This mixture was saturated with solid sodium chloride and extracted with dichloromethane (4×100 mL); the combined organic layers were dried over magnesium sulfate and filtered. As the initial dichloromethane washes (3×50 mL) were found to contain additional material, they were concentrated to a volume of approximately 50 mL and mixed with aqueous hydrochloric acid (5 M, 50 mL). After being stirred at room temperature for 1 hour, the aqueous layer was separated and washed with dichloromethane (3×50 mL). The aqueous layer was then poured into a 1:1 mixture of aqueous sodium hydroxide (5 M, 75 mL) and ice, and the resulting mixture was saturated with solid sodium chloride and extracted with dichloromethane (3×60 mL). The combined organic layers were dried over magnesium sulfate, filtered, and added to the organic layers obtained above. This combined solution was concentrated to a volume of approximately 70 mL and washed with 5% aqueous citric acid solution, dried over magnesium sulfate, and filtered. The resulting filtrate was passed through a 0.45 μm nylon Acrodisc® to remove fine particulates, and subsequently concentrated in vacuo, affording the product as an orange solid. Yield: 608 mg, 1.56 mmol, 71%. LCMS m/z 389.1 [M+H]$^+$. $^1$H NMR (400 MHz, CDCl$_3$) δ 8.10-8.19 (br m, 2H), 7.49-7.55 (m, 1H), 7.42-7.48 (m, 2H), 5.94 (s, 1H), 3.95 (AB quartet, $J_{AB}$=12.1 Hz, $\Delta v_{AB}$=6.2 Hz, 2H), 3.77 (dqd, J=11.2, 6.1, 2.3 Hz, 1H), 3.22 (dd, J=12.9, 4.1 Hz, 1H), 2.97-3.05 (m, 1H), 2.59 (dd, J=12.9, 2.8 Hz, 1H), 1.83-1.95 (m, 1H), 1.65 (ddd, J=13.7, 4.3, 2.4 Hz, 1H), 1.29 (d, J=6.2 Hz, 3H).

Alternate Preparation of P2

N-[(4aR,6S,8aR)-8a-(4-Amino-1,3-thiazol-2-yl)-6-methyl-4,4a,5,6,8,8a-hexahydropyrano[3,4-d][1,3]thiazin-2-yl]benzamide (P2)

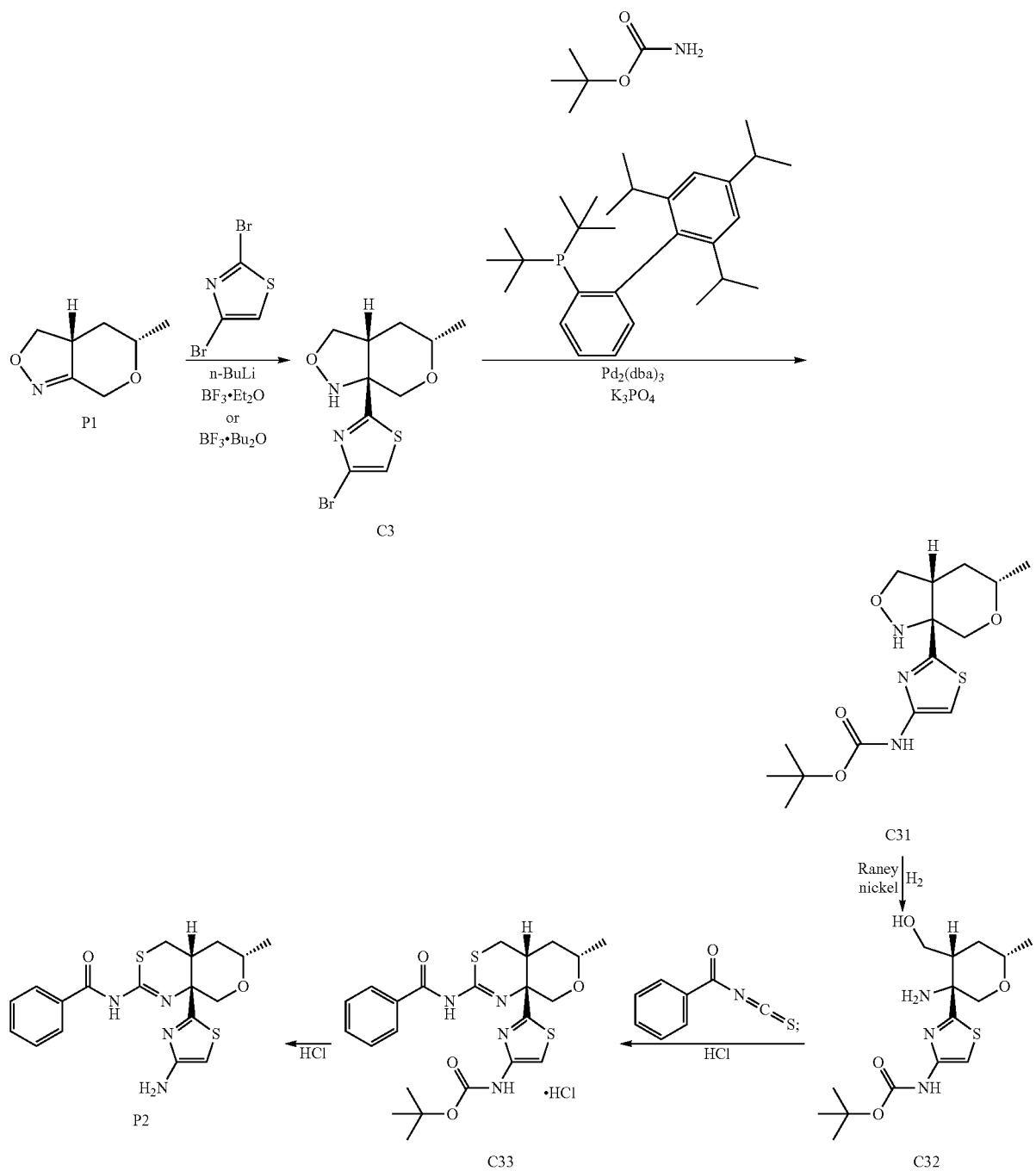

Step 1. Synthesis of (3aR,5S,7aR)-7a-(4-bromo-1,3-thiazol-2-yl)-5-methylhexahydro-1H-pyrano[3,4-c][1,2]oxazole (C3)

2,4-Dibromo-1,3-thiazole (44.8 g, 184 mmol) was dissolved in a mixture of toluene (750 mL) and tetrahydrofuran (75 mL), in a flask equipped with a mechanical stirrer. The solution was cooled to −74° C. (internal temperature) and slowly treated with boron trifluoride diethyl etherate (22 mL, 178 mmol), followed by drop-wise addition of n-butyllithium (2.5 M solution in hexanes, 68 mL, 170 mmol), at a rate such that the internal temperature of the reaction mixture did not exceed −70° C. After the additions had been completed, the reaction mixture was allowed to stir at −73° C. (internal temperature) for 30 minutes. A solution of P1 (20.0 g, 142 mmol) in a mixture of toluene (15 mL) and tetrahydrofuran (1.5 mL) was then added via cannula; the temperature was monitored during the addition, and it was observed that it increased by only 2° C. The flask that had contained P1 was washed with a mixture of toluene (11 mL) and tetrahydrofuran (1.1 mL), and this rinse was added to the reaction mixture via cannula. The reaction mixture was stirred at −74° C. (internal temperature) at approximately 500-600 rpm; within 30 minutes it became a thick gel. After it had been stirred for 1.5 hours, the reaction was quenched via addition of saturated aqueous ammonium chloride solution (300 mL) and subsequently allowed to warm to room temperature. The mixture was partitioned between water (400 mL) and ethyl acetate (300 mL); the aqueous layer was extracted with ethyl acetate (200 mL), and the combined organic layers were washed with saturated aqueous sodium chloride solution, dried over sodium sulfate, filtered, and concentrated in vacuo to provide a viscous brown oil (54 g). A portion of this material (25.5 g) was subjected to automated chromatography on silica gel (Gradient: 5% to 70% ethyl acetate in heptane), affording an a oily solid. This material was dissolved in minimal ethyl acetate (~20 mL) and treated with heptane (~400 mL); solvents were removed in vacuo, and heptane (~400 mL) was added to the residue. Concentration under reduced pressure provided the product as a yellow solid. Yield: 17.3 g, 56.7 mmol, 85% (adjusted for the fact that only a portion of the crude product was chromatographed). LCMS m/z 305.1, 307.1 [M+H]$^+$. $^1$H NMR (500 MHz, CDCl$_3$) δ 7.22 (s, 1H), 6.1-6.8 (v br s, 1H), 3.97 (AB quartet, upfield doublet is broadened, $J_{AB}$=12.7 Hz, $\Delta v_{AB}$=16.1 Hz, 2H), 3.74 (br d, half of AB quartet, J=7.5 Hz, 1H), 3.69 (dd, half of ABX pattern, J=7.5, 4.9 Hz, 1H), 3.68-3.74 (m, 1H), 3.37 (ddd, J=11.8, 6.8, 4.7 Hz, 1H), 1.89 (ddd, J=14.1, 6.9, 2.1 Hz, 1H), 1.42 (ddd, J=14.1, 11.8, 11.7 Hz, 1H), 1.26 (d, J=6.1 Hz, 3H).

Step 1. Alternate Conditions for Synthesis of (3aR, 5S,7aR)-7a-(4-bromo-1,3-thiazol-2-yl)-5-methyl-hexahydro-1H-pyrano[3,4-c][1,2]oxazole (C3)

A mixture of 2,4-dibromo-1,3-thiazole (11.85 g, 48.78 mmol) in toluene (90 mL) and chlorobenzene (90 mL) was cooled to −58° C. (internal temperature) and treated in a drop-wise manner with n-butyllithium (1.6 M solution in hexanes, 29 mL, 46 mmol), while maintaining the internal reaction temperature at −55° C. In a separate flask, a solution of P1 (5.00 g, 35.4 mmol) in toluene (25 mL) was cooled to 0° C. and slowly treated with boron trifluoride dibutyl etherate (11.0 mL, 53.2 mmol), while keeping the temperature of the solution below 5° C. The solution of P1 was then added in a drop-wise manner to the lithiated thiazole solution, while maintaining the internal reaction temperature between −54° C. and −58° C. After 10 minutes, carbon dioxide vapor (from 50 g of dry ice pellets, previously blasted with a strong nitrogen stream to remove any frost coating the pellets) was introduced to the reaction via bubbling it in under the surface of the liquid. After 20 minutes of bubbling, the reaction mixture was treated with water (5 volumes). The organic layer was washed twice with aqueous sodium carbonate solution (10%, 5 volumes), and with saturated aqueous sodium chloride solution (5 volumes). Solvent was removed under reduced pressure (50 mm mercury, bath temperature 60° C.; then 35 mm mercury, bath temperature 80° C.), and the resulting oil was treated with a solution of ethyl acetate in heptane (10%, 80 mL). Silica gel (15 g) was added, and the mixture was stirred at room temperature for 90 minutes, whereupon it was filtered; the filter cake was washed with a solution of ethyl acetate in heptane (25%, 4×30 mL), and the combined filtrates were concentrated in vacuo to a volume of ~30 mL. This material was granulated at room temperature for 4 hours. The solid was collected via filtration and washed with heptane to afford the product as a yellow solid. Yield: 8.16 g, 26.7 mmol, 75%. $^1$H NMR (400 MHz, CDCl$_3$) δ 7.22 (s, 1H), 6.43 (br s, 1H), 3.97 (AB quartet, upfield doublet is broadened, $J_{AB}$=12.6 Hz, $\Delta v_{AB}$=13.6 Hz, 2H), 3.75 (br d, half of AB quartet, J=7.5 Hz, 1H), 3.69 (dd, half of ABX pattern, J=7.4, 4.8 Hz, 1H), 3.66-3.75 (m, 1H), 3.38 (ddd, J=11.8, 6.7, 4.8 Hz, 1H), 1.89 (ddd, J=14.1, 6.9, 2.1 Hz, 1H), 1.42 (ddd, J=14.1, 11.8, 11.7 Hz, 1H), 1.27 (d, J=6.2 Hz, 3H).

Step 2. Synthesis of tert-butyl {2-[(3a R, 5S, 7aR)-5-methyltetrahydro-1H-pyrano[3,4-c][1,2]oxazol-7a(7H)-yl]-1,3-thiazol-4-yl}carbamate (C31)

Degassed toluene (48 mL) was added to a mixture of C3 (6.01 g, 19.7 mmol), tert-butyl carbamate (3.45 g, 29.4 mmol), and powdered potassium phosphate (12.6 g, 59.4 mmol), and the mixture was degassed with a stream of nitrogen. In a separate vessel, tris(dibenzylideneacetone)dipalladium(0) (97%, 1.86 g, 1.97 mmol) and di-tert-butyl [2',4',6'-tri(propan-2-yl)biphenyl-2-yl]phosphane (98%, 428 mg, 0.99 mmol) were combined with degassed toluene (6 mL) and heated at 100° C. for 2 minutes with stirring; the dark purple mixture changed to a dark maroon color during this activation. The Pd-ligand complex was added via syringe into the mixture containing C3, and the vessel was rinsed with degassed toluene (6 mL), which was also was added to the reaction mixture. The reaction mixture was heated at 100° C. for 20 hours, whereupon it was allowed to cool to room temperature and then filtered through diatomaceous earth. The filter pad was washed with ethyl acetate (2×50 mL), and the combined filtrates were concentrated in vacuo. The resulting oil was purified by chromatography on silica gel (Gradient: 5% to 80% ethyl acetate in heptane), affording the product as a fluffy yellow solid. Yield: 5.16 g, 15.1 mmol, 77%. $^1$H NMR (500 MHz, CDCl$_3$) δ 7.22-7.30 (br s, 1H, assumed; partially obscured by solvent peak), 7.12-7.21 (br s, 1H), 4.3-4.5 (v br s, 1H), 3.93 (AB quartet, downfield doublet is broadened, $J_{AB}$=12.7 Hz, $\Delta v_{AB}$=27.2 Hz, 2H), 3.73 (br d, half of AB quartet, J=7.4 Hz, 1H), 3.68 (dd, half of ABX pattern, J=7.3, 4.7 Hz, 1H), 3.63-3.7 (m, 1H), 3.24 (ddd, J=11.6, 6.8, 4.9 Hz, 1H), 1.88 (ddd, J=14.2, 6.8, 2.0 Hz, 1H), 1.52 (s, 9H), 1.42 (ddd, J=14.1, 11.7, 11.7 Hz, 1H), 1.27 (d, J=6.1 Hz, 3H).

Step 3. Synthesis of tert-butyl {2-[(3R,4R,6S)-3-amino-4-(hydroxymethyl)-6-methyltetrahydro-2H-pyran-3-yl]-1,3-thiazol-4-yl}carbamate (C32)

Compound C31 (5.0 g, 15 mmol), Raney nickel (Johnson Matthey Sponge Catalyst A5000, 1.5 g, ~25 mmol), and 2-propanol (150 mL) were combined in a hydrogenation reactor. The reactor was purged 3 times with nitrogen, and 3 times with hydrogen, whereupon the reaction mixture was hydrogenated at 50 psi for 12 hours at 50° C. The reactor was then purged with nitrogen, and the reaction mixture was filtered. The reactor and the filter cake were washed with 2-propanol (2×10 mL) and filtered through the catalyst bed. The combined filtrates were concentrated in vacuo to afford the product as an oil (5.11 g). This material can be recrystallized from toluene (3 mL/g) to provide the product as white, sugar-like crystals, however this is unnecessary for the subsequent chemistry. Yield: 5.11 g, 14.9 mmol, 99%. $^1$H NMR (400 MHz, CDCl$_3$) δ 7.31-7.43 (br s, 1H), 7.11-7.23 (br s, 1H), 3.70 (d, J=11.4 Hz, 1H), 3.69 (dd, J=11.4, 3.3 Hz, 1H), 3.62-3.7 (m, 1H), 3.50 (d, J=11.4 Hz, 1H), 3.45 (br dd, J=11.4, 3.5 Hz, 1H), 2.24-2.37 (br s, 1H), 2.16-2.24 (m, 1H), 1.82 (ddd, J=14, 13, 11 Hz, 1H), 1.70 (ddd, half of ABX pattern, J=14.1, 4.3, 2.7 Hz, 1H), 1.52 (s, 9H), 1.31 (d, J=6.2 Hz, 3H).

Alternatively, steps 2 and 3 can be carried out without isolation/purification of C31. The filtrates from step 2 may be evaporated in vacuo to provide a concentrated solution of crude C31 in toluene. After addition of 2-propanol, the Raney nickel reduction can be carried out and worked up as described in step 3. After addition of dichloromethane to the product, the mixture is adjusted to a pH of 2-3 using an aqueous solution of citric acid. The organic layer is extracted with citric acid, and the combined aqueous layers are washed twice with dichloromethane. Ethyl acetate is added to the aqueous layer, and the mixture is adjusted to a pH of 9-10 via addition of an aqueous solution of potassium carbonate. After filtration, the aqueous layer is extracted with ethyl acetate, and the combined organic layers may be concentrated in vacuo to afford C32.

Step 4. Synthesis of tert-butyl {2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}carbamate, Hydrochloride Salt (C33)

Compound C32 (from the step 3, 5.11 g, 14.9 mmol) was dissolved in ethyl acetate (50 mL). Benzoyl isothiocyanate (4.0 mL, 30 mmol) was added drop-wise via syringe over 5 minutes, and the reaction mixture was allowed to stir at room temperature for 4 hours, whereupon it was heated at reflux for 16 hours. The reaction mixture was concentrated to a volume of ~25 mL, then cooled to 0° C. and treated with concentrated hydrochloric acid (1.8 mL, 22 mmol) via drop-wise addition over 5 minutes. The resulting slurry was stirred for 30 minutes and then filtered. The filter cake consisted of the product, as a white solid. Yield: 5.63 g, 10.7 mmol, 72% yield. $^1$H NMR (400 MHz, DMSO-$d_6$) δ 10.26 (br s, 1H), 8.12-8.17 (m, 2H), 7.64 (br dd, J=7.4, 7.3 Hz, 1H), 7.54 (br dd, J=7.8, 7.3 Hz, 2H), 7.25 (br s, 1H), 4.07 (d, J=11.9 Hz, 1H), 3.80 (d, J=11.9 Hz, 1H), 3.66-3.76 (m, 1H), 2.85-2.97 (m, 3H), 1.72-1.80 (m, 1H), 1.49-1.61 (m, 1H), 1.44 (s, 9H), 1.19 (d, J=6.1 Hz, 3H).

Step 5. Synthesis of N-[(4aR,6S,8aR)-8a-(4-amino-1,3-thiazol-2-yl)-6-methyl-4,4a,5,6,8,8a-hexahydropyrano[3,4-d][1,3]thiazin-2-yl]benzamide (P2)

A mixture of C33 (5.0 g, 9.5 mmol) and toluene (20 mL) was cooled to 10° C. and treated drop-wise with concentrated hydrochloric acid (4.7 mL, 56 mmol) over 2 minutes. The reaction mixture was then allowed to warm to room temperature with rapid stirring. After 1 hour, the lower (aqueous) phase of the reaction mixture was added to a room temperature mixture of disodium hydrogen phosphate (13.5 g, 95.1 mmol) in water (100 mL) and ethyl acetate (100 mL); the aqueous phase of the resulting mixture was confirmed to be at a pH of 6-7. The organic layer was dried over magnesium sulfate, filtered, and concentrated in vacuo to a low, stirrable, volume. tert-Butyl methyl ether (15 mL) was added, and the mixture was agitated to give a slurry, which was stirred for 20 minutes; the solid was collected via filtration to afford the product as an off-white solid (2.98 g). The filtrate was concentrated under reduced pressure to provide additional product (260 mg). Combined yield: 3.24 g, 8.34 mmol, 88% yield. $^1$H NMR (400 MHz, CDCl$_3$) δ 8.06-8.22 (m, 2H), 7.49-7.55 (m, 1H), 7.41-7.48 (m, 2H), 5.94 (s, 1H), 4.03-4.13 (br s, 2H), 3.94 (AB quartet, $J_{AB}$=12.1 Hz, $\Delta v_{AB}$=6.9 Hz, 2H), 3.71-3.81 (m, 1H), 3.21 (dd, J=12.9, 4.0 Hz, 1H), 2.96-3.05 (m, 1H), 2.58 (dd, J=13.0, 2.8 Hz, 1H), 1.82-1.94 (m, 1H), 1.64 (ddd, J=13.7, 4.3, 2.3 Hz, 1H), 1.28 (d, J=6.2 Hz, 3H). The stereochemistry of P2 was confirmed through X-ray crystal structure determination of the hydrochloride salt of Example 1, described below.

Example 1

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (1)

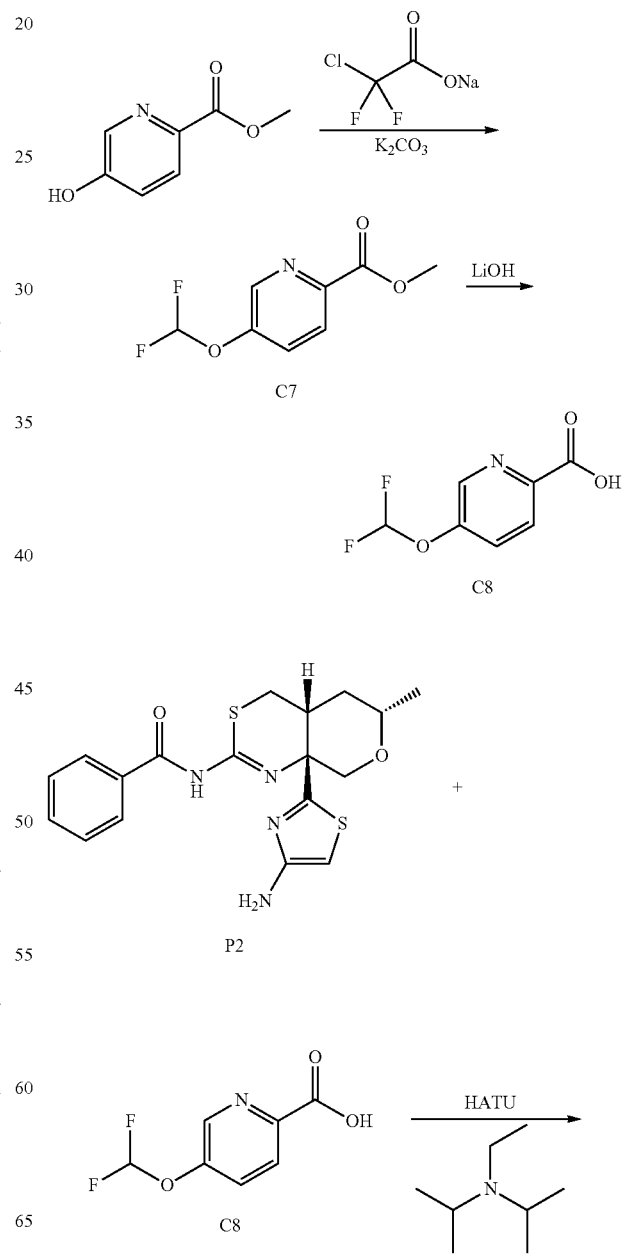

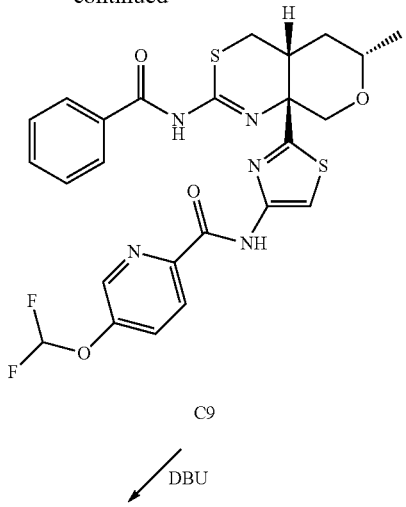

C9

↓ DBU

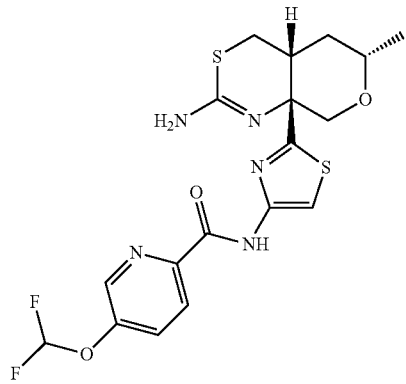

1

Step 1. Synthesis of methyl 5-(difluoromethoxy)pyridine-2-carboxylate (C7)

Potassium carbonate (45.1 g, 326 mmol) was added to a solution of methyl 5-hydroxypyridine-2-carboxylate (20 g, 130 mmol) in N,N-dimethylformamide (500 mL), and the reaction mixture was stirred at room temperature for 0.5 hours. Sodium chloro(difluoro)acetate (63.7 g, 418 mmol) was introduced, and the resulting mixture was heated at 100° C. for 5 hours, whereupon it was partitioned between saturated aqueous sodium chloride solution (300 mL) and ethyl acetate (300 mL). The aqueous layer was extracted with ethyl acetate (3×200 mL), and the combined organic layers were washed with saturated aqueous sodium chloride solution (2×200 mL), dried, filtered, and concentrated in vacuo. Silica gel chromatography (Eluent: 5:1 petroleum ether/ethyl acetate) afforded the product as a pale yellow oil. Yield: 17 g, 84 mmol, 65%. $^1$H NMR (400 MHz, CDCl$_3$) δ 8.56 (s, 1H), 8.17 (d, J=8.7 Hz, 1H), 7.59 (br d, J=8.7 Hz, 1H), 6.64 (t, $J_{HF}$=71.9 Hz, 1H), 4.00 (s, 3H).

Step 2. Synthesis of 5-(difluoromethoxy)pyridine-2-carboxylic acid (C8)

A solution of C7 (17 g, 84 mmol) in tetrahydrofuran (100 mL) and water (50 mL) was cooled to 0° C. and treated with lithium hydroxide (6.0 g, 250 mmol). After the reaction mixture had stirred at room temperature for 2 hours, it was acidified to a pH of 3 with 1 M aqueous hydrochloric acid. The aqueous layer was extracted with ethyl acetate (3×100 mL), and the combined organic layers were washed with saturated aqueous sodium chloride solution (100 mL), dried, filtered, and concentrated under reduced pressure to provide the product as a white solid. Yield: 13 g, 69 mmol, 82%. LCMS m/z 189.8 [M+H]$^+$. $^1$H NMR (400 MHz, CDCl$_3$) δ 8.52 (d, J=2.4 Hz, 1H), 8.29 (d, J=8.5 Hz, 1H), 7.73 (dd, J=8.6, 2.4 Hz, 1H), 6.68 (t, $J_{HF}$=71.5 Hz, 1H).

Step 3. Synthesis of N-{2[(4aR,6S,8aR)-2-(benzoylamino)-6-methyl-4,4a,5,6-tetrahydropyrano[3,4-d][3,4-d][1,3]thiazin-8a(8H)-yl]-1,3-thiazol-4-yl}-5-(difluoromethoxy)pyridine-2-carboxamide (C9)

To a solution of P2 (350 mg, 0.901 mmol) and C8 (204 mg, 1.08 mmol) in acetonitrile (9 mL) was added N,N-diisopropylethylamine (0.314 mL, 1.80 mmol), followed by O-7-azabenzotriazol-1-yl)-N,N,N',N'-tetramethyluronium hexafluorophosphate (HATU, 97%, 424 mg, 1.08 mmol). After the reaction mixture had stirred for 4 hours, it was partitioned between ethyl acetate (10 mL) and water (10 mL). The aqueous layer was extracted twice with ethyl acetate, and the combined organic layers were washed with saturated aqueous sodium chloride solution (50 mL), dried over sodium sulfate, filtered, and concentrated in vacuo. Silica gel chromatography (Gradient: 0% to 80% ethyl acetate in heptane) afforded the product as a solid. Yield: 410 mg, 0.733 mmol, 81%. LCMS m/z 560.3 [M+H]$^+$.

Step 4. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (1)

A solution of C9 (390 mg, 0.762 mmol) and 1,8-diazabicyclo[5.4.0]undec-7-ene (DBU, 95%, 132 μL, 0.838 mmol) in methanol (15 mL) was heated at 70° C. for 90 minutes. After removal of solvent in vacuo, the residue was purified via silica gel chromatography (Gradient: 0% to 8% methanol in dichloromethane) to provide the product as a solid. Yield: 191 mg, 0.419 mmol, 55%. LCMS m/z 456.2 [M+H]$^+$. $^1$H NMR (400 MHz, CDCl$_3$) δ 10.40 (br s, 1H), 8.48 (br dd, J=2.7, 0.6 Hz, 1H), 8.31 (dd, J=8.6, 0.6 Hz, 1H), 7.72 (s, 1H), 7.68 (ddt, J=8.6, 2.7, 0.7 Hz, 1H), 6.65 (t, $J_{HF}$=72.0 Hz, 1H), 3.93 (AB quartet, downfield doublet is broadened, $J_{AB}$=11.2 Hz, $\Delta v_{AB}$=45.8 Hz, 2H), 3.75 (dqd, J=11.2, 6.1, 2.3 Hz, 1H), 3.19 (dd, J=12.6, 4.0 Hz, 1H), 2.83-2.90 (m, 1H), 2.61 (dd, J=12.6, 2.8 Hz, 1H), 1.81 (ddd, J=13.2, 12.9, 11.4 Hz, 1H), 1.56 (ddd, J=13.4, 4.2, 2.3 Hz, 1H), 1.30 (d, J=6.1 Hz, 3H).

Alternate Synthesis of Example 1, Hydrochloride Salt

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide, Hydrochloride Salt (1·HCl)

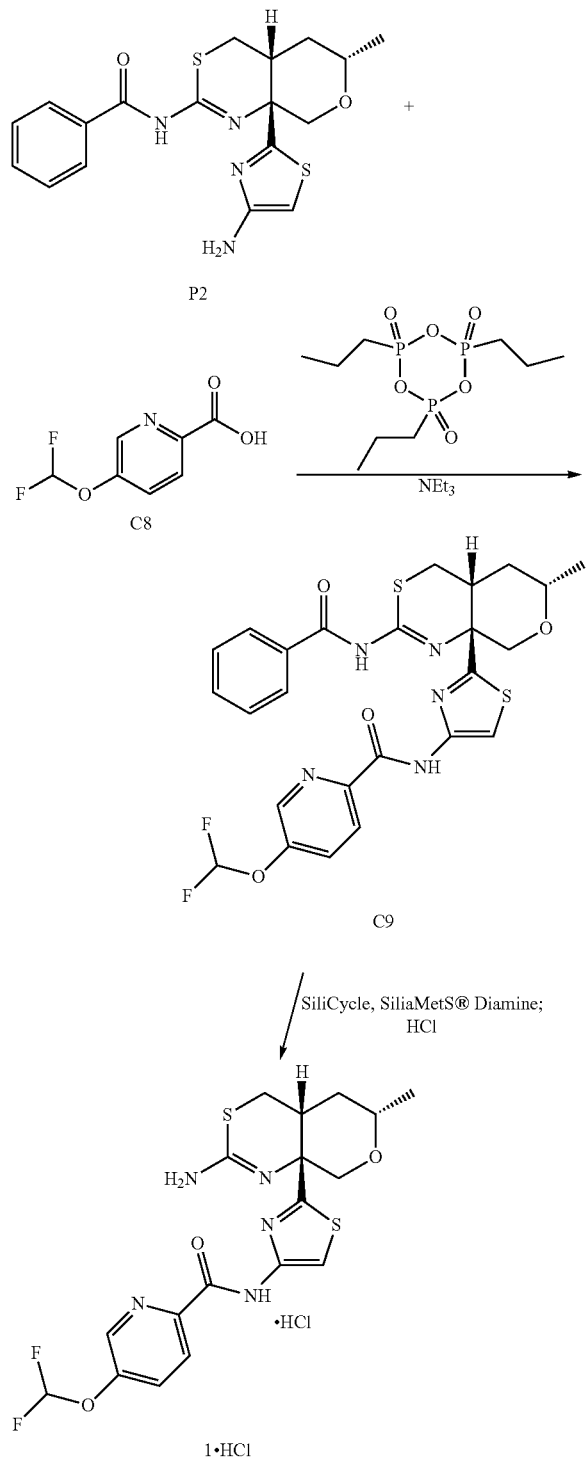

Step 1. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (C9)

2,4,6-Tripropyl-1,3,5,2,4,6-trioxatriphosphinane 2,4,6-trioxide (50% solution by weight in ethyl acetate, 19.2 mL, 32.2 mmol) was added over 5 minutes to an ice-cooled mixture of C8 (2.51 g, 13.3 mmol), P2 (5.00 g, 12.9 mmol), and triethylamine (7.2 mL, 52 mmol) in ethyl acetate (28 mL), while the reaction temperature was maintained between 0° C. and 5° C. After 45 minutes of stirring at 20° C. to 25° C., the reaction mixture was diluted with dichloromethane (50 mL), then quenched via addition of aqueous hydrochloric acid (1 M, 50 mL). The resulting mixture was washed with an aqueous solution of triethylamine (1 M, 50 mL). The organic layer was atmospherically displaced with 2-propanol to a final volume of ~75 mL, which consisted of product and 2-propanol. This slurry was cooled to 0° C. to 5° C. and granulated for 30 minutes; the solid was collected via filtration and washed with cold 2-propanol, affording the product as a solid. Yield: 5.75 g, 10.3 mmol, 80%. $^1$H NMR (400 MHz, DMSO-$d_6$) δ 8.62 (d, J=2.7 Hz, 1H), 8.23 (d, J=8.7 Hz, 1H), 7.94-8.19 (v br m, 2H), 7.92 (dd, J=8.8, 2.7 Hz, 1H), 7.73-7.79 (br s, 1H), 7.5-7.6 (br s, 1H), 7.49 (t, $J_{HF}$=72.8 Hz, 1H), 7.45-7.51 (m, 2H), 4.06-4.21 (v br s, 1H), 3.82 (br d, J=11.6 Hz, 1H), 3.69-3.8 (v br m, 1H), 2.85-3.06 (br m, 2H), 2.69-2.80 (br m, 1H), 1.67-1.79 (br m, 1H), 1.53-1.66 (m, 1H), 1.19 (d, J=6.0 Hz, 3H).

Step 2. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide, Hydrochloride Salt (1·HCl)

SiliCycle, SiliaMetS® Diamine (4.72 g, 5.36 mmol) was added to a solution of C9 (1.00 g, 1.79 mmol) in toluene (10 mL), and the reaction mixture was heated at reflux overnight. After being cooled to 35° C., the reaction mixture was diluted with dichloromethane (10 mL), stirred for 10 minutes at 35° C., and filtered through diatomaceous earth to remove the SiliCycle reagent. The filter pad was rinsed with dichloromethane and the combined filtrates were heated to reflux and displaced with isopropyl acetate (4×10 mL) to a final volume of 15 mL. This mixture was heated to 50° C., treated with concentrated hydrochloric acid (0.17 mL, 2.0 mmol), and subsequently cooled to 0° C. to 5° C. and allowed to granulate for 1 hour. The solid was collected via filtration and washed with cold propan-2-yl acetate to afford the product as a solid. This material was crystalline by powder X-ray diffraction analysis. Yield: 0.67 g, 1.4 mmol, 78%. $^1$H NMR (400 MHz, DMSO-$d_6$) δ 11.30 (br s, 1H), 10.73 (s, 1H), 9.6-9.9 (v br s, 1H), 8.6-8.9 (v br s, 1H), 8.63 (d, J=2.7 Hz, 1H), 8.24 (d, J=8.6 Hz, 1H), 7.93 (dd, J=8.7, 2.8 Hz, 1H), 7.84 (s, 1H), 7.51 (t, $J_{HF}$=72.8 Hz, 1H), 3.96 (AB quartet, $J_{AB}$=12.2 Hz, $\Delta\nu_{AB}$=62.6 Hz, 2H), 3.75-3.85 (m, 1H), 3.02-3.11 (m, 3H), 1.73-1.82 (m, 1H), 1.39-1.52 (m, 1H), 1.21 (d, J=6.2 Hz, 3H).

Alternate Generation of Crystalline Example 1, Hydrochloride Salt

A sample of Example 1 (224 mg, 0.492 mmol) was dissolved in ethyl acetate (1 mL) at 60° C. Hydrogen chloride (2 M in diethyl ether, 0.49 mL, 0.98 mmol) was added, and the slurry was allowed to cool to room temperature with stirring. Solvents were removed in vacuo, and the residue was dissolved in hot ethanol. The resulting solution was allowed to cool to room temperature and stand for 3 days; single crystals were observed, one of which was subjected to the X-ray crystal structure determination described below. This confirmed the indicated stereochemistry of the hydrochloride salt of Example 1. The ethanol was blown down to a minimum, and the solid was collected via filtration. This sample was crystalline by powder X-ray diffraction analysis. Yield: 200 mg, 0.41 mmol, 83%.

Single Crystal X-Ray Analysis of 1.HCl

Data collection was performed on a Bruker APEX diffractometer at room temperature. Data collection consisted of omega and phi scans.

The structure was solved by direct methods using SHELX software suite in the space group $P2_12_12_1$. The structure was subsequently refined by the full-matrix least squares method. All non-hydrogen atoms were found and refined using anisotropic displacement parameters.

The asymmetric unit is comprised of one ionized molecule of the compound of Example 1 and one chloride ion.

The hydrogen atoms located on nitrogen and oxygen were found from the Fourier difference map and refined freely. The remaining hydrogen atoms were placed in calculated positions and were allowed to ride on their carrier atoms. The final refinement included isotropic displacement parameters for all hydrogen atoms.

The final R-index was 5.8%. A final difference Fourier revealed no missing or misplaced electron density.

Pertinent crystal, data collection and refinement information is summarized in Table XR4. Atomic coordinates, bond lengths, bond angles, torsion angles and displacement parameters are listed in Tables XR5-XR8.
Software and References
SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE XR4

Crystal data and structure refinement for 1•HCl.

| | |
|---|---|
| Empirical formula | $C_{18}H_{19}F_2N_5O_3S_2$•HCl |
| Formula weight | 455.50 · 36.46 |
| Temperature | 296(2)K |
| Wavelength | 1.54178 Å |
| Crystal system | Orthorhombic |
| Space group | $P2_12_12_1$ |
| Unit cell dimensions | a = 9.892(2) Å α = 90°. |
| | b = 12.732(3) Å β = 90°. |
| | c = 17.334(4) Å γ = 90°. |
| Volume | 2183.0(8) Å$^3$ |
| Z | 4 |
| Density (calculated) | 1.497 Mg/m$^3$ |
| Absorption coefficient | 3.772 mm$^{-1}$ |
| F(000) | 1016 |
| Crystal size | 0.32 × 0.24 × 0.18 mm$^3$ |
| Theta range for data collection | 4.31 to 65.54° |
| Index ranges | −11 <= h <= 11, |
| | −12 <= k <= 14, |
| | −20 <= l <= 18 |
| Reflections collected | 9650 |
| Independent reflections | 3555 [R(int) = 0.0541] |
| Completeness to theta = 65.54° | 97.7% |
| Absorption correction | Empirical |
| Max. and min. transmission | 0.5500 and 0.3782 |
| Refinement method | Full-matrix least-squares on $F^2$ |
| Data/restraints/parameters | 3555/0/295 |
| Goodness-of-fit on $F^2$ | 1.006 |
| Final R indices [I > 2sigma(I)] | R1 = 0.0580, wR2 = 0.1512 |
| R indices (all data) | R1 = 0.0651, wR2 = 0.1578 |
| Absolute structure parameter | 0.09(3) |
| Largest diff. peak and hole | 0.424 and −0.339 e · Å$^{-3}$ |

TABLE XR5

Atomic coordinates (×10$^4$) and equivalent isotropic displacement parameters (Å$^2$ × 10$^3$) for 1•HCl. U(eq) is defined as one third of the trace of the orthogonalized $U^{ij}$ tensor.

| | x | y | z | U(eq) |
|---|---|---|---|---|
| C(1) | 3319(5) | −1085(4) | 2293(2) | 47(1) |
| C(2) | 5226(5) | −682(4) | 3068(2) | 49(1) |
| C(3) | 5839(5) | −16(4) | 2430(2) | 46(1) |
| C(4) | 4759(4) | 449(3) | 1895(2) | 40(1) |
| C(5) | 3796(4) | −406(3) | 1613(2) | 37(1) |
| C(6) | 5465(4) | −900(3) | 592(2) | 39(1) |
| C(7) | 5342(5) | 1071(3) | 1227(3) | 46(1) |
| C(8) | 2518(4) | 81(3) | 1264(2) | 38(1) |
| C(9) | 915(5) | 1231(4) | 1070(3) | 49(1) |
| C(10) | 357(5) | 431(4) | 686(3) | 48(1) |
| C(11) | −677(5) | 2697(4) | 907(3) | 48(1) |
| C(12) | −801(5) | 3842(4) | 1114(3) | 49(1) |
| C(13) | 150(5) | 4228(4) | 1585(3) | 55(1) |
| C(14) | 97(6) | 5228(5) | 1781(4) | 80(2) |
| C(15) | −909(6) | 5888(4) | 1532(3) | 58(1) |
| C(16) | −1904(6) | 5495(4) | 1055(3) | 57(1) |
| C(17) | −1632(7) | 7640(5) | 1499(4) | 77(2) |
| C(18) | 6263(6) | −1207(5) | 3564(3) | 62(1) |
| N(1) | 4435(3) | −1105(3) | 1050(2) | 39(1) |
| N(2) | 2153(4) | 1036(3) | 1403(2) | 54(1) |
| N(3) | 443(5) | 2251(4) | 1176(4) | 74(2) |
| N(4) | −1847(5) | 4439(4) | 839(3) | 70(1) |
| N(5) | 5894(5) | −1649(4) | 128(2) | 53(1) |
| O(1) | 4415(3) | −1501(3) | 2725(2) | 51(1) |
| O(2) | −1506(4) | 2234(3) | 522(2) | 73(1) |
| O(3) | −826(5) | 6902(3) | 1806(2) | 75(1) |
| S(1) | 6321(1) | 282(1) | 555(1) | 53(1) |
| S(2) | 1376(1) | −642(1) | 733(1) | 48(1) |
| F(1) | −1269(5) | 8550(3) | 1766(3) | 99(1) |
| F(2) | −2938(4) | 7479(3) | 1740(2) | 90(1) |
| Cl(1) | 3806(1) | 6554(1) | 619(1) | 59(1) |

TABLE XR6

Bond lengths [Å] and angles [°] for 1•HCl.

| | |
|---|---|
| C(1)—O(1) | 1.420(5) |
| C(1)—C(5) | 1.537(6) |
| C(1)—H(1A) | 0.9700 |
| C(1)—H(1B) | 0.9700 |
| C(2)—O(1) | 1.444(6) |
| C(2)—C(18) | 1.496(7) |
| C(2)—C(3) | 1.520(7) |
| C(2)—H(2) | 0.9800 |
| C(3)—C(4) | 1.533(6) |
| C(3)—H(3A) | 0.9700 |
| C(3)—H(3B) | 0.9700 |
| C(4)—C(7) | 1.517(6) |
| C(4)—C(5) | 1.528(6) |
| C(4)—H(4) | 0.9800 |
| C(5)—N(1) | 1.463(6) |
| C(5)—C(8) | 1.532(6) |
| C(6)—N(5) | 1.316(6) |
| C(6)—N(1) | 1.318(5) |
| C(6)—S(1) | 1.728(4) |

TABLE XR6-continued

Bond lengths [Å] and angles [°] for 1•HCl.

| | |
|---|---|
| C(7)—S(1) | 1.816(5) |
| C(7)—H(7A) | 0.9700 |
| C(7)—H(7B) | 0.9700 |
| C(8)—N(2) | 1.290(6) |
| C(8)—S(2) | 1.723(4) |
| C(9)—C(10) | 1.336(6) |
| C(9)—N(2) | 1.377(6) |
| C(9)—N(3) | 1.392(7) |
| C(10)—S(2) | 1.699(5) |
| C(10)—H(10) | 0.9300 |
| C(11)—O(2) | 1.210(6) |
| C(11)—N(3) | 1.330(7) |
| C(11)—C(12) | 1.506(7) |
| C(12)—C(13) | 1.339(7) |
| C(12)—N(4) | 1.369(7) |
| C(13)—C(14) | 1.319(8) |
| C(13)—H(13) | 0.9300 |
| C(14)—C(15) | 1.372(8) |
| C(14)—H(14) | 0.9300 |
| C(15)—O(3) | 1.378(7) |
| C(15)—C(16) | 1.379(7) |
| C(16)—N(4) | 1.397(7) |
| C(16)—H(16) | 0.9300 |
| C(17)—F(1) | 1.298(7) |
| C(17)—O(3) | 1.342(7) |
| C(17)—F(2) | 1.372(8) |
| C(17)—H(17) | 0.9800 |
| C(18)—H(18A) | 0.9600 |
| C(18)—H(18B) | 0.9600 |
| C(18)—H(18C) | 0.9600 |
| N(1)—H(1D) | 1.04(5) |
| N(3)—H(3D) | 0.67(6) |
| N(5)—H(5A) | 0.95(6) |
| N(5)—H(5B) | 0.87(6) |
| O(1)—C(1)—C(5) | 112.3(3) |
| O(1)—C(1)—H(1A) | 109.1 |
| C(5)—C(1)—H(1A) | 109.1 |
| O(1)—C(1)—H(1B) | 109.1 |
| C(5)—C(1)—H(1B) | 109.1 |
| H(1A)—C(1)—H(1B) | 107.9 |
| O(1)—C(2)—C(18) | 107.2(4) |
| O(1)—C(2)—C(3) | 109.0(3) |
| C(18)—C(2)—C(3) | 113.2(4) |
| O(1)—C(2)—H(2) | 109.1 |
| C(18)—C(2)—H(2) | 109.1 |
| C(3)—C(2)—H(2) | 109.1 |
| C(2)—C(3)—C(4) | 112.1(4) |
| C(2)—C(3)—H(3A) | 109.2 |
| C(4)—C(3)—H(3A) | 109.2 |
| C(2)—C(3)—H(3B) | 109.2 |
| C(4)—C(3)—H(3B) | 109.2 |
| H(3A)—C(3)—H(3B) | 107.9 |
| C(7)—C(4)—C(5) | 111.3(3) |
| C(7)—C(4)—C(3) | 113.5(4) |
| C(5)—C(4)—C(3) | 110.7(4) |
| C(7)—C(4)—H(4) | 107.0 |
| C(5)—C(4)—H(4) | 107.0 |
| C(3)—C(4)—H(4) | 107.0 |
| N(1)—C(5)—C(4) | 112.2(3) |
| N(1)—C(5)—C(8) | 109.9(3) |
| C(4)—C(5)—C(8) | 110.6(3) |
| N(1)—C(5)—C(1) | 107.6(3) |
| C(4)—C(5)—C(1) | 110.3(3) |
| C(8)—C(5)—C(1) | 106.1(3) |
| N(5)—C(6)—N(1) | 118.3(4) |
| N(5)—C(6)—S(1) | 116.8(4) |
| N(1)—C(6)—S(1) | 124.9(3) |
| C(4)—C(7)—S(1) | 113.8(3) |
| C(4)—C(7)—H(7A) | 108.8 |
| S(1)—C(7)—H(7A) | 108.8 |
| C(4)—C(7)—H(7B) | 108.8 |
| S(1)—C(7)—H(7B) | 108.8 |
| H(7A)—C(7)—H(7B) | 107.7 |
| N(2)—C(8)—C(5) | 122.6(4) |
| N(2)—C(8)—S(2) | 114.8(3) |
| C(5)—C(8)—S(2) | 122.3(4) |
| C(10)—C(9)—N(2) | 116.0(4) |
| C(10)—C(9)—N(3) | 129.7(5) |
| N(2)—C(9)—N(3) | 114.3(4) |
| C(9)—C(10)—S(2) | 110.1(3) |
| C(9)—C(10)—H(10) | 125.0 |
| S(2)—C(10)—H(10) | 125.0 |
| O(2)—C(11)—N(3) | 123.4(5) |
| O(2)—C(11)—C(12) | 123.2(4) |
| N(3)—C(11)—C(12) | 113.4(4) |
| C(13)—C(12)—N(4) | 122.6(5) |
| C(13)—C(12)—C(11) | 116.3(4) |
| N(4)—C(12)—C(11) | 121.0(5) |
| C(14)—C(13)—C(12) | 118.9(5) |
| C(14)—C(13)—H(13) | 120.6 |
| C(12)—C(13)—H(13) | 120.6 |
| C(13)—C(14)—C(15) | 122.6(5) |
| C(13)—C(14)—H(14) | 118.7 |
| C(15)—C(14)—H(14) | 118.7 |
| C(14)—C(15)—O(3) | 115.0(5) |
| C(14)—C(15)—C(16) | 118.9(5) |
| O(3)—C(15)—C(16) | 126.1(5) |
| C(15)—C(16)—N(4) | 118.8(5) |
| C(15)—C(16)—H(16) | 120.6 |
| N(4)—C(16)—H(16) | 120.6 |
| F(1)—C(17)—O(3) | 108.6(6) |
| F(1)—C(17)—F(2) | 106.6(5) |
| O(3)—C(17)—F(2) | 109.5(5) |
| F(1)—C(17)—H(17) | 110.6 |
| O(3)—C(17)—H(17) | 110.6 |
| F(2)—C(17)—H(17) | 110.6 |
| C(2)—C(18)—H(18A) | 109.5 |
| C(2)—C(18)—H(18B) | 109.5 |
| H(18A)—C(18)—H(18B) | 109.5 |
| C(2)—C(18)—H(18C) | 109.5 |
| H(18A)—C(18)—H(18C) | 109.5 |
| H(18B)—C(18)—H(18C) | 109.5 |
| C(6)—N(1)—C(5) | 128.0(4) |
| C(6)—N(1)—H(1D) | 120(3) |
| C(5)—N(1)—H(1D) | 112(3) |
| C(8)—N(2)—C(9) | 109.9(4) |
| C(11)—N(3)—C(9) | 129.2(5) |
| C(11)—N(3)—H(3D) | 105(5) |
| C(9)—N(3)—H(3D) | 126(5) |
| C(12)—N(4)—C(16) | 118.1(5) |
| C(6)—N(5)—H(5A) | 117(3) |
| C(6)—N(5)—H(5B) | 115(4) |
| H(5A)—N(5)—H(5B) | 126(5) |
| C(1)—O(1)—C(2) | 111.8(4) |
| C(17)—O(3)—C(15) | 119.0(5) |
| C(6)—S(1)—C(7) | 101.4(2) |
| C(10)—S(2)—C(8) | 89.2(2) |

Symmetry Transformations Used to Generate Equivalent Atoms.

TABLE XR7

Anisotropic displacement parameters (Å² × 10³) for 1•HCl. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(1) | 41(2) | 54(3) | 45(2) | 1(2) | −2(2) | −4(2) |
| C(2) | 50(3) | 52(3) | 45(2) | −10(2) | −7(2) | 6(2) |
| C(3) | 43(2) | 47(3) | 49(2) | −12(2) | −7(2) | 3(2) |
| C(4) | 39(2) | 38(2) | 44(2) | −10(2) | −1(2) | 1(2) |
| C(5) | 38(2) | 31(2) | 42(2) | −6(2) | −2(2) | 2(2) |
| C(6) | 36(2) | 45(2) | 38(2) | −2(2) | −5(2) | 0(2) |
| C(7) | 45(3) | 34(2) | 58(2) | 0(2) | −4(2) | 0(2) |
| C(8) | 32(2) | 36(2) | 45(2) | −6(2) | −1(2) | −4(2) |
| C(9) | 43(3) | 46(3) | 58(2) | −7(2) | −10(2) | 6(2) |
| C(10) | 39(2) | 53(3) | 52(2) | −5(2) | −5(2) | 4(2) |
| C(11) | 38(2) | 55(3) | 50(2) | −2(2) | −4(2) | 6(2) |
| C(12) | 47(3) | 52(3) | 49(2) | 1(2) | 1(2) | 14(2) |
| C(13) | 42(3) | 40(3) | 84(3) | −15(2) | −25(2) | 16(2) |
| C(14) | 58(4) | 77(4) | 105(4) | −23(4) | −27(3) | 13(3) |
| C(15) | 60(3) | 55(3) | 59(3) | 5(2) | 6(2) | 8(3) |

TABLE XR7-continued

Anisotropic displacement parameters (Å² × 10³) for 1•HCl. The anisotropic displacement factor exponent takes the form: $-2\pi^2[h^2 a^{*2}U^{11} + \ldots + 2 h k a^* b^* U^{12}]$.

|  | $U^{11}$ | $U^{22}$ | $U^{33}$ | $U^{23}$ | $U^{13}$ | $U^{12}$ |
|---|---|---|---|---|---|---|
| C(16) | 71(3) | 52(3) | 47(2) | 3(2) | 1(2) | 21(3) |
| C(17) | 98(5) | 49(3) | 83(4) | 0(3) | 22(4) | 4(3) |
| C(18) | 67(3) | 66(3) | 55(3) | −1(2) | −18(3) | 10(3) |
| N(1) | 33(2) | 37(2) | 48(2) | −8(2) | 2(2) | −1(2) |
| N(2) | 45(2) | 52(2) | 66(2) | −15(2) | −16(2) | 13(2) |
| N(3) | 62(3) | 53(3) | 108(4) | −30(3) | −37(3) | 18(3) |
| N(4) | 72(3) | 78(3) | 62(2) | 11(2) | 4(2) | 13(3) |
| N(5) | 47(2) | 61(3) | 51(2) | −11(2) | 7(2) | 6(2) |
| O(1) | 53(2) | 50(2) | 50(2) | 3(1) | −9(2) | 4(2) |
| O(2) | 60(2) | 70(2) | 91(2) | −19(2) | −27(2) | 16(2) |
| O(3) | 85(3) | 54(2) | 87(3) | −6(2) | −11(2) | 12(2) |
| S(1) | 50(1) | 55(1) | 56(1) | 2(1) | 10(1) | −7(1) |
| S(2) | 41(1) | 44(1) | 58(1) | −11(1) | −6(1) | 0(1) |
| F(1) | 110(3) | 59(2) | 127(3) | −5(2) | 17(3) | 11(2) |
| F(2) | 76(2) | 89(3) | 107(3) | −6(2) | 25(2) | 19(2) |
| Cl(1) | 62(1) | 47(1) | 68(1) | −10(1) | −13(1) | −4(1) |

TABLE XR8

Hydrogen coordinates (×10⁴) and isotropic displacement parameters (Å² × 10³) for 1•HCl.

|  | x | y | z | U(eq) |
|---|---|---|---|---|
| H(1A) | 2755 | −663 | 2631 | 56 |
| H(1B) | 2772 | −1659 | 2099 | 56 |
| H(2) | 4648 | −239 | 3392 | 59 |
| H(3A) | 6454 | −445 | 2128 | 55 |
| H(3B) | 6358 | 550 | 2659 | 55 |
| H(4) | 4223 | 940 | 2205 | 49 |
| H(7A) | 5916 | 1623 | 1430 | 55 |
| H(7B) | 4607 | 1403 | 948 | 55 |
| H(10) | −469 | 457 | 430 | 57 |
| H(13) | 837 | 3798 | 1770 | 66 |
| H(14) | 768 | 5496 | 2101 | 96 |
| H(16) | −2600 | 5925 | 881 | 68 |
| H(17) | −1578 | 7630 | 935 | 92 |
| H(18A) | 5830 | −1512 | 4006 | 94 |
| H(18B) | 6917 | −699 | 3730 | 94 |
| H(18C) | 6707 | −1749 | 3273 | 94 |
| H(1D) | 3960(50) | −1830(40) | 1030(30) | 50(13) |
| H(3D) | 710(60) | 2610(50) | 1420(30) | 54(18) |
| H(5A) | 5520(60) | −2330(50) | 200(30) | 63 |
| H(5B) | 6620(60) | −1500(50) | −130(30) | 63 |

Example 2

N-{2-[(4a R, 6S, 8a R)-2-Amino-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide (2)

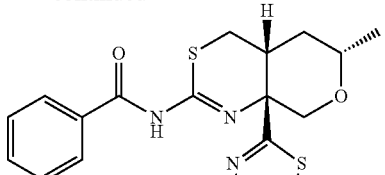

C12

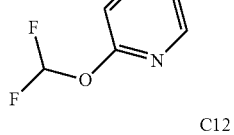

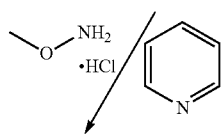

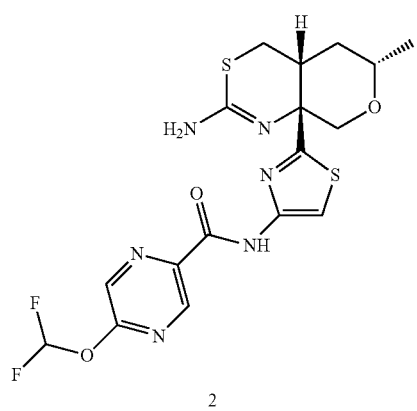 [SMILES: C[C@H]1C[C@H]2CSC(N)=N[C@@]2(c2nc(NC(=O)c3cnc(OC(F)F)cn3)cs2)CO1 ; "2"]

2

Step 1. Synthesis of methyl
5-(difluoromethoxy)pyrazine-2-carboxylate (C10)

To a solution of methyl 5-hydroxypyrazine-2-carboxylate (9.25 g, 60.0 mmol) in N,N-dimethylformamide (120 mL) were added potassium carbonate (24.8 g, 179 mmol) and sodium chloro(difluoro)acetate (18.3 g, 120 mmol). The mixture was heated to 100° C. for 15 minutes, whereupon it was filtered, and the filter cake was washed with ethyl acetate (2×50 mL). The combined filtrates were poured into saturated aqueous ammonium chloride solution (200 mL) and extracted with ethyl acetate (3×200 mL); the combined organic layers were washed sequentially with saturated aqueous sodium bicarbonate solution (2×300 mL) and with saturated aqueous sodium chloride solution (2×300 mL), dried, filtered, and concentrated in vacuo. Chromatography on silica gel (Gradient: 0% to 15% ethyl acetate in petroleum ether) afforded the product as a yellow solid. Yield: 1.7 g, 8.3 mmol, 14%. $^1$H NMR (400 MHz, CDCl$_3$) δ 8.92 (d, J=1.2 Hz, 1H), 8.47 (d, J=1.2 Hz, 1H), 7.49 (t, $J_{HF}$=71.3 Hz, 1H), 4.04 (s, 3H).

Step 2. Synthesis of
5-(difluoromethoxy)pyrazine-2-carboxylic acid
(C11)

Aqueous sodium hydroxide solution (5 M, 4.10 mL, 20.5 mmol) was added to a solution of C10 (2.10 g, 10.3 mmol) in tetrahydrofuran (25 mL) and water (12 mL). The reaction mixture was stirred at room temperature for 5 minutes, whereupon it was treated with aqueous hydrochloric acid (2 M, 11 mL). The mixture was extracted with ethyl acetate (2×150 mL), and the combined organic layers were washed with saturated aqueous sodium chloride solution (2×100 mL), dried, filtered, and concentrated under reduced pressure to provide the product as a yellow solid. Yield: 1.8 g, 9.5 mmol, 92%. LCMS m/z 189.0 [M−H$^+$]. $^1$H NMR (400 MHz, CDCl$_3$) δ 9.05 (d, J=1.3 Hz, 1H), 8.43 (d, J=1.4 Hz, 1H), 7.52 (t, $J_{HF}$=71.0 Hz, 1H).

Step 3. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide (C2)

Compound P2 was reacted with C11 using the method described for synthesis of C9 in Example 1. The product was isolated as a solid. Yield: 65 mg, 0.12 mmol, 52%. LCMS m/z 561.3 [M+H]$^+$.

Step 4. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide (2)

Pyridine (0.96 mL, 12 mmol) and methoxylamine hydrochloride (96.9 mg, 1.16 mmol) were added to a solution of C12 (65 mg, 0.12 mmol) in ethanol (1.2 mL). The reaction mixture was stirred at 50° C. for 5 hours, whereupon it was cooled to room temperature and concentrated in vacuo. The residue was diluted with dichloromethane and washed sequentially with aqueous sodium bicarbonate solution (3 times), with water, and with saturated aqueous sodium chloride solution. After being dried over sodium sulfate and filtered, the solution was concentrated under reduced pressure and purified via silica gel chromatography (Gradient: 0% to 4% methanol in dichloromethane) to provide the product as a solid. Yield: 41 mg, 90 μmol, 75%. LCMS m/z 457.1 [M+H]$^+$. $^1$H NMR (400 MHz, CDCl$_3$) δ 10.09 (br s, 1H), 9.06 (d, J=1.3 Hz, 1H), 8.34 (d, J=1.3 Hz, 1H), 7.71 (s, 1H), 7.51 (t, $J_{HF}$=71.4 Hz, 1H), 3.89 (AB quartet, $J_{AB}$=11.1 Hz, $Δv_{AB}$=40.8 Hz, 2H), 3.73 (dqd, J=11.2, 6.1, 2.2 Hz, 1H), 3.16 (dd, J=12.5, 4.0 Hz, 1H), 2.77-2.84 (m, 1H), 2.58 (dd, J=12.5, 2.8 Hz, 1H), 1.80 (ddd, J=13.1, 12.9, 11.4 Hz, 1H), 1.53 (ddd, J=13.4, 4.2, 2.3 Hz, 1H), 1.28 (d, J=6.1 Hz, 3H).

Example 3
N-{2-[(4aR,6S, 8a R)-2-Amino-6-methyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide (3)
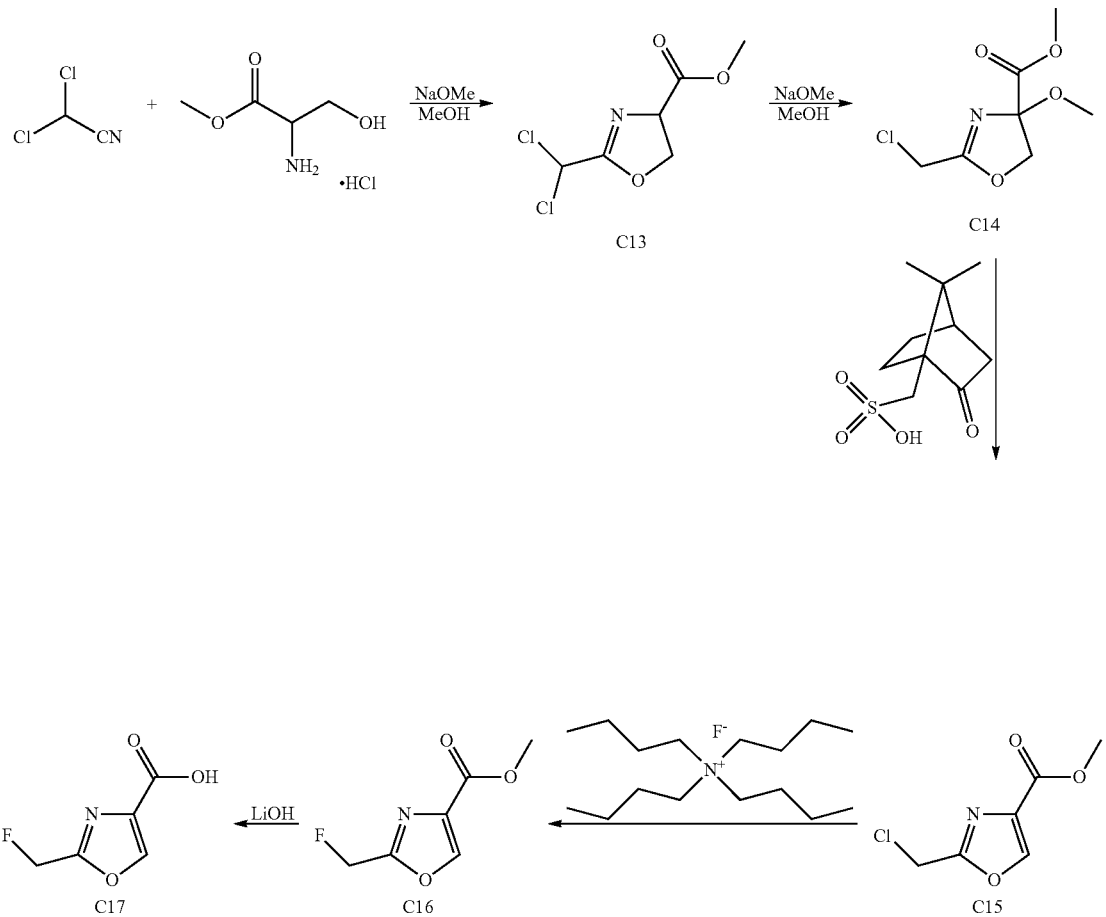
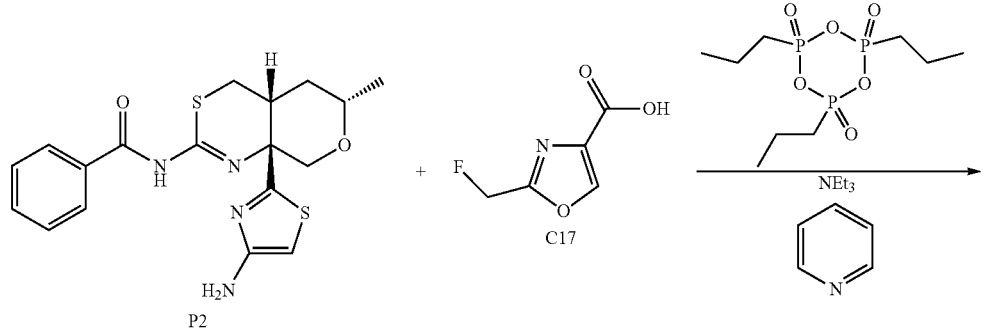

-continued

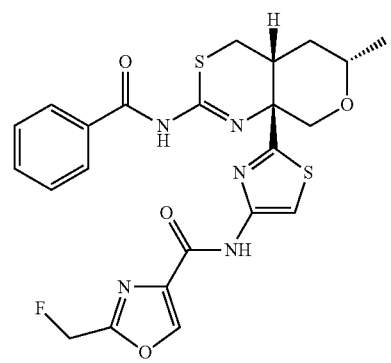

C18

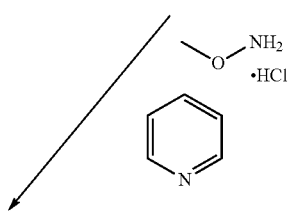

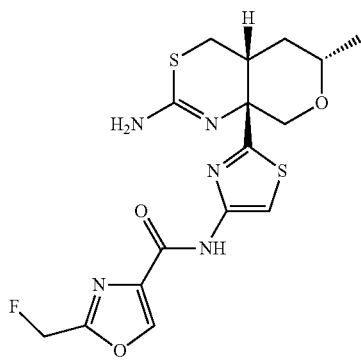

3

Step 1. Synthesis of methyl 2-(dichloromethyl)-4,5-dihydro-1,3-oxazole-4-carboxylate (C13)

A solution of dichloroacetonitrile (215 g, 1.96 mol) in methanol (200 mL) was added drop-wise to a −5° C. solution of sodium methoxide (15.4 g, 0.285 mol) in methanol (500 mL). A solution of ethyl serinate, hydrochloride salt (382 g, 2.45 mol) in methanol (300 mL) was then added to the −5° C. reaction mixture, which was subsequently allowed to stir at room temperature for 16 hours. Dichloromethane (1 L) and water (800 mL) were added, and the aqueous layer was extracted with dichloromethane (1 L); the combined organic layers were concentrated in vacuo to provide the product as a yellow oil, which was used in the next step without additional purification. Yield: 300 g, 1.4 mol, 71%. $^1$H NMR (400 MHz, CDCl$_3$) δ 6.29 (s, 1H), 4.90 (dd, J=10.8, 8.3 Hz, 1H), 4.74 (dd, J=8.8, 8.3 Hz, 1H), 4.66 (dd, J=10.8, 8.9 Hz, 1H), 3.82 (s, 3H).

Step 2. Synthesis of methyl 2-(chloromethyl)-4-methoxy-4,5-dihydro-1,3-oxazole-4-carboxylate (C14)

A solution of C13 (205 g, 0.967 mol) in methanol (700 mL) was added drop-wise to a cooled solution of sodium methoxide (52.2 g, 0.966 mol) in methanol (300 mL), at a rate sufficient to maintain the reaction temperature below 10° C. The reaction mixture was then stirred at room temperature for 16 hours, whereupon it was diluted with dichloromethane (1 L) and water (800 mL). The aqueous layer was extracted with dichloromethane (2×500 mL), and the combined organic layers were concentrated in vacuo to afford the product as a yellow oil. This material was used in the next step without additional purification. Yield: 200 g, 0.96 mol, 99%.

Step 3. Synthesis of methyl 2-(chloromethyl)-1,3-oxazole-4-carboxylate (C15)

(7,7-Dimethyl-2-oxobicyclo[2.2.1]hept-1-yl)-methanesulfonic acid (camphorsulfonic acid, 45.9 g, 0.198 mol) was added to a solution of C14 (193 g, 0.930 mol) in toluene (700 mL), and the reaction mixture was heated at 70° C. for 1 hour. Water (1 L) was added, and the mixture was extracted with ethyl acetate (2×1 L); the combined organic layers were sequentially washed with aqueous potassium carbonate solution (10%, 500 mL), water (800 mL), and saturated aqueous sodium chloride solution (0.8 L), dried, and concentrated in vacuo. Silica gel chromatography (Gradient: 5% to 25% ethyl acetate in petroleum ether) provided the product as a white solid. Yield: 55 g, 0.31 mol, 33%. $^1$H NMR (400 MHz, CDCl$_3$) δ 8.26 (s, 1H), 4.65 (s, 2H), 3.93 (s, 3H).

Step 4. Synthesis of methyl 2-(fluoromethyl)-1,3-oxazole-4-carboxylate (C16)

To a suspension of C15 (40 g, 0.23 mol) in acetonitrile (1 L) was added tetrabutylammonium fluoride (357 g, 1.36 mol), and the reaction mixture was stirred at 25° C. for 16 hours. After removal of solvent in vacuo, the residue was diluted with water (1 L) and extracted with ethyl acetate (4×1 L). The combined organic layers were dried over sodium sulfate, filtered, and concentrated under reduced pressure. Chromatography on silica gel (Gradient: 17% to 23% ethyl acetate in petroleum ether) afforded the product as a yellow solid. Yield: 8.7 g, 55 mmol, 24%. $^1$H NMR (400 MHz, CDCl$_3$) δ 8.31 (d, J=1.2 Hz, 1H), 5.43 (d, $J_{HF}$=47.2 Hz, 2H), 3.94 (s, 3H).

Step 5. Synthesis of 2-(fluoromethyl)-1,3-oxazole-4-carboxylic acid (C17)

To a solution of C16 (18 g, 110 mmol) in tetrahydrofuran (150 mL) was added a solution of lithium hydroxide (5.42 g, 226 mmol) in a mixture of methanol and water (1:1, 500 mL). The reaction mixture was stirred at room temperature for 1 hour, whereupon it was concentrated in vacuo. After the residue had been dissolved in water (500 mL), it was acidified to a pH of 2 by addition of 2 M aqueous hydrochloric acid. The aqueous layer was then extracted with ethyl acetate (2×100 mL), and the combined organic layers were dried over sodium sulfate, filtered, and concentrated under reduced pressure, providing the product as a yellow solid. Yield: 13 g, 90 mmol, 82%. LCMS m/z 144.0 [M−H$^+$]. $^1$H NMR (400 MHz, CD$_3$OD) δ 8.61 (s, 1H), 5.47 (d, $J_{HF}$=47 Hz, 2H).

Step 6. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide (C18)

A solution of P2 (803 mg, 2.07 mmol) and C17 (300 mg, 2.07 mmol) in ethyl acetate (4 mL) was cooled to 0° C. and treated with pyridine (0.67 mL, 8.3 mmol) and 2,4,6-tripropyl-1,3,5,2,4,6-trioxatriphosphinane 2,4,6-trioxide (T3P, 50% solution in ethyl acetate, 2.46 mL, 4.13 mmol). The reaction mixture was allowed to stir for 2 hours, whereupon it was diluted with ethyl acetate, washed sequentially with aqueous hydrochloric acid (1 M, three times), aqueous sodium bicarbonate solution, and saturated aqueous sodium chloride solution, and then concentrated in vacuo. Silica gel chromatography (Gradient: 0% to 100% ethyl acetate in heptane) provided the product as a solid. Yield: 650 mg, 1.26 mmol, 61%. LCMS m/z 516.1 [M+H]$^+$.

Step 7. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide (3)

Pyridine (12.9 mL, 158 mmol) and methoxylamine hydrochloride (1.31 g, 15.7 mmol) were added to a solution of C18 (0.81 g, 1.6 mmol) in ethanol (16 mL), and the reaction mixture was stirred at 50° C. for 2.5 hours, whereupon it was cooled to room temperature and concentrated in vacuo. The residue was diluted with dichloromethane (5 mL) and washed sequentially with aqueous sodium bicarbonate solution (3 times), water, and saturated aqueous sodium chloride solution, dried over sodium sulfate, filtered, and concentrated under reduced pressure. Chromatography on silica gel (Gradient: 0% to 80% ethyl acetate in heptane) gave material that was treated with a minimum amount of acetonitrile at 50° C. The resulting slurry was cooled to room temperature with stirring and allowed to crystallize. Filtration under reduced pressure provided the product as a crystalline solid (as confirmed by microscopic analysis and birefringence). Yield: 360 mg, 0.875 mmol, 55%. LCMS m/z 412.1 [M+H]$^+$. $^1$H NMR (400 MHz, CDCl$_3$) δ 9.37 (br s, 1H), 8.36 (d, J=1.4 Hz, 1H), 7.65 (s, 1H), 5.44 (d, $J_{HF}$=47.2 Hz, 2H), 4.47-4.64 (br s, 2H), 3.89 (AB quartet, downfield doublet is broadened, $J_{AB}$=11.0 Hz, $\Delta v_{AB}$=45.1 Hz, 2H), 3.69-3.78 (m, 1H), 3.16 (dd, J=12.5, 4.0 Hz, 1H), 2.77-2.85 (m, 1H), 2.59 (dd, J=12.5, 2.8 Hz, 1H), 1.81 (ddd, J=13, 13, 11 Hz, 1H), 1.54 (ddd, J=13, 4, 2 Hz, 1H), 1.30 (d, J=6.1 Hz, 3H).

Example 4

N-{2-[(4aR,6S,8aR)-2-Amino-6-methyl-4,4a,5,6-tetrahydropyrano[3,4-d][1,3] thiazin-8a(8H)-yl]-1,3-thiazol-4-yl}-1-(difluoromethyl)-1H-pyrazole-3-carboxamide (4)

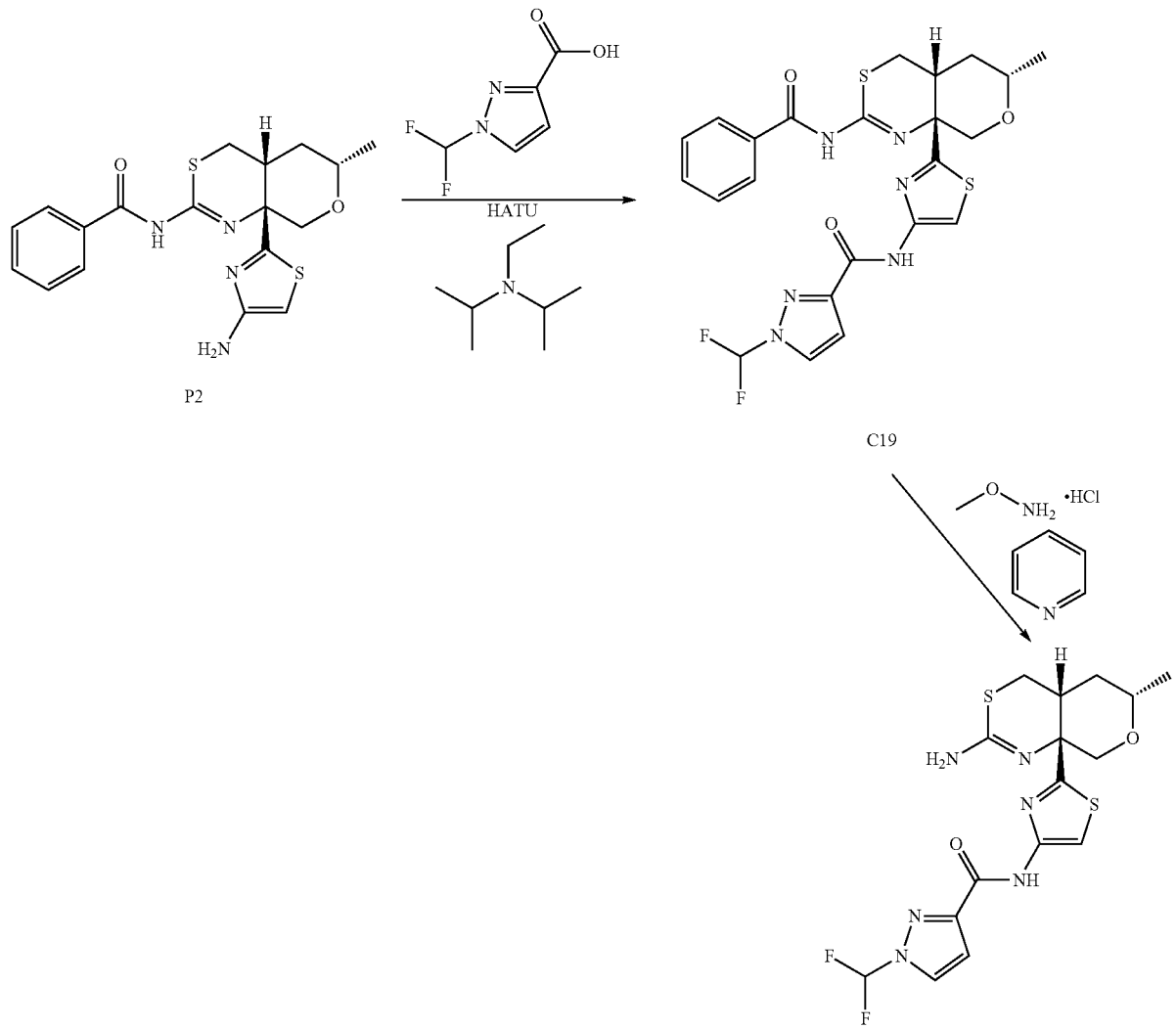

Step 1. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide (C19)

To a solution of 1-(difluoromethyl)-1H-pyrazole-3-carboxylic acid (125 mg, 0.771 mmol) in N,N-dimethylformamide (5 mL) was added N,N-diisopropylethylamine (416 mg, 3.22 mmol) at room temperature, followed by addition of O-7-azabenzotriazol-1-yl)-N,N,N',N'-tetramethyluronium hexafluorophosphate (HATU, 734 mg, 1.93 mmol). After the reaction mixture had been stirred for 30 minutes, a solution of P2 (250 mg, 0.644 mmol) in N,N-dimethylformamide (2 mL) was added via syringe, and stirring was continued for 16 hours. The reaction mixture was then poured into ice water (150 mL) and extracted with ethyl acetate (2×100 mL); the combined organic layers were washed with water (2×100 mL) and with saturated aqueous sodium chloride solution (2×100 mL), dried over sodium sulfate, filtered, and concentrated in vacuo. Purification via preparative thin layer chromatography on silica gel (Eluent: 2:1 petroleum ether/ethyl acetate) afforded the product as a yellow oil. Yield: 150 mg, 0.28 mmol, 43%. LCMS m/z 532.9 [M+H]$^+$.

Step 2. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide (4)

Methoxylamine hydrochloride (236 mg, 2.82 mmol) and pyridine (2.19 g, 27.7 mmol) were added to a solution of C19 (150 mg, 0.28 mmol) in ethanol (4 mL), and the reaction mixture was heated at reflux for 16 hours. Solvent was removed under reduced pressure, and the residue was purified via reversed phase HPLC (Column: Agela Durashell C18, 5 μm; Mobile phase A: aqueous ammonia, pH 10; Mobile phase B: acetonitrile; Gradient: 15% to 35% B), providing the product as a white solid. Yield: 54.7 mg, 0.128 mmol, 46%. LCMS m/z 428.8 [M+H]$^+$. $^1$H NMR (400 MHz, CDCl$_3$) δ 9.35 (br s, 1H), 7.90 (d, J=2.4 Hz, 1H), 7.65 (s, 1H), 7.22 (t, $J_{HF}$=60.5 Hz, 1H), 7.08 (d, J=2.6 Hz, 1H), 4.50-4.62 (br s, 2H), 3.90 (AB quartet, $J_{AB}$=11 Hz, $\Delta v_{AB}$=43 Hz, 2H), 3.69-3.79 (m, 1H), 3.16 (dd, J=12, 4 Hz, 1H), 2.77-2.85 (m, 1H), 2.56-2.62 (m, 1H), 1.75-1.87 (m, 1H), 1.51-1.6 (m, 1H, assumed; partially obscured by water peak), 1.29 (d, J=6.2 Hz, 3H).

Example 5

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-cyanopyridine-2-carboxamide (5)

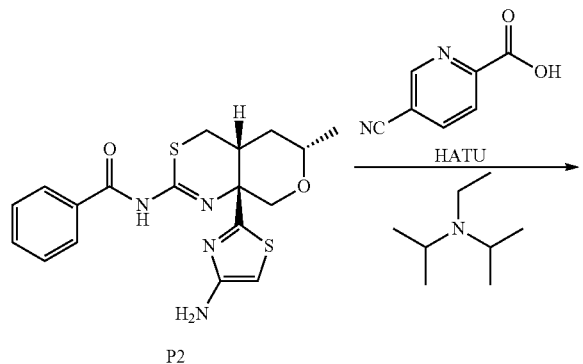

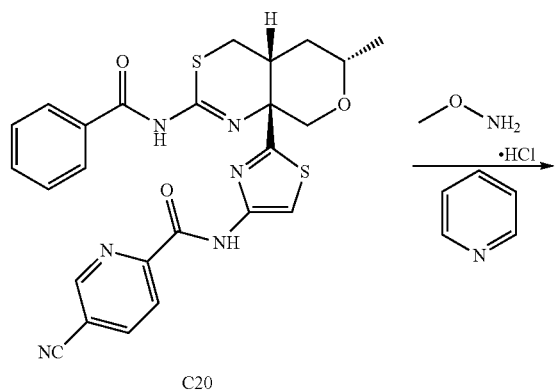

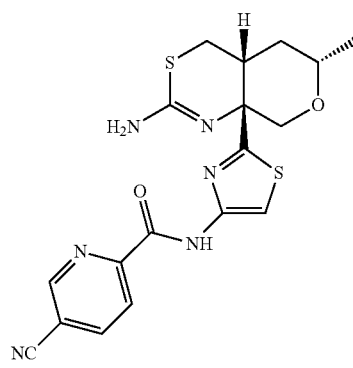

Step 1. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-cyanopyridine-2-carboxamide (C20)

Reaction of P2 with 5-cyanopyridine-2-carboxylic acid was carried out using the method described for synthesis of C19 in Example 4. The product was obtained as a yellow oil. Yield: 300 mg, 0.58 mmol, 45%. LCMS m/z 519.1 [M+H]$^+$.

Step 2. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyanopyridine-2-carboxamide (5)

Methoxylamine hydrochloride (483 mg, 5.78 mmol) and pyridine (4.58 g, 57.9 mmol) were added to a solution of C20 (300 mg, 0.58 mmol) in ethanol (4 mL), and the reaction mixture was stirred at 50° C. for 16 hours. After removal of solvent under reduced pressure, the residue was purified via reversed phase HPLC (Column: Kromasil Eternity XT C18, 10 μm; Mobile phase A: aqueous ammonia, pH 10; Mobile phase B: acetonitrile; Gradient: 22% to 42% B) to afford the product as a white solid. Yield: 69 mg, 0.17 mmol, 29%. LCMS m/z 414.8 [M+H]$^+$. $^1$H NMR (400 MHz, CDCl$_3$) δ 10.44 (br s, 1H), 8.90-8.94 (m, 1H), 8.43 (br d, J=8.3 Hz, 1H), 8.22 (dd, J=8, 2 Hz, 1H), 7.77 (s, 1H), 4.5-4.9 (br s, 2H), 3.92 (AB quartet, $J_{AB}$=11 Hz, $\Delta v_{AB}$=44 Hz, 2H), 3.70-3.80 (m, 1H), 3.17 (dd, J=12, 4 Hz, 1H), 2.81-2.89 (m, 1H), 2.61 (dd, J=13, 3 Hz, 1H), 1.75-1.87 (m, 1H), 1.52-1.60 (m, 1H), 1.30 (d, J=6.2 Hz, 3H).

Example 6

N-{2-[(4a R, 6S,8aR)-2-Amino-6-methyl-4,4a,5,6-tetrahydropyrano[3,4-d][1,3] thiazin-8a(8H)-yl]-1,3-thiazol-4-yl}-4-chloro-1-(difluoromethyl)-1H-pyrazole-3-carboxamide (6)

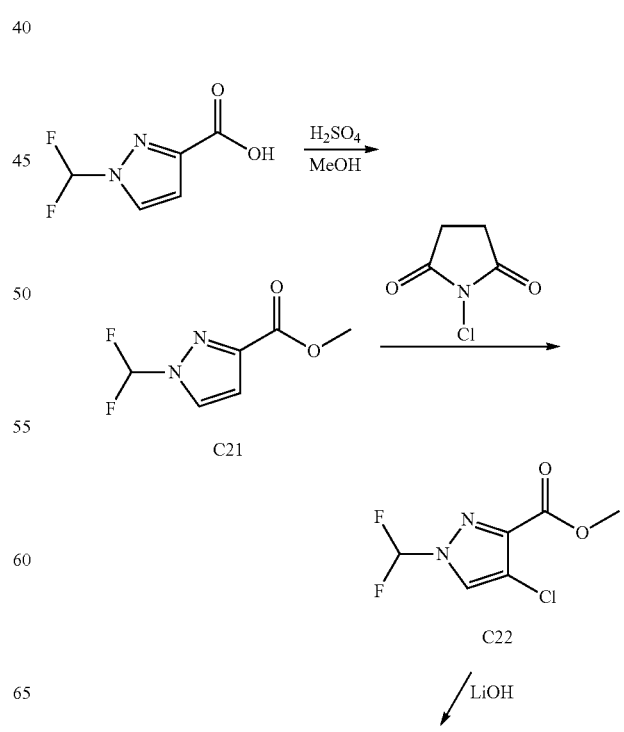

-continued

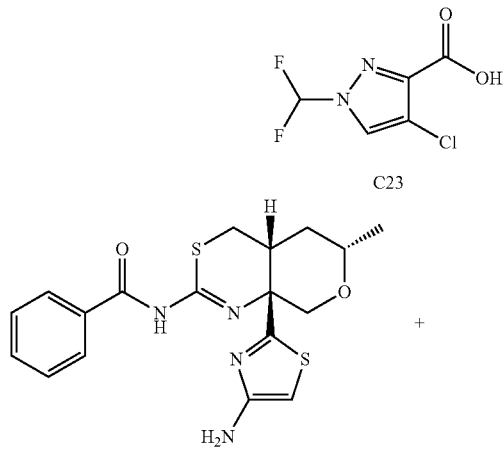

+

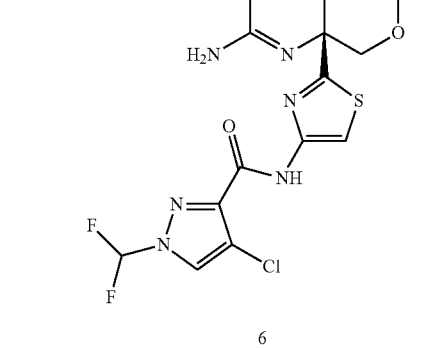

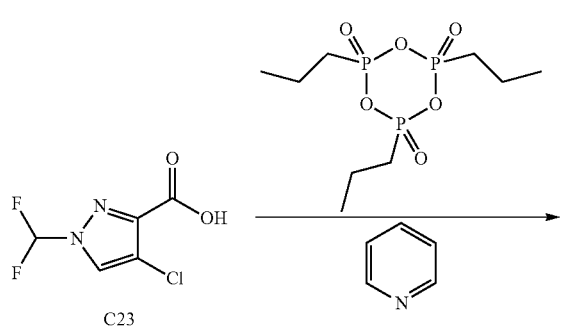

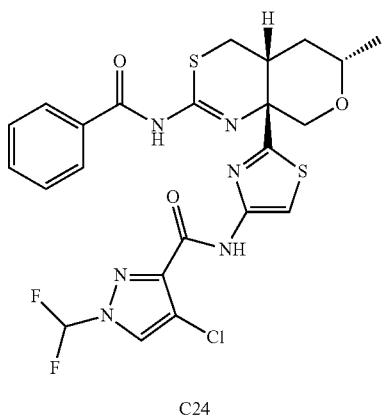

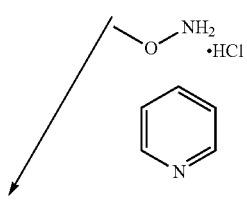

Step 1. Synthesis of methyl 1-(difluoromethyl)-1H-pyrazole-3-carboxylate (C21)

A solution of 1-(difluoromethyl)-1H-pyrazole-3-carboxylic acid (238 mg, 1.47 mmol) in methanol (9 mL) was cooled to 0° C. and treated with concentrated sulfuric acid (98%, 0.10 mL, 1.8 mmol). The reaction mixture was heated at reflux for 2 hours, whereupon it was cooled, concentrated in vacuo, and partitioned between ethyl acetate (15 mL) and water (15 mL). The organic layer was washed with water (3×10 mL) until the water washes reached pH 4-5, then washed with saturated aqueous sodium bicarbonate solution (10 mL), dried over sodium sulfate, filtered, and concentrated under reduced pressure. The product was obtained as a clear, colorless oil. Yield: 241 mg, 1.37 mmol, 93%. LCMS m/z 177.0 [M+H]$^+$. $^1$H NMR (400 MHz, CDCl$_3$) δ 7.89 (d, J=2.7 Hz, 1H), 7.28 (t, J$_{HF}$=60.0 Hz, 1H), 6.99 (d, J=2.6 Hz, 1H), 3.98 (s, 3H).

Step 2. Synthesis of methyl 4-chloro-1-(difluoromethyl)-1H-pyrazole-3-carboxylate (C22)

A solution of C21 (235 mg, 1.33 mmol) and N-chlorosuccinimide (600 mg, 4.5 mmol) in N,N-dimethylformamide (2.5 mL) was heated at 50° C. for 16 hours. N-Chlorosuccinimide (0.40 g, 3.0 mmol) was again added, and heating was continued for 5 hours. The reaction mixture was then cooled, poured into water (20 mL), and extracted with ethyl acetate (4×20 mL). The combined organic layers were washed with saturated aqueous sodium chloride solution (20 mL), washed with water, dried over sodium sulfate, filtered, and concentrated in vacuo. Silica gel chromatography (Gradient: 0% to 50% ethyl acetate in heptane) provided the product as a white solid. Yield: 158 mg, 0.750 mmol, 56%. GCMS m/z 210, 212 (M$^+$). $^1$H NMR (400 MHz, DMSO-d$_6$) δ 8.79 (s, 1H), 7.89 (t, J$_{HF}$=58.5 Hz, 1H), 3.87 (s, 3H).

Step 3. Synthesis of 4-chloro-1-(difluoromethyl)-1H-pyrazole-3-carboxylic acid (C23)

Compound C22 was hydrolyzed using the method described for synthesis of C17 in Example 3. The product was obtained as a white solid. Yield: 138 mg, 0.702 mmol, 95%. $^1$H NMR (400 MHz, DMSO-d$_6$) δ 13.62 (br s, 1H), 8.73 (s, 1H), 7.87 (t, J$_{HF}$=58.6 Hz, 1H).

Step 4. Synthesis of N-{2-[(4aR,6S,8aR)-2-(benzoylamino)-6-methyl-4,4a,5,6-tetrahydropyrano[3,4-d],[1,3]thiazin-8a(8H)-yl]-1,3-thiazol-4-yl}-4-chloro-1-(difluoromethyl)-1H-pyrazole-3-carboxamide (C24)

Reaction of P2 with C23 was carried out using the method described for synthesis of C18 in Example 3, affording the product as a white solid. Yield: 63 mg, 0.11 mmol, 71%. LCMS m/z 567.1 [M+H]$^+$. $^1$H NMR (400 MHz, CDCl$_3$) δ 9.31 (s, 1H), 7.98-8.24 (br s, 2H), 7.95 (s, 1H), 7.70-7.83 (br s, 1H), 7.39-7.65 (m, 3H), 7.16 (t, $J_{HF}$=60 Hz, 1H), 3.86-4.05 (m, 2H), 3.70-3.82 (m, 1H), 3.12-3.25 (m, 1H), 2.92-3.07 (m, 1H), 2.54-2.69 (m, 1H), 1.77-1.98 (m, 1H), 1.53-1.74 (m, 2H), 1.27-1.35 (m, 3H).

Step 5. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-chloro-1-(difluoromethyl)-1H-pyrazole-3-carboxamide (6)

Compound C24 was converted to the product according to the method described for synthesis of 2 in Example 2. The product was obtained as a white solid. Yield: 41.9 mg, 90.5 μmol, 85%. LCMS m/z 463.0, 465.0 [M+H]$^+$. $^1$H NMR (400 MHz, CDCl$_3$) δ 9.27 (br s, 1H), 7.94 (s, 1H), 7.68 (s, 1H), 7.15 (t, $J_{HF}$=60 Hz, 1H), 4.46-4.66 (br s, 2H), 3.89 (AB quartet, $J_{AB}$=11 Hz, $\Delta v_{AB}$=44 Hz, 2H), 3.68-3.78 (m, 1H), 3.12-3.19 (m, 1H), 2.74-2.83 (m, 1H), 2.58 (br d, J=12 Hz, 1H), 1.75-1.87 (m, 1H), 1.49-1.57 (m, 1H), 1.29 (d, J=6 Hz, 3H).

Example 7

N-{2-[(4aR, 6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide (7)

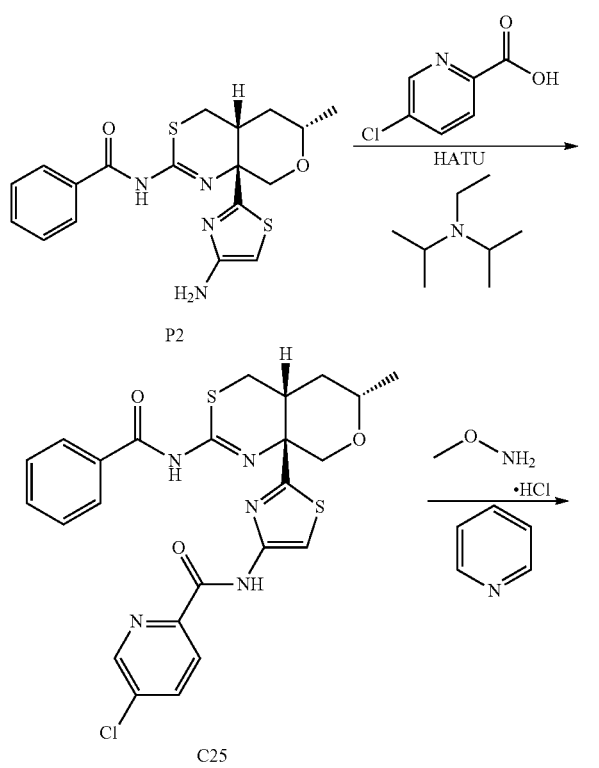

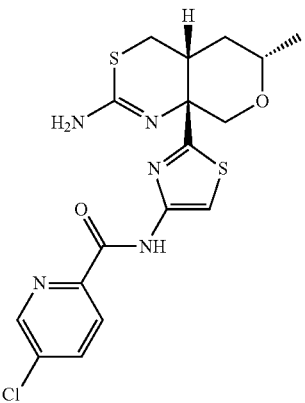

Step 1. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-chloropyridine-2-carboxamide (C25)

5-Chloropyridine-2-carboxylic acid was reacted with P2 using the method described for synthesis of C19 in Example 4. The product was obtained as a colorless oil. Yield: 80 mg, 0.15 mmol, 71%. LCMS m/z 527.9 [M+H]$^+$.

Step 2. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloropyridine-2-carboxamide (7)

Methoxylamine hydrochloride (94.9 mg, 1.14 mmol) and pyridine (899 mg, 11.4 mmol) were added to a solution of C25 (60 mg, 0.11 mmol) in ethanol (5 mL), and the reaction mixture was heated at reflux for 72 hours. Volatiles were removed under reduced pressure, and the residue was purified by reversed phase HPLC (Column: Phenomenex Gemini C18, 8 μm; Mobile phase A: aqueous ammonia, pH 10; Mobile phase B: acetonitrile; Gradient: 45% to 65% B) to afford the product as a white solid. Yield: 12.7 mg, 30.0 μmol, 27%. LCMS m/z 423.8 [M+H]$^+$. $^1$H NMR (400 MHz, CDCl$_3$) δ 10.40 (br s, 1H), 8.58 (d, J=2.3 Hz, 1H), 8.24 (d, J=8.3 Hz, 1H), 7.90 (dd, J=8.4, 2.4 Hz, 1H), 7.73 (s, 1H), 4.5-4.8 (br s, 2H), 3.92 (AB quartet, $J_{AB}$=11.1 Hz, $\Delta v_{AB}$=40.2 Hz, 2H), 3.71-3.80 (m, 1H), 3.18 (dd, J=12.6, 4.2 Hz, 1H), 2.81-2.89 (m, 1H), 2.60 (dd, J=12, 3 Hz, 1H), 1.75-1.87 (m, 1H), 1.51-1.59 (m, 1H), 1.30 (d J=6.2 Hz, 3H).

Alternate Synthesis of Example 7, Hydrochloride Salt

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide, hydrochloride salt (7.HCl)

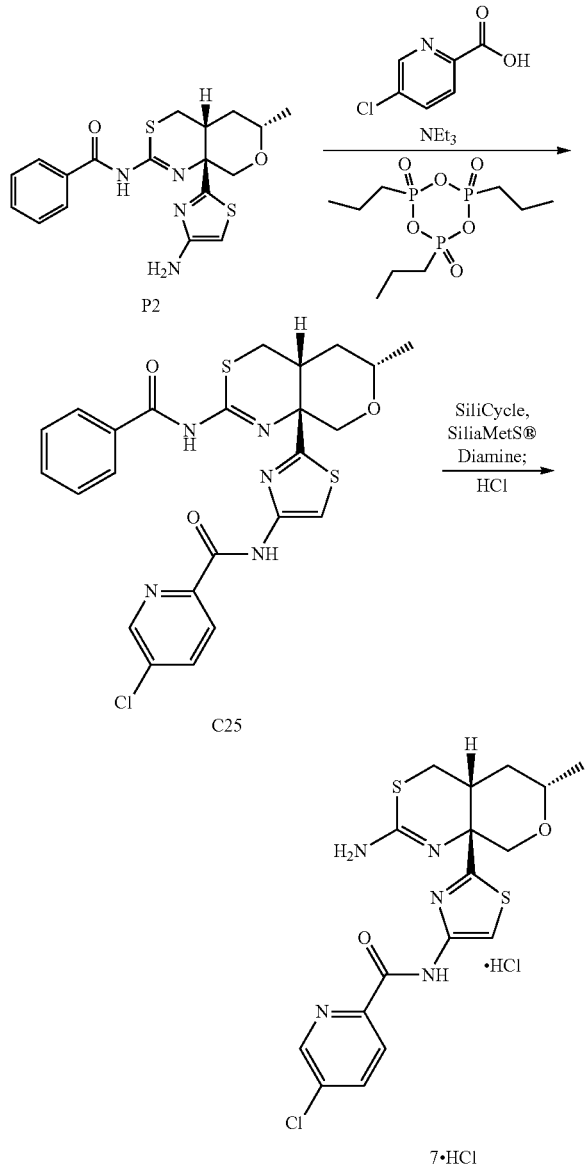

Step 1. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-chloropyridine-2-carboxamide (C25)

2,4,6-Tripropyl-1,3,5,2,4,6-trioxatriphosphinane 2,4,6-trioxide (50% solution by weight in ethyl acetate, 732 mL, 1.23 mol) was added over 25 minutes to a 0° C. to 5° C. mixture of P2 (191.0 g, 491.6 mmol), 5-chloropyridine-2-carboxylic acid (79.8 g, 506 mmol), and triethylamine (274 mL, 1.97 mol) in ethyl acetate (1.05 L). The reaction mixture was allowed to warm to room temperature and was stirred for 1 hour, whereupon it was diluted with dichloromethane (1.9 L) and quenched with aqueous hydrochloric acid (1 M, 1.9 L). The organic layer was washed with saturated aqueous sodium bicarbonate solution (1.9 L), then displaced with 2-propanol to a volume of 2.8 L at a temperature of 80° C. The resulting slurry was cooled to 0° C. to 5° C. and granulated for 30 minutes; the solid was collected via filtration and washed with cold 2-propanol, affording the product as a light pink solid. Yield: 226.3 g, 428.6 mmol, 87%.

Step 2. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloropyridine-2-carboxamide, Hydrochloride Salt (7.HCl)

SiliCycle, SiliaMetS® Diamine (1.13 kg, 1.28 mol) was added to a solution of C25 (226.3 g, 428.6 mmol) in toluene (2.26 L), and the reaction mixture was heated at reflux overnight. It was then cooled to 50° C. and diluted with tetrahydrofuran (2.26 L). After cooling to room temperature, the mixture was filtered through diatomaceous earth to remove the SiliCycle reagent, and the filter pad was washed with tetrahydrofuran (1 L). The combined filtrates were concentrated in vacuo to a volume of approximately 2.5 L, whereupon concentrated hydrochloric acid (73.6 mL, 884 mmol) was added. The mixture was repeatedly concentrated in vacuo with 2-propanol (3×2.3 L) to a final volume of 2.3 L, then cooled to 0° C. to 5° C. and granulated for 30 minutes. Filtration, followed by washing of the collected solid with cold 2-propanol, afforded the product as a solid (135.4 g). Additional product was obtained from the spent SiliCycle reagent as follows: the spent material was slurried and stirred in tetrahydrofuran (1.5 L), then filtered through diatomaceous earth. The filter pad was washed with tetrahydrofuran (500 mL), and the combined filtrates were concentrated in vacuo to provide approximately 55 g of material. This was mixed with 2-propanol (550 mL), treated with concentrated hydrochloric acid (18.5 mL, 222 mmol), and granulated at room temperature for 30 minutes. Filtration and washing of the collected solid with cold 2-propanol afforded additional product as a solid (42.1 g). These two batches of product were combined, treated with methanol (1.8 L) and dichloromethane (2.2 L), and heated to reflux. The resulting solution was concentrated to a volume of approximately 1.5 L, then displaced with 2-propanol to a volume of approximately 1.8 L. This mixture was cooled to 0° C. to 5° C. and granulated for 30 minutes; the solid was collected by filtration and washed with cold 2-propanol, affording the product as a solid. Yield: 165.8 g, 360.1 mmol, 84% LCMS m/z 424.3, 426.3 [M+H]$^+$. $^1$H NMR (400 MHz, CD$_3$OD) δ 8.71 (dd, J=2.4, 0.7 Hz, 1H), 8.22 (dd, half of ABX pattern, J=8.4, 0.7 Hz, 1H), 8.09 (dd, half of ABX pattern, J=8.4, 2.4 Hz, 1H), 7.90 (s, 1H), 4.06 (s, 2H), 3.82-3.92 (m, 1H), 3.19-3.26 (m, 2H), 2.97-3.04 (m, 1H), 1.83 (ddd, J=14, 4, 2.5 Hz, 1H), 1.62 (ddd, J=14, 11.5, 11.5 Hz, 1H), 1.29 (d, J=6.2 Hz, 3H).

Generation of Crystalline Example 7, Hydrochloride Salt

A sample of Example 7 (150 mg, 0.35 mmol) was dissolved in ethanol (10 mL) at 60° C. Concentrated hydrochloric acid (59.0 µL, 0.708 mmol) was added, and the slurry was allowed to slowly cool to room temperature with stirring. The resulting crystals were collected via filtration to afford the product as a white solid, which was crystalline by powder X-ray diffraction analysis. Yield: 147 mg, 0.319 mmol, 91%. LCMS m/z 424.1, 426.1 [M+H]+. $^1$H NMR (400 MHz, DMSO-$d_6$) δ 11.20 (br s, 1H), 10.78 (s, 1H), 9.5-9.9 (v br s, 1H), 8.81 (d, J=2.4 Hz, 1H), 8.5-8.85 (v br s, 1H), 8.23 (dd, half of ABX pattern, J=8.4, 2.4 Hz, 1H), 8.16 (d, half of AB quartet, J=8.4 Hz, 1H), 7.85 (s, 1H), 4.04 (d, J=12.2 Hz, 1H), 3.88 (d, J=12.0 Hz, 1H), 3.75-3.85 (m, 1H), 3.01-3.12 (m, 3H), 1.73-1.82 (m, 1H), 1.39-1.51 (m, 1H), 1.21 (d, J=6.2 Hz, 3H).

Example 8

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-2-(difluoromethyl)-1,3-oxazole-4-carboxamide (8)

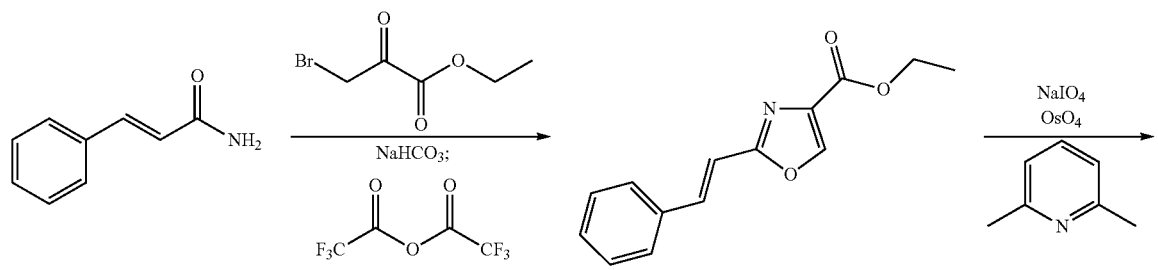

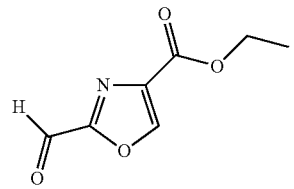

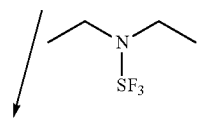

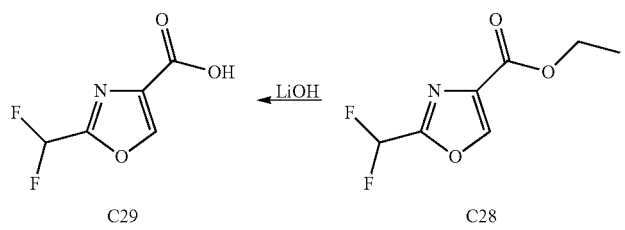

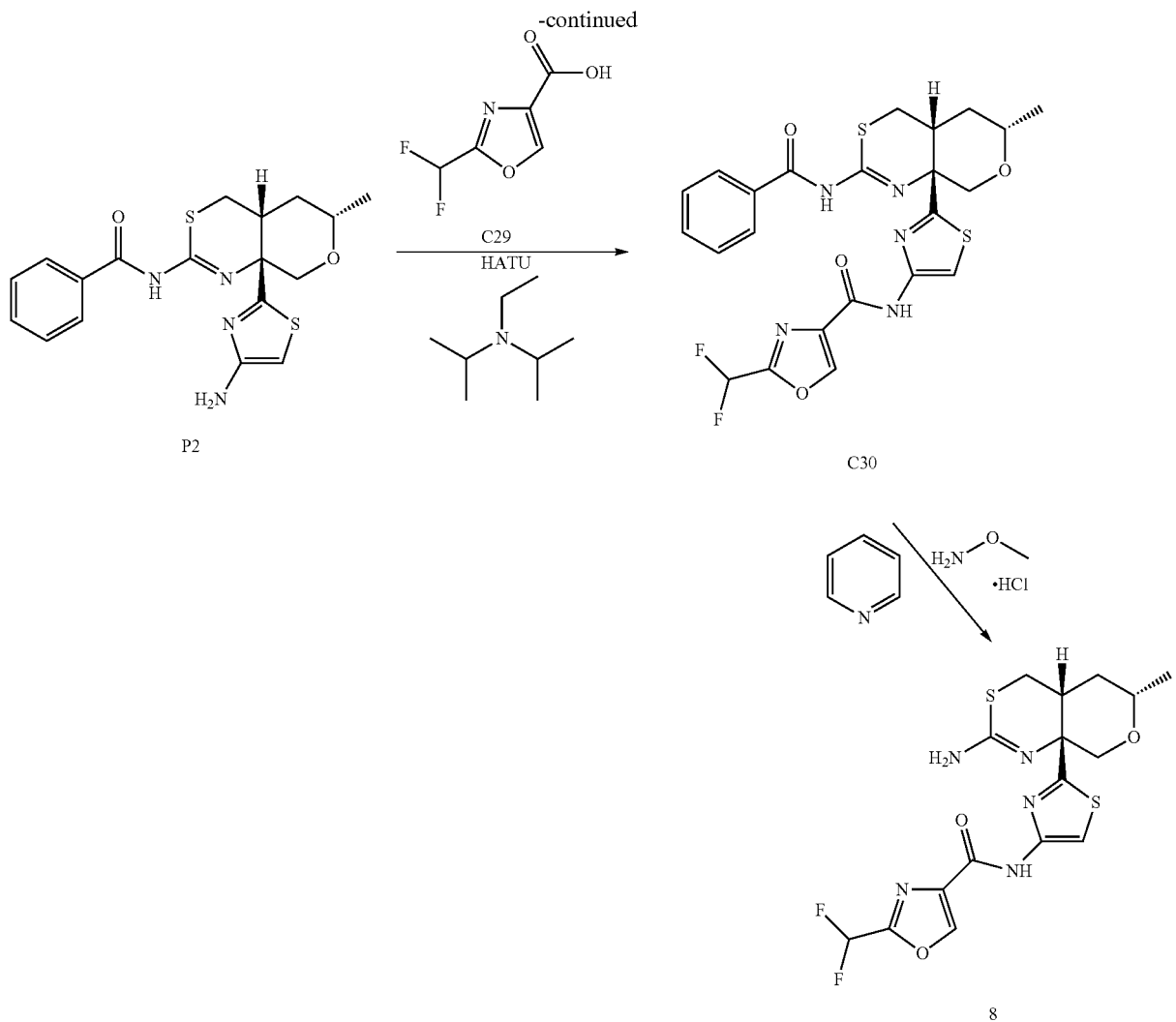

Step 1. Synthesis of ethyl 2-[(E)-2-phenylethenyl]-1,3-oxazole-4-carboxylate (C26)

A mixture of (2E)-3-phenylprop-2-enamide (2.00 g, 13.6 mmol) and sodium bicarbonate (4.57 g, 54.4 mmol) in tetrahydrofuran (48 mL) was cooled to 0° C. Ethyl 3-bromo-2-oxopropanoate (3.16 mL, 25.2 mmol) was added dropwise, and the reaction mixture was heated at reflux for 4 hours, whereupon it was filtered through diatomaceous earth and concentrated in vacuo. The residue was dissolved in tetrahydrofuran (33 mL), cooled to 0° C., and treated dropwise with trifluoroacetic anhydride (14.8 mL, 105 mmol). The reaction mixture was stirred at room temperature for 10 hours, then cooled to 0° C. and quenched via addition of saturated aqueous sodium bicarbonate solution. The mixture was extracted three times with ethyl acetate, and the combined organic layers were washed with saturated aqueous sodium chloride solution, dried over sodium sulfate, filtered, and concentrated under reduced pressure. Chromatography on silica gel (Gradient: 0% to 30% ethyl acetate in heptane) provided partially purified product; this was crystallized from heptane/ethyl acetate to afford the product as pale yellow needles. Yield: 1.52 g, 6.25 mmol, 46%. LCMS m/z 244.1 [M+H]+. $^1$H NMR (400 MHz, CDCl$_3$) δ 8.20 (s, 1H), 7.63 (d, J=16.4 Hz, 1H), 7.51-7.56 (m, 2H), 7.34-7.43 (m, 3H), 6.97 (d, J=16.5 Hz, 1H), 4.42 (q, J=7.1 Hz, 2H), 1.41 (t, J=7.1 Hz, 3H).

Step 2. Synthesis of ethyl 2-formyl-1,3-oxazole-4-carboxylate (C27)

To a solution of C26 (394 mg, 1.62 mmol) in a mixture of 1,4-dioxane and water (3:1, 16 mL) was added 2,6-dimethylpyridine (375 µL, 3.24 mmol), osmium tetroxide (8.1 mg, 32 µmol, as a 2.5 weight % solution in tert-butanol) and sodium periodate (1.39 g, 6.50 mmol). After 23 hours at room temperature, the reaction mixture was partitioned between dichloromethane and water; the aqueous layer was extracted three times with dichloromethane, and the combined organic layers were washed with saturated aqueous sodium chloride solution, dried over sodium sulfate, filtered, and concentrated in vacuo. Silica gel chromatography (Gradient: 0% to 80% ethyl acetate in heptane) afforded the product as a solid. Yield: 102 mg, 0.603 mmol, 37%. $^1$H NMR (400 MHz, CDCl$_3$) δ 9.83 (d, J=0.9 Hz, 1H), 8.43 (d, J=0.8 Hz, 1H), 4.46 (q, J=7.1 Hz, 2H), 1.43 (t, J=7.2 Hz, 3H).

Step 3. Synthesis of ethyl 2-(difluoromethyl)-1,3-oxazole-4-carboxylate (C28)

(Diethylamino)sulfur trifluoride (126 µL, 0.954 mmol) was added to a 0° C. solution of C27 (102 mg, 0.603 mmol) in dichloromethane (4 mL), and the reaction mixture was allowed to warm to room temperature. After 72 hours, the reaction mixture was partitioned between water and dichloromethane. The organic layer was washed sequentially with 1 M aqueous hydrochloric acid, water, saturated aqueous sodium bicarbonate solution, and saturated aqueous sodium chloride solution, dried over magnesium sulfate, filtered, and concentrated in vacuo. Silica gel chromatography (Gradient: 0% to 30% ethyl acetate in heptane) provided the product as a white fluffy solid. Yield: 72.5 mg, 0.379 mmol, 63%. $^1$H NMR (400 MHz, CDCl$_3$) δ 8.34 (td, J=0.8, 0.3 Hz, 1H), 6.70 (td, J=52.1, 0.3 Hz, 1H), 4.42 (q, J=7.1 Hz, 2H), 1.40 (t, J=7.1 Hz, 3H).

Step 4. Synthesis of 2-(difluoromethyl)-1,3-oxazole-4-carboxylic acid (C29)

Lithium hydroxide (27.2 mg, 1.14 mmol) was added to a solution of C28 (72.5 mg, 0.379 mmol) in a mixture of tetrahydrofuran, water, and methanol (1:1:1, 3 mL), and the reaction mixture was stirred for 3 hours. After removal of volatiles under reduced pressure, the residue was partitioned between diethyl ether (25 mL) and water (25 ml). The aqueous layer was extracted twice with diethyl ether, acidified to pH 1 with 1 M aqueous hydrochloric acid, and extracted three times with dichloromethane. The combined organic layers were dried over sodium sulfate, filtered, and concentrated in vacuo to afford the product as a solid. Yield: 30.3 mg, 0.186 mmol, 49%. $^1$H NMR (400 MHz, DMSO-d$_6$) δ 13.44 (br s, 1H), 9.00 (s, 1H), 7.28 (t, J$_{HF}$=52 Hz, 1H).

Step 5. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-2-(difluoromethyl)-1,3-oxazole-4-carboxamide (C30)

Reaction of C29 with P2 was carried out using the method described for synthesis of C9 in Example 1. The product was obtained as a white solid. Yield: 50.4 mg, 94.4 µmol, 79%. $^1$H NMR (400 MHz, CDCl$_3$) δ 9.37 (br s, 1H), 8.43 (s, 1H), 7.9-8.3 (br s, 2H), 7.72 (s, 1H), 7.51-7.59 (m, 1H), 7.43-7.51 (m, 2H), 6.71 (t, J$_{HF}$=52.4 Hz, 1H), 3.95 (AB quartet, upfield doublet is broadened, J$_{AB}$=12 Hz, Δv$_{AB}$=23 Hz, 2H), 3.72-3.82 (m, 1H), 3.17 (br dd, J=13, 4 Hz, 1H), 2.95-3.06 (m, 1H), 2.61 (dd, J=13, 2 Hz, 1H), 1.83-1.97 (m, 1H), 1.64-1.72 (m, 1H), 1.31 (d, J=6.2 Hz, 3H).

Step 6. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(difluoromethyl)-1,3-oxazole-4-carboxamide (8)

Compound C30 was converted to the product using the method described for synthesis of 5 in Example 5. In this case, the crude product was subjected to silica gel chromatography (Gradient: methanol in dichloromethane). Addition of dichloromethane to a deuterochloroform solution of the chromatographed material produced a solid, which was isolated via filtration to afford the product as a solid. Yield: 7.9 mg, 18 µmol, 19%. $^1$H NMR (400 MHz, DMSO-d$_6$) δ 9.10 (s, 1H), 7.81 (s, 1H), 7.33 (t, J$_{HF}$=52 Hz, 1H), 3.95 (AB quartet, J$_{AB}$=12 Hz, Δv$_{AB}$=82 Hz, 2H), 3.70-3.81 (m, 1H), 2.96-3.10 (m, 3H), 1.79 (br d, J=13 Hz, 1H), 1.39-1.52 (m, 1H), 1.21 (br d, J=5 Hz, 3H).

Alternate Synthesis of Example 45

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide

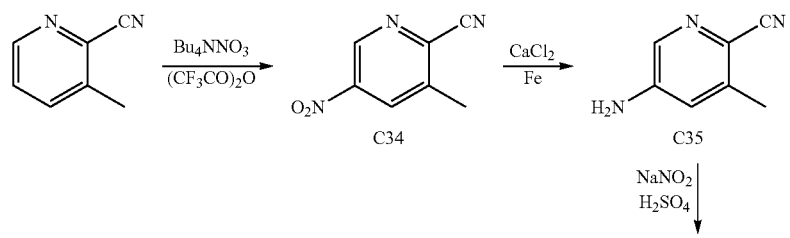

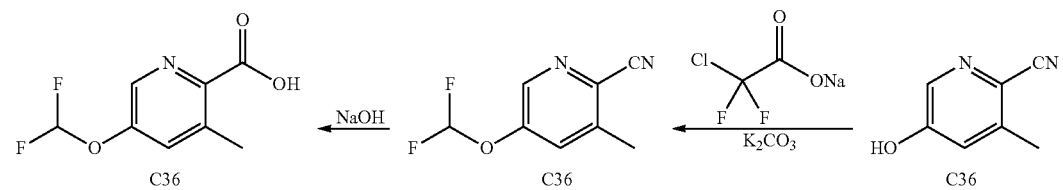

-continued
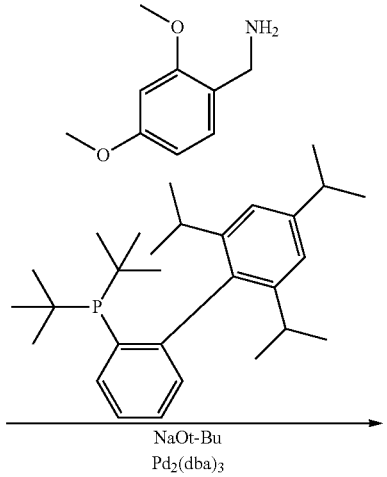
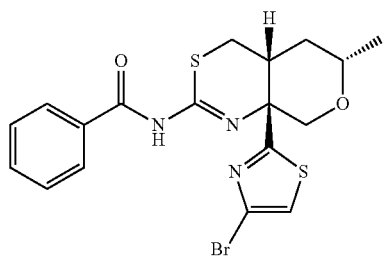
C6
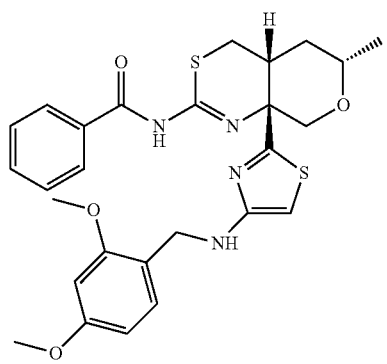
C39
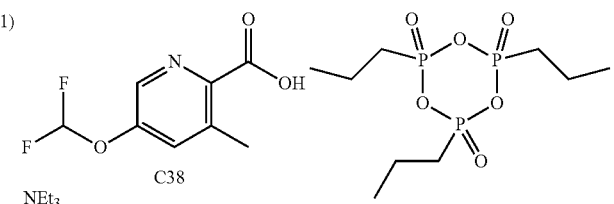
C38
1) NEt₃
2) TFA
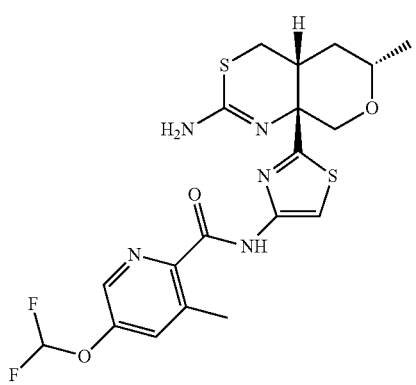
45
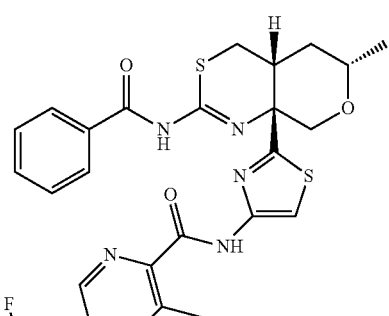
C40
SiliCycle, SiliMetS®
Diamine

Step 1. Synthesis of 3-methyl-5-nitropyridine-2-carbonitrile (C34)

A mixture of 3-methylpyridine-2-carbonitrile (128 g, 1.08 mol) and tetrabutylammonium nitrate (363 g, 1.19 mol) in tert-butyl methyl ether (1.3 L) was cooled to 4° C. Trifluoroacetic anhydride (171 mL, 1.21 mol) was added, and the reaction mixture was allowed to stir at room temperature for 60 hours. It was then adjusted to a pH of approximately 7 by addition of 20% aqueous sodium hydroxide solution, and extracted with dichloromethane (3×1 L). The combined organic layers were dried, filtered, and concentrated in vacuo; purification via silica gel chromatography (Gradient: 0% to 10% ethyl acetate in petroleum ether) afforded the product as a yellow solid. Yield: 70 g, 0.43 mmol, 40%. $^1$H NMR (400 MHz, CDCl$_3$) δ 9.31-9.36 (m, 1H), 8.47-8.52 (m, 1H), 2.74 (s, 3H).

Step 2. Synthesis of 5-amino-3-methylpyridine-2-carbonitrile (C35)

To a solution of C34 (40.0 g, 245 mmol) in ethanol (630 mL) and water (70 mL) was added calcium chloride (13.6 g, 123 mmol), followed by iron powder (123 g, 2.20 mol), and the reaction mixture was stirred overnight at room temperature. After filtration of the reaction mixture, the filtrate was concentrated in vacuo, and the residue was purified by chromatography on silica gel (Gradient: 10% to 50% ethyl acetate in petroleum ether). The product was obtained as a yellow solid. Yield: 20.0 g, 150 mmol, 61%. $^1$H NMR (400 MHz, CDCl$_3$) δ 7.94 (d, J=2.5 Hz, 1H), 6.81 (d, J=2.5 Hz, 1H), 4.07-4.19 (br s, 2H), 2.45 (s, 3H).

Step 3. Synthesis of 5-hydroxy-3-methylpyridine-2-carbonitrile (C36)

Sodium nitrite (1.6 M aqueous solution containing 10.3 g of sodium nitrite, 149 mmol) was slowly added to a 0° C. solution of C35 (18.0 g, 135 mmol) in water (243 mL) and concentrated sulfuric acid (67.5 mL). The reaction mixture was warmed to room temperature and then stirred at 100° C. for 3 hours, whereupon it was cooled and extracted with ethyl acetate (3×75 mL). The combined organic layers were washed with water (2×75 mL) and with saturated aqueous sodium chloride solution (2×75 mL), dried, filtered, and concentrated under reduced pressure to afford the product as a yellow solid. Yield: 16 g, 120 mmol, 89%. $^1$H NMR (400 MHz, DMSO-d$_6$) δ 11.07 (br s, 1H), 8.08 (d, J=2.6 Hz, 1H), 7.20 (d, J=2.3 Hz, 1H), 2.40 (s, 3H).

Step 4. Synthesis of 5-(difluoromethoxy)-3-methylpyridine-2-carbonitrile (C37)

A mixture of C36 (5.70 g, 42.5 mmol), sodium chlorodifluoroacetate (13.0 g, 85.3 mmol), and potassium carbonate (17.6 g, 127 mmol) in N,N-dimethylformamide (175 mL) was stirred for 30 minutes at 100° C. The reaction mixture was then diluted with ethyl acetate (400 mL), and sequentially washed with saturated aqueous ammonium chloride solution (3×200 mL) and saturated aqueous sodium chloride solution (3×200 mL). The combined aqueous layers were extracted with ethyl acetate (200 mL), and the combined organic layers were dried over sodium sulfate, filtered, and concentrated in vacuo. Silica gel chromatography (Gradient: 5% to 15% ethyl acetate in petroleum ether) provided the product as a colorless oil. Yield: 3.9 g, 21 mmol, 49%. $^1$H NMR (400 MHz, CDCl$_3$) δ 8.39 (br d, J=2.1 Hz, 1H), 7.43-7.47 (m, 1H), 6.64 (t, $J_{HF}$=71.5 Hz, 1H), 2.59 (s, 3H).

Step 5. Synthesis of 5-(difluoromethoxy)-3-methylpyridine-2-carboxylic acid (C38)

Aqueous sodium hydroxide solution (1 M, 124 mL, 124 mmol) was added to a solution of C37 (7.60 g, 41.3 mmol) in ethanol (200 mL), and the reaction mixture was stirred for 16 hours at 70° C. It was then diluted with tert-butyl methyl ether (200 mL) and extracted with water (2×100 mL). The combined aqueous layers were washed with tert-butyl methyl ether (100 mL), acidified to pH 2 with 1 M aqueous hydrochloric acid, and extracted with tert-butyl methyl ether (2×200 mL). The combined organic extracts were dried over sodium sulfate, filtered, and concentrated in vacuo to afford the product as a white solid. Yield: 6.6 g, 32 mmol, 77%. LCMS m/z 203.7 [M+H]$^+$. $^1$H NMR (400 MHz, CD$_3$OD) δ 8.32 (br d, J=2.1 Hz, 1H), 7.58-7.62 (m, 1H), 7.06 (t, $J_{HF}$=72.7 Hz, 1H), 2.64 (s, 3H).

Step 6. Synthesis of N-[(4aR,6S,8aR)-8a-{4-[(2,4-dimethoxybenzyl)amino]-1,3-thiazol-2-yl}-6-methyl-4,4a,5,6,8,8a-hexahydropyrano[3,4-d][1,3]thiazin-2-yl]benzamide (C39)

A flask charged with tris(dibenzylideneacetone)dipalladium(0) (3.54 g, 3.87 mmol), di-tert-butyl[2',4',6'-tri(propan-2-yl)biphenyl-2-yl]phosphane (4.93 g, 11.6 mmol), and sodium tert-butoxide (18.6 g, 194 mmol) was purged twice with nitrogen. 1,4-Dioxane (145 mL) was added, and the reaction mixture was heated at 85° C. (internal reaction temperature) for 5 minutes, whereupon a solution of C6 (35.0 g, 77.4 mmol) and 1-(2,4-dimethoxyphenyl)methanamine (19.8 mL, 132 mmol) in 1,4-dioxane (140 mL) was concurrently added through 5 syringes. After the addition had been completed, stirring was continued for 15 minutes at 85° C. (internal reaction temperature); the reaction mixture was then removed from the oil bath and quickly cooled to room temperature via immersion in a water bath. Diatomaceous earth and water (600 mL) were added, and the mixture was filtered through a pad of diatomaceous earth. The pad was washed with dichloromethane (3×300 mL). The organic layer of the combined filtrates was washed with water (3×300 mL) until the pH of the resulting aqueous layer was found to be neutral. The organic layer was then washed sequentially with an aqueous solution of citric acid (5%, 2×500 mL), saturated aqueous sodium bicarbonate solution (2×300 mL), and saturated aqueous sodium chloride solution (500 mL), dried over sodium sulfate, and filtered. The filtrate was adsorbed onto silica gel and chromatographed [Gradient: 10% to 100% (5% triethylamine in ethyl acetate) in heptane]; the orange solid obtained from chromatography was triturated with diethyl ether (100 mL) to afford the product as a white solid (17.8 g). The filtrate from the trituration was concentrated in vacuo, and the residue was triturated with diethyl ether (50 mL) to provide additional product as a brown solid (11.5 g). Combined yield: 29.3 g, 54.4 mmol, 70%. LCMS m/z 539.2 [M+H]$^+$. $^1$H NMR (400 MHz, CDCl$_3$) δ 8.04-8.27 (br s, 2H), 7.39-7.58 (m, 3H), 7.20 (d, J=8.3 Hz, 1H), 6.48 (d, half of AB quartet, J=2.4 Hz, 1H), 6.44 (dd, half of ABX pattern, J=8.3, 2.4 Hz, 1H), 5.74 (s, 1H), 4.21 (br s, 2H), 3.94 (br s, 2H), 3.84 (s, 3H), 3.81 (s, 3H), 3.7-3.8 (m, 1H), 3.23 (dd, J=13, 4 Hz, 1H), 2.95-3.06 (m, 1H), 2.52-2.62 (m, 1H), 1.80-1.95 (m, 1H), 1.6-1.69 (m, 1H, assumed; partially obscured by water peak), 1.28 (d, J=6.0 Hz, 3H).

Step 7. Synthesis of N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide (C40)

2,4,6-Tripropyl-1,3,5,2,4,6-trioxatriphosphinane 2,4,6-trioxide (50% solution by weight in ethyl acetate, 88.4 mL, 148 mmol) was added to a mixture of C38 (12.1 g, 59.6 mmol) and triethylamine (20.6 mL, 148 mmol) in ethyl acetate (80 mL), and the reaction mixture was heated at 65° C. for 20 minutes. Compound C39 (20.0 g, 37.1 mmol) was introduced, and stirring was continued at 65° C. for 1 hour. The reaction mixture was then cooled to room temperature and diluted with ethyl acetate (100 mL); the resulting solution was washed sequentially with water (2×150 mL), saturated aqueous sodium bicarbonate solution (250 mL), and saturated aqueous sodium chloride solution (250 mL), dried over sodium sulfate, filtered, and concentrated under reduced pressure. The resulting solid was dissolved in dichloromethane (1.5 L) and treated with trifluoroacetic acid (140 mL); the reaction mixture was allowed to stir at room temperature for 16 hours, whereupon it was basified to pH 8 with saturated aqueous sodium bicarbonate solution (~1 L). The aqueous layer was extracted with dichloromethane (2×250 mL), and the combined organic layers were washed with saturated aqueous sodium chloride solution (1 L), dried over sodium sulfate, filtered, and concentrated in vacuo. The residue was purified using chromatography on silica gel (Gradient: 0% to 5% methanol in dichloromethane) to afford a solid (24 g), which was triturated with ethyl acetate (100 mL) to provide the product as a white solid (21.3 g). By $^1$H NMR analysis, this material contained ethyl acetate. Yield, corrected for solvent: 19.3 g, 33.6 mmol, 91%. $^1$H NMR (400 MHz, CDCl$_3$) δ 10.62 (s, 1H), 8.34 (br d, J=2.6 Hz, 1H), 8.00-8.26 (v br s, 2H), 7.75 (s, 1H), 7.51-7.58 (m, 1H), 7.41-7.51 (m, 3H), 6.64 (t, $J_{HF}$=72.1 Hz, 1H), 3.93-4.02 (m, 2H), 3.74-3.84 (m, 1H), 3.20 (br dd, J=13, 4 Hz, 1H), 3.00-3.10 (m, 1H), 2.84 (s, 3H), 2.61 (br dd, J=13, 2.6 Hz, 1H), 1.84-1.98 (m, 1H), 1.64-1.72 (m, 1H), 1.31 (d, J=6.1 Hz, 3H).

Step 8. Synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide (45)

A solution of C40 (21.0 g, 36.6 mmol) in xylenes (110 mL) was placed in a pressure tube and treated with SiliCycle, SiliaMetS® diamine (70.0 g, 110 mmol); the tube was sealed and stirred at room temperature for 5 minutes before being placed in a 135° C. oil bath. After stirring for 16 hours, the reaction mixture was cooled to room temperature over 20 minutes. Dichloromethane (10 mL) was added, and the mixture was filtered through diatomaceous earth, followed by rinsing of the filter pad with dichloromethane (3×100 mL). Concentration of the combined filtrates under reduced pressure provided a clear oil, which was seeded with a crystal of the product. The mixture immediately became heterogeneous, and the solid was collected via filtration, washed with toluene (2×25 mL), and stirred in diethyl ether (100 mL) for 30 minutes. Filtration and washing of the collected solid with cold diethyl ether (2×100 mL) afforded the product as a white solid (12.8 g). The combined filtrates were concentrated in vacuo, and the residue was filtered; the isolated solid was stirred with diethyl ether (50 mL) for 30 minutes, then filtered and washed with cold diethyl ether (2×100 mL). This provided additional product, as an off-white solid (3.3 g). Combined yield: 16.1 g, 34.3 mmol, 94%. LCMS m/z 470.5 [M+H]$^+$. $^1$H NMR (400 MHz, CDCl$_3$) δ 10.57 (br s, 1H), 8.32 (br d, J=2 Hz, 1H), 7.68 (s, 1H), 7.42 (br d, J=2 Hz, 1H), 6.63 (t, $J_{HF}$=72.2 Hz, 1H), 4.51-4.59 (br s, 2H), 3.91 (AB quartet, $J_{AB}$=11.0 Hz, $\Delta v_{AB}$=32.5 Hz, 2H), 3.70-3.80 (m, 1H), 3.18 (dd, J=12.5, 4.0 Hz, 1H), 2.84 (s, 3H), 2.80-2.88 (m, 1H), 2.59 (dd, J=12.6, 2.8 Hz, 1H), 1.75-1.86 (m, 1H), 1.54 (ddd, J=13, 4, 2 Hz, 1H), 1.29 (d, J=6.2 Hz, 3H).

Generation of Crystalline Example 45

A sample of Example 45 (94.0 mg, 0.200 mmol) was mixed with propan-2-yl acetate (1.0 mL) and heated to 55° C. The fine suspension was stirred at 55° C. to 60° C. for 2 hours, then allowed to cool to room temperature and stir for 1 hour. Filtration, followed by washing of the filter cake with propan-2-yl acetate, provided Example 45 as an off-white solid. This material was crystalline by powder X-ray diffraction analysis. Yield: 60 mg, 0.13 mmol, 64%. $^1$H NMR (400 MHz, DMSO-d$_6$) δ 10.81 (s, 1H), 8.42 (d, J=2.2 Hz, 1H), 7.72 (d, J=2 Hz, 1H), 7.62 (s, 1H), 7.44 (t, $J_{HF}$=73.0 Hz, 1H), 6.25 (br s, 2H), 3.68 (s, 2H), 3.57-3.66 (m, 1H), 2.85-2.94 (m, 1H), 2.60-2.70 (m, 5H), 1.49-1.66 (m, 2H), 1.14 (d, J=6.0 Hz, 3H).

Method A

Synthesis of N-{2-[(4aR,6S, 8aR)-2-amino-6-methyl-4,4a,5,6-tetrahydropyrano[3,4-d][1,3]thiazin-8a(8H)-yl]-1,3-thiazol-4-yl}amides Via N-Acylation of P2 Followed by Selective Hydrolysis

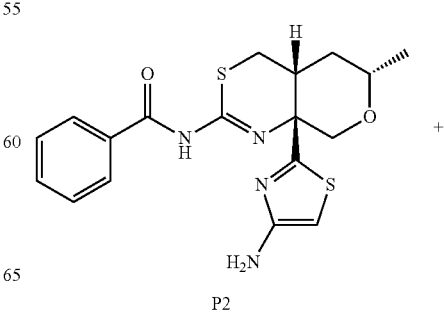

P2

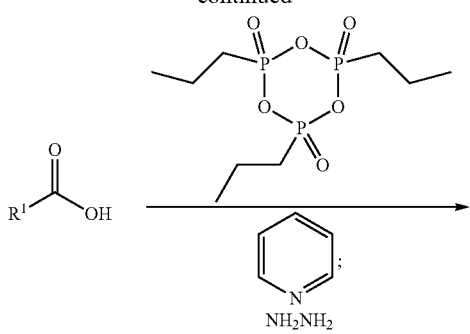

A solution of P2 (25.2 mg, 64.9 µmol) in ethyl acetate (0.5 mL) was added to the appropriate carboxylic acid (78 µmol). 2,4,6-Tripropyl-1,3,5,2,4,6-trioxatriphosphinane 2,4,6-trioxide (50% weight solution in ethyl acetate, 0.26 mL, 0.13 mmol) and pyridine (21 uL, 0.26 mmol) were added, and the reaction mixture was shaken at room temperature for 16 hours. It was then partitioned between water (1.5 mL) and ethyl acetate (2.4 mL) with vortexing. The organic layer was passed through a solid-phase extraction cartridge (6 mL) charged with sodium sulfate (~1 g); this extraction procedure was repeated twice. The combined eluents were concentrated in vacuo, dissolved in ethanol (0.75 mL), treated with hydrazine monohydrate (51 µL, 1.0 mmol) and shaken at room temperature for 6 hours. After removal of solvent in vacuo, the product was purified via reversed phase HPLC using one of the following methods: 1) Column: Waters XBridge C18, 5 µm; Mobile phase A: 0.03% ammonium hydroxide in water (v/v); Mobile phase B: 0.03% ammonium hydroxide in acetonitrile (v/v); Gradient: [5% or 10%] to 100% B. 2) Waters Sunfire C18, 5 µm; Mobile phase A: 0.05% trifluoroacetic acid in water (v/v); Mobile phase B: 0.05% trifluoroacetic acid in acetonitrile (v/v); Gradient: 5% to 100% B.

Method B

Alternate synthesis of N-{2-[(4aR,6S,8aR)-2-amino-6-methyl-4,4a,5,6-tetrahydropyrano[3,4-d][1,3]thiazin-8a(8H)-yl]-1,3-thiazol-4-yl}amides Via N-Acylation of P2 Followed by Selective Hydrolysis

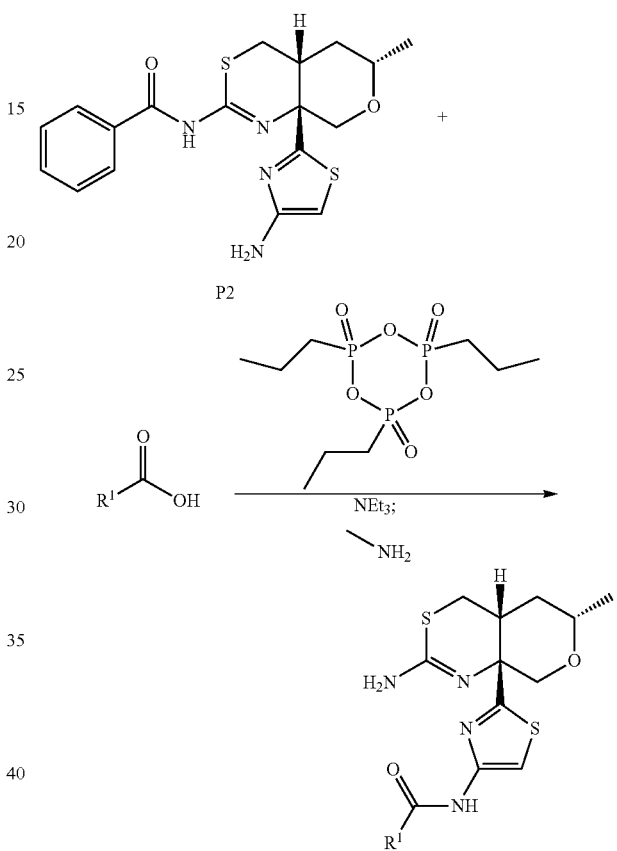

A solution of P2 (46.6 mg, 0.120 mmol) in ethyl acetate (1.5 mL) was added to the appropriate carboxylic acid (0.12 mmol), and the mixture was cooled in a dry ice box. Triethylamine (70 µL, 0.50 mmol) and 2,4,6-tripropyl-1,3,5,2,4,6-trioxatriphosphinane 2,4,6-trioxide (50% weight solution in ethyl acetate, 0.14 mL, 0.24 mmol) were added, and the reaction mixture was allowed to warm to ambient temperature, then shaken at room temperature for 3 to 6 hours. It was then partitioned between half-saturated aqueous sodium bicarbonate solution (1.5 mL) and ethyl acetate (2.4 mL) with vortexing. The organic layer was passed through a solid-phase extraction cartridge (6 mL) charged with sodium sulfate (~1 g); this extraction procedure was repeated twice. The combined eluents were concentrated in vacuo, dissolved in ethanol (0.5 mL), treated with a solution of methylamine in ethanol (33% by weight, 0.5 mL, 4 mmol), and shaken at room temperature for 3 hours. After removal of solvent in vacuo, the product was purified via reversed phase HPLC (Column: Waters XBridge C18, 5 µm; Mobile phase A: 0.03% ammonium hydroxide in water (v/v); Mobile phase B: 0.03% ammonium hydroxide in acetonitrile (v/v); Gradient: 5% to [40% or 100%] B).

TABLE 1

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 9 | Example 2 | 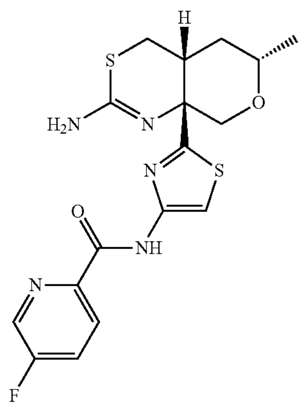 [SMILES: C[C@H]1C[C@H]2CSC(N)=N[C@@]2(c2nc(NC(=O)c3ccc(F)cn3)cs2)CO1] | 10.37 (br s, 1H), 8.47 (br d, J = 2.8 Hz, 1H), 8.32 (ddd, J = 8.7, 4.6, 0.5 Hz, 1H), 7.71 (s, 1H), 7.60 (ddd, J = 8.7, 8.0, 2.8 Hz, 1H), 3.91 (AB quartet, J$_{AB}$ = 11.1 Hz, Δv$_{AB}$ = 38.0 Hz, 2H), 3.75 (dqd, J = 11.2, 6.1, 2.3 Hz, 1H), 3.17 (dd, J = 12.5, 4.0 Hz, 1H), 2.80-2.88 (m, 1H), 2.59 (dd, J = 12.5, 2.8 Hz, 1H), 1.81 (ddd, J = 13, 13, 11.4 Hz, 1H), 1.54 (ddd, J = 13.4, 4.2, 2.4 Hz, 1H), 1.29 (d, J = 6.2 Hz, 3H); 408.3 |
| 10 | Example 2 | 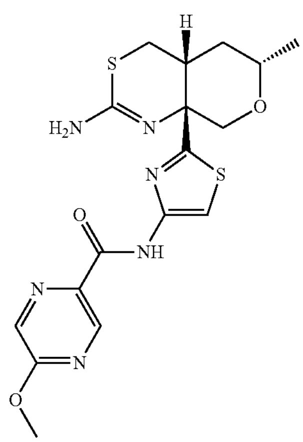 [SMILES: COc1cnc(C(=O)Nc2csc([C@]34CO[C@@H](C)C[C@H]3CSC(N)=N4)n2)cn1] | 10.11 (br s, 1H), 9.01 (s, 1H), 8.17 (s, 1H), 7.71 (s, 1H), 4.07 (s, 3H), 3.92 (AB quartet, J$_{AB}$ = 11.2 Hz, Δv$_{AB}$ = 46.6 Hz, 2H), 3.69-3.79 (m, 1H), 3.18 (dd, J = 12.5, 3.7 Hz, 1H), 2.80-2.89 (m, 1H), 2.60 (br dd, J = 12.6, 2 Hz, 1H), 1.74-1.87 (m, 1H), 1.51-1.59 (m, 1H), 1.29 (d, J = 6.1 Hz, 3H); 421.3 |
| 11 | Example 4 | 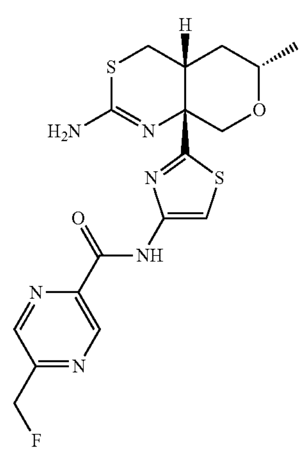 [SMILES: C[C@H]1C[C@H]2CSC(N)=N[C@@]2(c2nc(NC(=O)c3cnc(CF)cn3)cs2)CO1] | 10.27 (br s, 1H), 9.44 (s, 1H), 8.76 (s, 1H), 7.76 (s, 1H), 5.67 (d, J$_{HF}$ = 46.4 Hz, 2H), 3.91 (AB quartet, J$_{AB}$ = 11.2 Hz, Δv$_{AB}$ = 39.4 Hz, 2H), 3.69-3.80 (m, 1H), 3.17 (dd, J = 12, 4 Hz, 1H), 2.78-2.88 (m, 1H), 2.55-2.64 (m, 1H), 1.75-1.88 (m, 1H), 1.50-1.59 (m, 1H), 1.30 (d, J = 6.0 Hz, 3H); 423.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 12 | Example 4 | 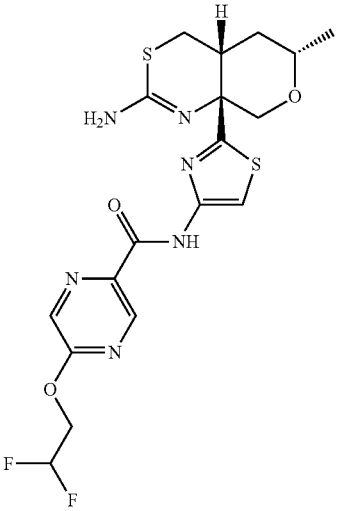 [SMILES: C[C@H]1C[C@H]2CSC(N)=N[C@@]2(c2nc(NC(=O)c3cnc(OCC(F)F)cn3)cs2)CO1] | 10.11 (br s, 1H), 9.01 (d, J = 1.0 Hz, 1H), 8.28 (d, J = 1.0 Hz, 1H), 7.75 (s, 1H), 6.17 (tt, J = 55, 4 Hz, 1H), 4.67 (td, J = 13.4, 3.9 Hz, 2H), 4.10 (d, J = 11.7 Hz, 1H), 3.85 (d, J = 11.5 Hz, 1H), 3.70-3.80 (m, 1H), 3.20 (dd, J = 12.6, 3.6 Hz, 1H), 2.87-2.96 (m, 1H), 2.63 (dd, J = 13, 2 Hz, 1H), 1.74-1.87 (m, 1H), 1.54-1.63 (m, 1H), 1.31 (d, J = 6.2 Hz, 3H); 493.0 [M + Na]$^+$ |
| 13 | Example 4 | 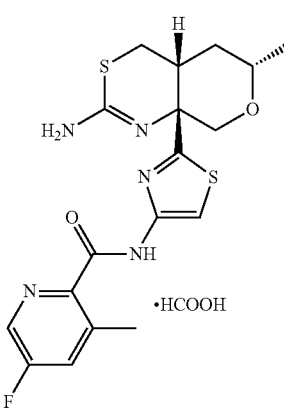 | 10.55 (br s, 1H), 8.32 (d, J = 2.5 Hz, 1H), 7.71 (s, 1H), 7.35-7.41 (m, 1H), 4.11 (d, J = 11.7 Hz, 1H), 3.86 (d, J = 11.7 Hz, 1H), 3.71-3.81 (m, 1H), 3.21 (dd, J = 13, 4 Hz, 1H), 2.91-2.99 (m, 1H), 2.84 (s, 3H), 2.63 (dd, J = 13, 2 Hz, 1H), 1.74-1.86 (m, 1H), 1.55-1.63 (m, 1H), 1.31 (d, J = 6.0 Hz, 3H); 422.0 |
| 14 | Example 4 | 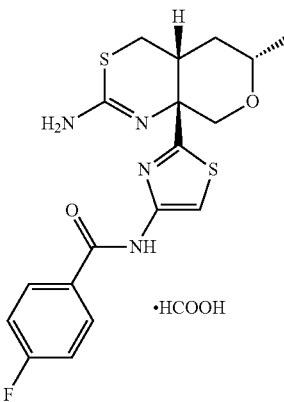 | $^1$H NMR (400 MHz, CD$_3$OD) δ 8.48 (br s, 1H), 7.98-8.05 (m, 2H), 7.77 (s, 1H), 7.25 (br dd, J = 8.8, 8.8 Hz, 2H), 3.98 (AB quartet, J$_{AB}$ = 11.9 Hz, Δν$_{AB}$ = 8.8 Hz, 2H), 3.74-3.84 (m, 1H), 3.15 (dd, J = 12.9, 4.0 Hz, 1H), 3.02-3.09 (m, 1H), 2.85 (dd, J = 12.8, 2.6 Hz, 1H), 1.62-1.77 (m, 2H), 1.26 (d, J = 6.2 Hz, 3H); 406.9 |

TABLE 1-continued

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 15 | Example 4$^1$ | 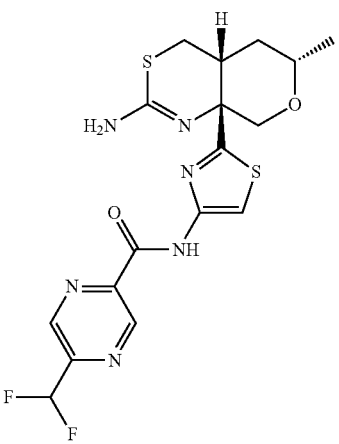 [SMILES: C[C@H]1C[C@H]2CSC(N)=N[C@@]2(c2nc(NC(=O)c3cnc(C(F)F)cn3)cs2)CO1] | 10.25 (br s, 1H), 9.52 (br s, 1H), 8.94 (br s, 1H), 7.77 (s, 1H), 6.80 (t, $J_{HF}$ = 54.4 Hz, 1H), 4.5-4.7 (br s, 2H), 3.91 (AB quartet, $J_{AB}$ = 11.1 Hz, $\Delta\nu_{AB}$ = 39.2 Hz, 2H), 3.70-3.80 (m, 1H), 3.17 (dd, J = 12.6, 4.1 Hz, 1H), 2.79-2.87 (m, 1H), 2.61 (dd, J = 12.6, 2.8 Hz, 1H), 1.76-1.87 (m, 1H), 1.52-1.59 (m, 1H), 1.30 (d, J = 6.2 Hz, 3H); 441.0 |
| 16 | Example 4$^1$ | 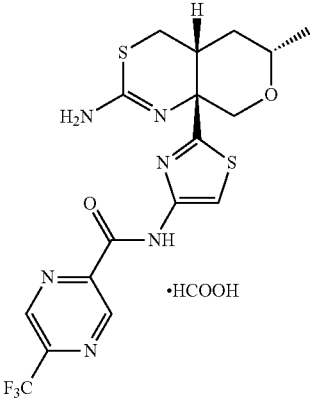 [SMILES: C[C@H]1C[C@H]2CSC(N)=N[C@@]2(c2nc(NC(=O)c3cnc(C(F)(F)F)cn3)cs2)CO1 ; "·HCOOH"] | $^1$H NMR (400 MHz, CD$_3$OD) δ 9.49 (br s, 1H), 9.17 (br s, 1H), 7.84 (s, 1H), 3.91 (AB quartet, $J_{AB}$ = 11.5 Hz, $\Delta\nu_{AB}$ = 22.0 Hz, 2H), 3.73-3.82 (m, 1H), 3.10 (dd, J = 13, 4 Hz, 1H), 2.90-2.98 (m, 1H), 2.74 (dd, J = 13, 3 Hz, 1H), 1.61-1.77 (m, 2H), 1.25 (d, J = 6.3 Hz, 3H); 459.0 |
| 17 | Example 4 | 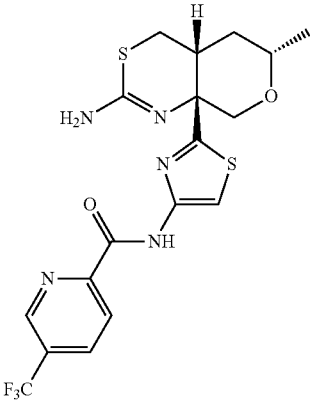 [SMILES: C[C@H]1C[C@H]2CSC(N)=N[C@@]2(c2nc(NC(=O)c3ccc(C(F)(F)F)cn3)cs2)CO1] | 10.49 (br s, 1H), 8.90 (br s, 1H), 8.43 (d, J = 8.3 Hz, 1H), 8.18 (br d, J = 8 Hz, 1H), 7.76 (s, 1H), 4.46-4.82 (br s, 2H), 3.92 (AB quartet, $J_{AB}$ = 11.2 Hz, $\Delta\nu_{AB}$ = 36.1 Hz, 2H), 3.71-3.81 (m, 1H), 3.18 (dd, J = 12.7, 4.1 Hz, 1H), 2.81-2.89 (m, 1H), 2.57-2.64 (m, 1H), 1.76-1.87 (m, 1H), 1.52-1.59 (m, 1H), 1.30 (d, J = 6.0 Hz, 3H); 458.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 18 | Example 4 | 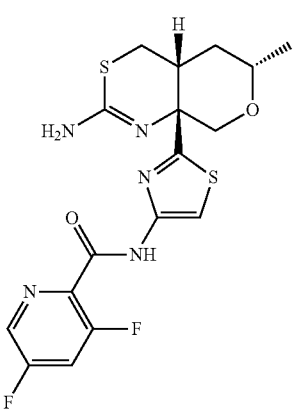 [SMILES: C[C@H]1C[C@H]2CSC(N)=N[C@@]2(c2nc(NC(=O)c3ncc(F)cc3F)cs2)CO1] | 10.21 (br s, 1H), 8.35-8.39 (m, 1H), 7.74 (s, 1H), 7.37-7.44 (m, 1H), 4.4-4.9 (br s, 2H), 3.91 (AB quartet, J$_{AB}$ = 11.1 Hz, Δν$_{AB}$ = 40.3 Hz, 2H), 3.69-3.79 (m, 1H), 3.17 (dd, J = 12.7, 3.7 Hz, 1H), 2.78-2.86 (m, 1H), 2.59 (dd, J = 12.4, 2.6 Hz, 1H), 1.75-1.87 (m, 1H), 1.50-1.58 (m, 1H), 1.29 (d, J = 6.0 Hz, 3H); 425.9 |
| 19 | Example 4 | 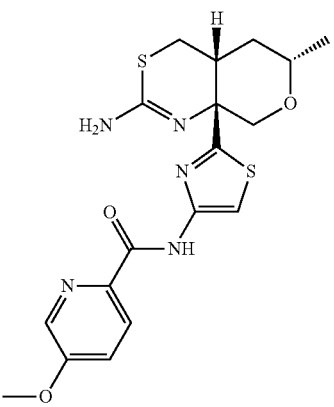 | 10.40 (br s, 1H), 8.26-8.30 (m, 1H), 8.23 (d, J = 8.3 Hz, 1H), 7.69 (s, 1H), 7.31-7.37 (m, 1H), 4.4-4.9 (br s, 2H), 3.95 (s, 3H), 3.93-3.99 (m, 1H), 3.87 (d, half of AB quartet, J = 11.0 Hz, 1H), 3.69-3.80 (m, 1H), 3.13-3.22 (m, 1H), 2.80-289 (m, 1H), 2.54-2.62 (m, 1H), 1.74-1.87 (m, 1H), 1.50-1.58 (m, 1H), 1.29 (d, J = 6.0 Hz, 3H); 441.9 [M + Na]$^+$ |
| 20 | Example 4 | 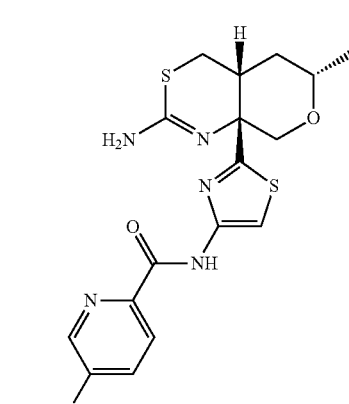 | 10.40 (br s, 1H), 8.52-8.57 (m, 1H), 8.36 (d, J = 8.8 Hz, 1H), 7.77 (br d, J = 9 Hz, 1H), 7.72 (s, 1H), 4.45-4.85 (br s, 2H), 3.91 (AB quartet, J$_{AB}$ = 11.1 Hz, Δν$_{AB}$ = 38.1 Hz, 2H), 3.70-3.80 (m, 1H), 3.17 (dd, J = 12.6, 4.0 Hz, 1H), 2.80-2.88 (m, 1H), 2.60 (dd, J = 12.6, 2.3 Hz, 1H), 1.75-1.87 (m, 1H), 1.51-1.59 (m, 1H), 1.30 (d, J = 6.2 Hz, 3H); 474.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 21 | Example 4 | 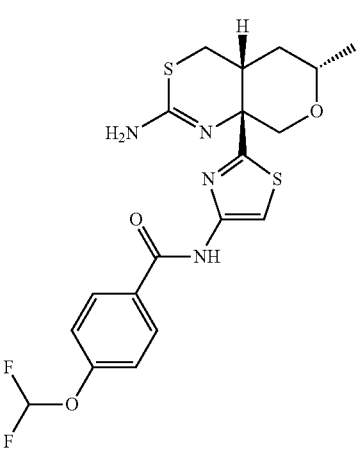 [SMILES: C[C@H]1C[C@H]2CSC(N)=N[C@@]2(c2nc(NC(=O)c3ccc(OC(F)F)cc3)cs2)CO1] | 8.66 (br s, 1H), 7.94 (br d, J = 8.7 Hz, 2H), 7.70 (s, 1H), 7.24 (br d, J = 8.7 Hz, 2H), 6.61 (t, J$_{HF}$ = 73.0 Hz, 1H), 4.4-4.9 (br s, 2H), 3.89 (AB quartet, J$_{AB}$ = 11.2 Hz, Δν$_{AB}$ = 49.6 Hz, 2H), 3.68-3.78 (m, 1H), 3.16 (dd, J = 12.5, 4.0 Hz, 1H), 2.71-2.80 (m, 1H), 2.56-2.63 (m, 1H), 1.75-1.87 (m, 1H), 1.50-1.58 (m, 1H), 1.29 (d, J = 6.0 Hz, 3H); 476.9 [M + Na]$^+$ |
| 22 | Example 4 | 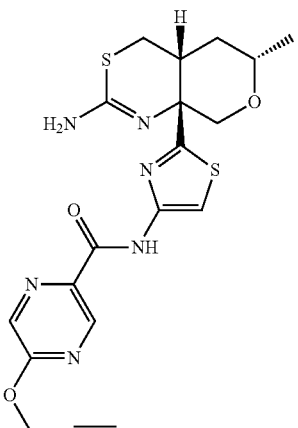 | 10.10 (br s, 1H), 9.03 (d, J = 1.0 Hz, 1H), 8.21 (d, J = 1.0 Hz, 1H), 7.70 (s, 1H), 5.06 (br q, J = 2.3 Hz, 2H), 4.45-4.75 (br s, 2H), 3.90 (AB quartet, J$_{AB}$ = 11.1 Hz, Δν$_{AB}$ = 39.8 Hz, 2H), 3.69-3.79 (m, 1H), 3.17 (dd, J = 12.4, 4.0 Hz, 1H), 2.79-2.87 (m, 1H), 2.59 (dd, J = 12.5, 2.4 Hz, 1H), 1.90 (t, J = 2.3 Hz, 3H), 1.75-1.86 (m, 1H), 1.50-1.58 (m, 1H), 1.29 (d, J = 6.2 Hz, 3H); 481.0 [M + Na]$^+$ |
| 23 | Example 4 | 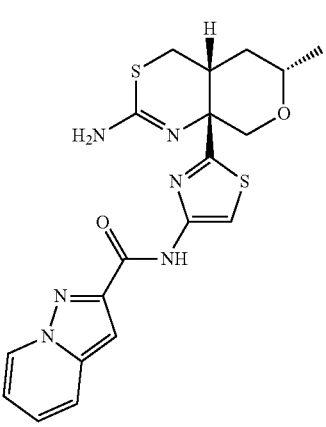 [SMILES: C[C@H]1C[C@H]2CSC(N)=N[C@@]2(c2nc(NC(=O)c3cc4ccccn4n3)cs2)CO1] | 9.64 (br s, 1H), 8.44 (d, J = 7.0 Hz, 1H), 7.70 (s, 1H), 7.64 (d, J = 9.0 Hz, 1H), 7.19 (dd, J = 8.5, 7.3 Hz, 1H), 7.16 (s, 1H), 6.92 (dd, J = 7, 7 Hz, 1H), 4.45-4.85 (br s, 2H), 3.91 (AB quartet, J$_{AB}$ = 11.1 Hz, Δν$_{AB}$ = 38.8 Hz, 2H), 3.69-3.80 (m, 1H), 3.18 (dd, J = 12.5, 3.8 Hz, 1H), 2.79-2.87 (m, 1H), 2.59 (dd, J = 12.7, 2.4 Hz, 1H), 1.75-1.87 (m, 1H), 1.50-1.58 (m, 1H), 1.30 (d, J = 6.0 Hz, 3H); 428.9 |

TABLE 1-continued

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 24 | Example 4 | 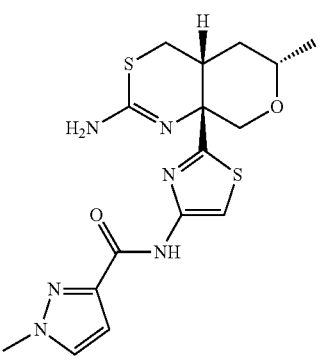 | 9.38 (br s, 1H), 7.63 (s, 1H), 7.42 (d, J = 2.1 Hz, 1H), 6.88 (d, J = 2.3 Hz, 1H), 3.97 (s, 3H), 3.94-3.98 (m, 1H), 3.85 (d, half of AB quartet, J = 11.0 Hz, 1H), 3.69-3.78 (m, 1H), 3.17 (dd, J = 12.6, 4.0 Hz, 1H), 2.78-2.86 (m, 1H), 2.58 (dd, J = 12.6, 2.8 Hz, 1H), 1.74-1.86 (m, 1H), 1.54 (ddd, J = 13.3, 4.0, 2.4 Hz, 1H), 1.29 (d, J = 6.2 Hz, 3H); 392.9 |
| 25 | Example 4 | 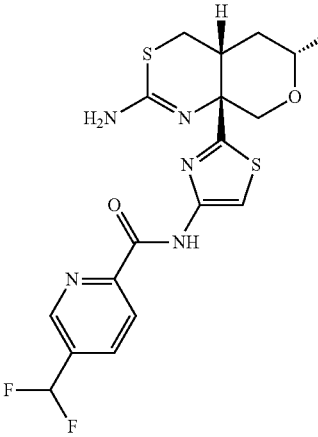 | 10.52 (br s, 1H), 8.78 (br s, 1H), 8.39 (d, J = 8.0 Hz, 1H), 8.08 (br d, J = 8 Hz, 1H), 7.76 (s, 1H), 6.82 (t, $J_{HF}$ = 55.7 Hz, 1H), 4.55-4.95 (br s, 2H), 3.93 (AB quartet, $J_{AB}$ = 11.3 Hz, $\Delta v_{AB}$ = 41.3 Hz, 2H), 3.71-3.81 (m, 1H), 3.15-3.22 (m, 1H), 2.82-2.91 (m, 1H), 2.57-2.64 (m, 1H), 1.75-1.87 (m, 1H), 1.52-1.59 (m, 1H), 1.30 (d, J = 6.4 Hz, 3H); 439.9 |
| 26 | Example 4$^2$ | 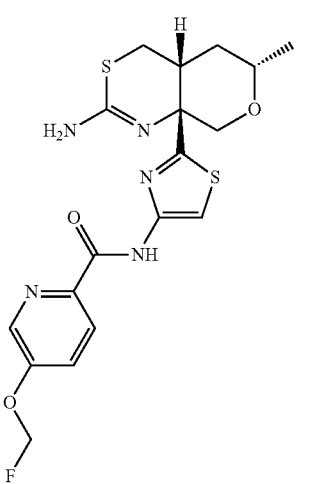 [SMILES: C[C@H]1C[C@H]2CSC(N)=N[C@@]2(c2nc(NC(=O)c3ccc(OCF)cn3)cs2)CO1] | 10.40 (br s, 1H), 8.43 (d, J = 2.3 Hz, 1H), 8.28 (d, J = 8.5 Hz, 1H), 7.71 (s, 1H), 7.56-7.61 (m, 1H), 5.82 (d, $J_{HF}$ = 53.5 Hz, 2H), 4.5-4.85 (br s, 2H), 3.92 (AB quartet, $J_{AB}$ = 11.1 Hz, $\Delta v_{AB}$ = 38.5 Hz, 2H), 3.70-3.80 (m, 1H), 3.18 (dd, J = 12.6, 4.0 Hz, 1H), 2.81-2.89 (m, 1H), 2.56-2.63 (m, 1H), 1.75-1.87 (m, 1H), 1.51-1.58 (m, 1H), 1.30 (d, J = 6.2 Hz, 3H); 437.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 27 | Example 4 | 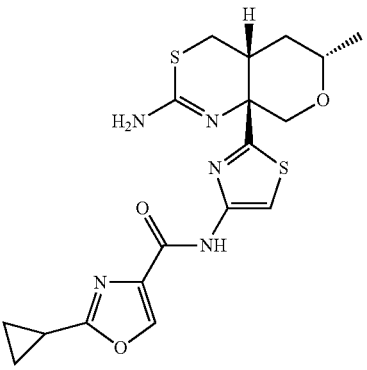 [SMILES: C[C@H]1C[C@H]2CSC(N)=N[C@@]2(c2nc(NC(=O)c3coc(C4CC4)n3)cs2)CO1] | 9.32 (br s, 1H), 8.12 (s, 1H), 7.63 (s, 1H), 4.45-4.85 (br s, 2H), 3.90 (AB quartet, J$_{AB}$ = 11.1 Hz, Δν$_{AB}$ = 42.4 Hz, 2H), 3.70-3.79 (m, 1H), 3.16 (dd, J = 12.5, 3.7 Hz, 1H), 2.77-2.86 (m, 1H), 2.55-2.63 (m, 1H), 2.05-2.13 (m, 1H), 1.74-1.86 (m, 1H), 1.50-1.58 (m, 1H), 1.29 (d, J = 6.2 Hz, 3H), 1.09-1.17 (m, 4H); 441.9 [M + Na]$^+$ |
| 28 | Method A; P2 | 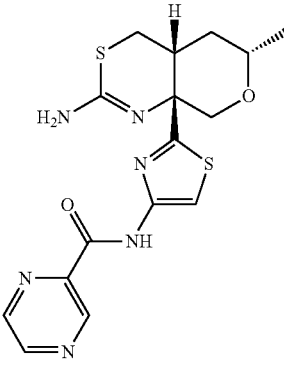 | 1.48 minutes$^3$; 391.0 |
| 29 | Method A; P2 | 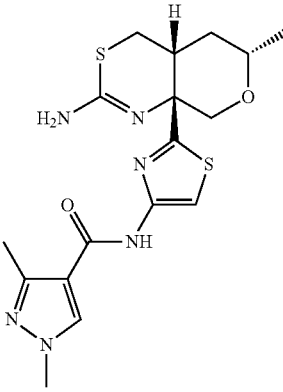 | 1.42 minutes$^3$; 407.1 |

TABLE 1-continued

Method of Preparation, Structure, and Physicochemical Data for Examples 9-58 and 87-109

| Example Number | Method of Preparation; Non-commercial starting materials | Structure | $^{1}$H NMR (400 MHz, CDCl$_{3}$) δ (ppm); Mass spectrum, observed ion m/z (M + H$^{+}$) or HPLC retention time; Mass spectrum m/z [M + H]$^{+}$ (unless otherwise indicated) |
|---|---|---|---|
| 30 | Method A; P2 | 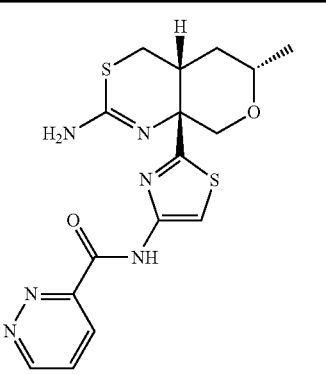 | 1.42 minutes[3]; 391.0 |
| 31 | Method A; P2 | 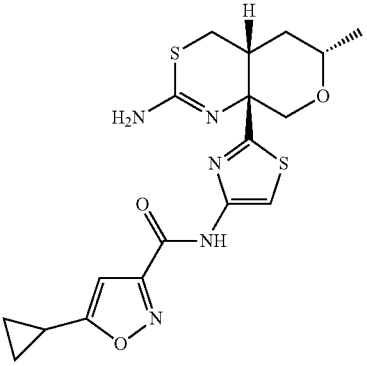 [SMILES: C[C@H]1C[C@H]2CSC(N)=N[C@@]2(c2nc(NC(=O)c3cc(C4CC4)on3)cs2)CO1] | 2.04 minutes[3]; 420.0 |
| 32 | Method A; P2[4] | 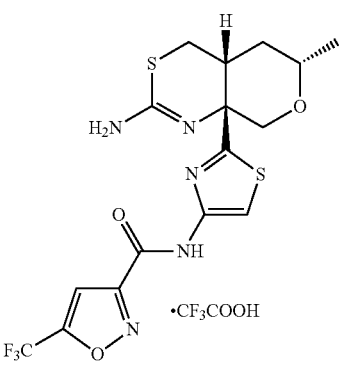 [SMILES: C[C@H]1C[C@H]2CSC(N)=N[C@@]2(c2nc(NC(=O)c3cc(C(F)(F)F)on3)cs2)CO1 ; "·CF3COOH"] | 2.11 minutes[3]; 448.1 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 33 | Method A; P2 | 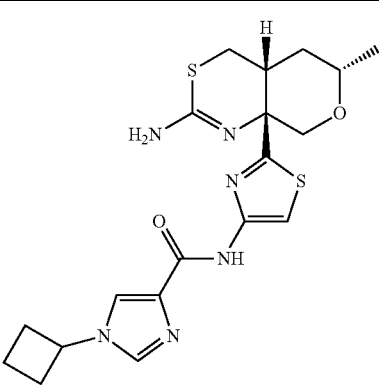 | 1.54 minutes$^3$; 433.1 |
| 34 | Method A; P2$^5$ | 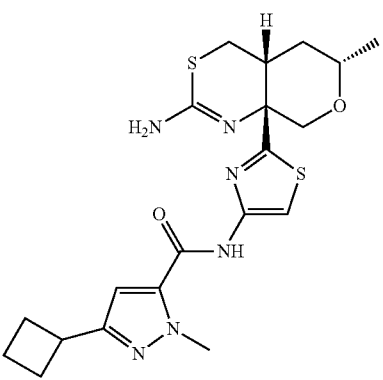 [SMILES: C[C@H]1C[C@H]2CSC(N)=N[C@@]2(c2nc(NC(=O)c3cc(C4CCC4)nn3C)cs2)CO1] | 2.08 minutes$^3$; 447.1 |
| 35 | Method A; P2 | 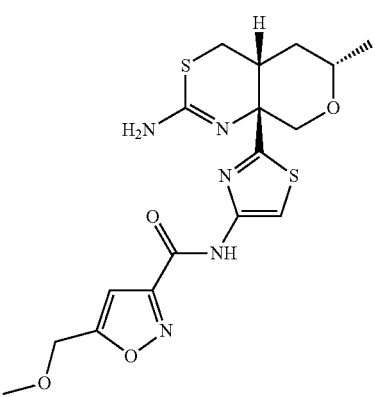 | 1.68 minutes$^3$; 424.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 36 | Method A; P2 | 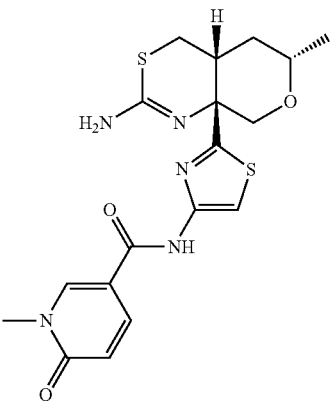 | 1.30 minutes$^3$; 420.0 |
| 37 | Example 4$^6$ | 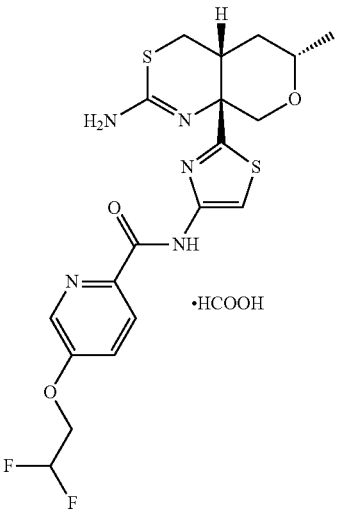 [SMILES: C[C@H]1C[C@H]2CSC(N)=N[C@@]2(c2nc(NC(=O)c3ccc(OCC(F)F)cn3)cs2)CO1 ; "·HCOOH"] | 10.38 (br s, 1H), 8.33 (d, J = 2 Hz, 1H), 8.26 (d, J = 8.4 Hz, 1H), 7.74 (s, 1H), 7.36-7.42 (m, 1H), 6.16 (tt, J = 55, 4 Hz, 1H), 4.33 (td, J = 12.8, 3.8 Hz, 2H), 4.15 (d, J = 11.7 Hz, 1H), 3.86 (d, J = 11.7 Hz, 1H), 3.71-3.81 (m, 1H), 3.22 (dd, J = 13, 4 Hz, 1H), 2.93-3.02 (m, 1H), 2.64 (br d, J = 13 Hz, 1H), 1.75-1.87 (m, 1H), 1.56-1.64 (m, 1H), 1.32 (d, J = 5.9 Hz, 3H); 469.9 |
| 38 | Method A; P2 | 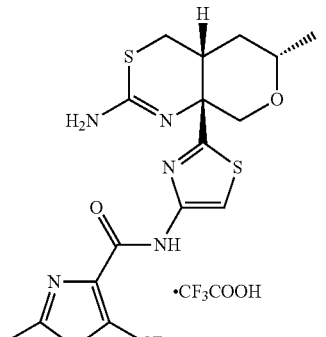 | 2.08 minutes$^3$; 462.1 |

… TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 39 | Method A; P2 | 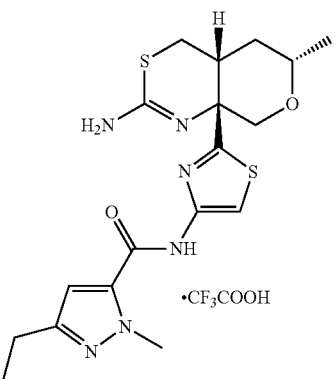 [SMILES: CCc1cc(C(=O)Nc2csc([C@]34CO[C@@H](C)C[C@H]3CSC(N)=N4)n2)n(C)n1 ; "·CF3COOH"] | 1.78 minutes$^3$; 421.2 |
| 40 | Method A; P2$^7$ | 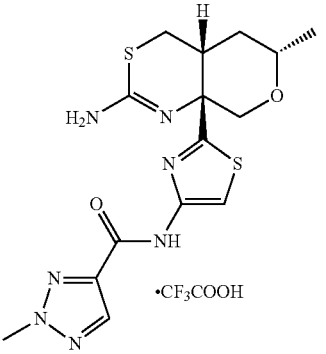 | 1.43 minutes$^3$; 394.2 |
| 41 | Method A; P2 | 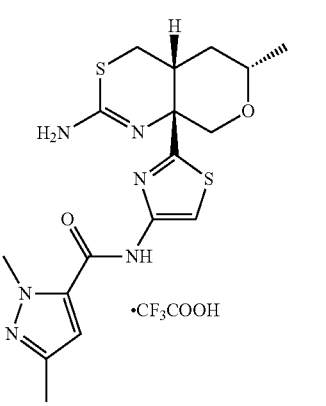 | 1.60 minutes$^3$; 407.2 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 42 | Method A; P2 | 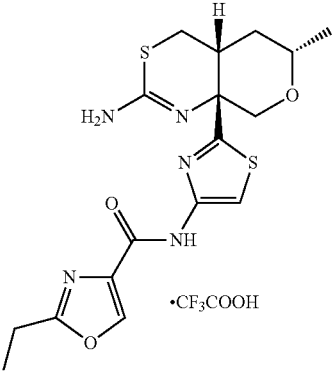 [SMILES: CCc1nc(C(=O)Nc2csc([C@]34CO[C@@H](C)C[C@H]3CSC(N)=N4)n2)co1 ; "·CF3COOH"] | 1.80 minutes$^3$; 408.2 |
| 43 | Method A; P2 | 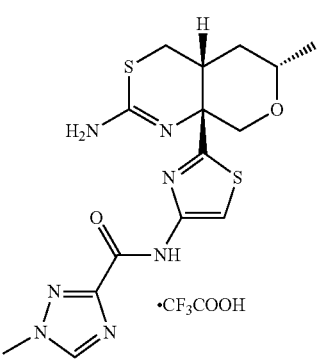 | 1.25 minutes$^3$; 394.2 |
| 44 | Example 1$^{8,9}$ | 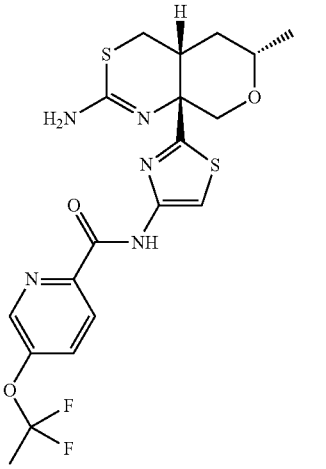 [SMILES: C[C@H]1C[C@H]2CSC(N)=N[C@@]2(c2nc(NC(=O)c3ccc(OC(C)(F)F)cn3)cs2)CO1] | $^1$H NMR (400 MHz, DMSO-d$_6$) δ 10.59 (br s, 1H), 8.61 (d, J = 2.1 Hz, 1H), 8.22 (d, J = 8.7 Hz, 1H), 7.92-7.98 (m, 1H), 7.64 (s, 1H), 6.28 (br s, 2H), 3.68 (s, 2H), 3.58-3.67 (m, 1H), 2.85-2.93 (m, 1H), 2.62-2.72 (m, 2H), 2.06 (t, J$_{HF}$ = 14.2 Hz, 3H), 1.50-1.65 (m, 2H), 1.14 (d, J = 6.0 Hz, 3H); 469.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 45 | Example 4 | 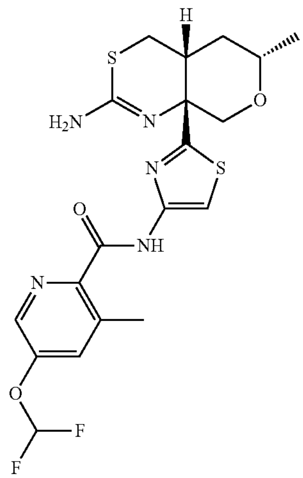 [SMILES: Cc1cc(OC(F)F)cnc1C(=O)Nc1csc([C@]23CO[C@@H](C)C[C@H]2CSC(N)=N3)n1] | 10.57 (br s, 1H), 8.32 (d, J = 2.1 Hz, 1H), 7.68 (s, 1H), 7.40-7.43 (m, 1H), 6.63 (t, J$_{HF}$ = 72.2 Hz, 1H), 4.5-4.65 (br s, 2H), 3.92 (AB quartet, J$_{AB}$ = 11.0 Hz, Δν$_{AB}$ = 33.9 Hz, 2H), 3.70-3.80 (m, 1H), 3.18 (dd, J = 12.4, 4.0 Hz, 1H), 2.84 (s, 3H), 2.80-2.88 (m, 1H), 2.59 (dd, J = 12.5, 2.7 Hz, 1H), 1.75-1.87 (m, 1H), 1.51-1.58 (m, 1H), 1.29 (d, J = 6.2 Hz, 3H); 469.9 |
| 46 | Example 4 | 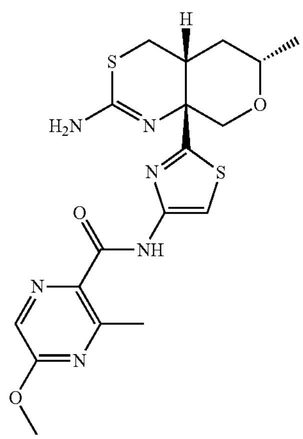 [SMILES: COc1cnc(C(=O)Nc2csc([C@]34CO[C@@H](C)C[C@H]3CSC(N)=N4)n2)c(C)c1] | 10.36 (br s, 1H), 8.02 (s, 1H), 7.67 (s, 1H), 4.52-4.62 (br s, 2H), 4.05 (s, 3H), 3.91 (AB quartet, J$_{AB}$ = 11.1 Hz, Δν$_{AB}$ = 33.7 Hz, 2H), 3.69-3.79 (m, 1H), 3.17 (dd, J = 12.5, 4.0 Hz, 1H), 2.96 (s, 3H), 2.78-2.87 (m, 1H), 2.58 (dd, J = 12.4, 2.6 Hz, 1H), 1.75-1.87 (m, 1H), 1.50-1.57 (m, 1H), 1.29 (d, J = 6.0 Hz, 3H); 434.8 |
| 47 | Example 4 | 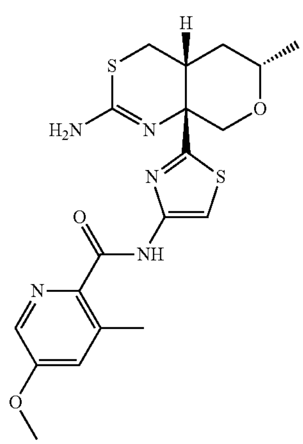 | 10.61 (br s, 1H), 8.13 (d, J = 2.8 Hz, 1H), 7.65 (s, 1H), 7.08 (br d, J = 2.6 Hz, 1H), 4.5-4.7 (br s, 2H), 3.92 (s, 3H), 3.91 (AB quartet, J$_{AB}$ = 11.0 Hz, Δν$_{AB}$ = 30.6 Hz, 2H), 3.70-3.80 (m, 1H), 3.18 (dd, J = 12.4, 4.0 Hz, 1H), 2.81 (br s, 3H), 2.81-2.88 (m, 1H), 2.58 (dd, J = 12.6, 2.8 Hz, 1H), 1.80 (ddd, J = 13.0, 12.8, 11.5 Hz, 1H), 1.53 (ddd, J = 13.4, 4.2, 2.3 Hz, 1H), 1.29 (d, J = 6.2 Hz, 3H); 433.9 |

TABLE 1-continued

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 48 | Example 3[10] | 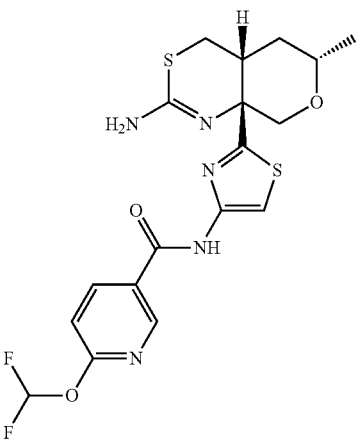 | $^1$H NMR (400 MHz, DMSO-d$_6$) δ 11.57 (s, 1H), 8.87 (d, J = 2.3 Hz, 1H), 8.46 (dd, J = 8.5, 2.3 Hz, 1H), 7.80 (t, J$_{HF}$ = 72.3 Hz, 1H), 7.69 (s, 1H), 7.20 (d, J = 8.5 Hz, 1H), 6.27 (s, 2H), 3.66-3.74 (m, 2H), 3.54-3.65 (m, 1H), 2.84-2.93 (m, 1H), 2.62-2.73 (m, 2H), 1.51-1.66 (m, 2H), 1.15 (d, J = 6.3 Hz, 3H); 455.9 |
| 49 | Example 3[11] | 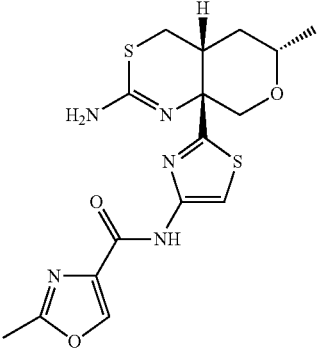 | 9.37 (s, 1H), 8.19 (s, 1H), 7.67 (s, 1H), 4.04 (d, J = 11.7 Hz, 1H), 3.85 (d, J = 11.7 Hz, 1H), 3.74 (dqd, J = 11.5, 5.9, 2.3 Hz, 1H), 3.19 (dd, J = 12.9, 3.9 Hz, 1H), 2.86-2.94 (m, 1H), 2.64 (dd, J = 12.9, 2.7 Hz, 1H), 2.53 (s, 3H), 1.79 (td, J = 12.9, 11.3 Hz, 1H), 1.58 (ddd, J = 13.5, 4.1, 2.3 Hz, 1H), 1.30 (d, J = 6.2 Hz, 3H); 394.0 |
| 50 | Example 3[10] | 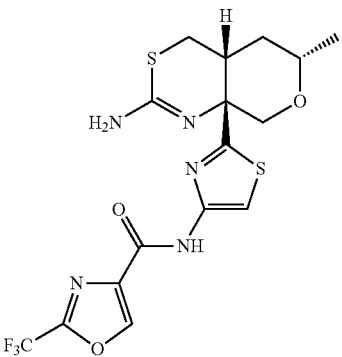 [SMILES: C[C@H]1C[C@H]2CSC(N)=N[C@@]2(c2nc(NC(=O)c3coc(C(F)(F)F)n3)cs2)CO1] | 9.34 (br s, 1H), 8.45 (s, 1H), 7.66 (s, 1H), 4.65 (br s, 2H), 3.94 (d, J = 10.9 Hz, 1H), 3.83 (d, J = 11.0 Hz, 1H), 3.68-3.78 (m, 1H), 3.15 (dd, J = 12.4, 4.0 Hz, 1H), 2.78-2.86 (m, 1H), 2.60 (dd, J = 12.5, 2.6 Hz, 1H), 1.75-1.86 (m, 1H), 1.51-1.58 (m, 1H), 1.29 (d, J = 6.1 Hz, 3H); 448.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 51 | Example 3[10] | 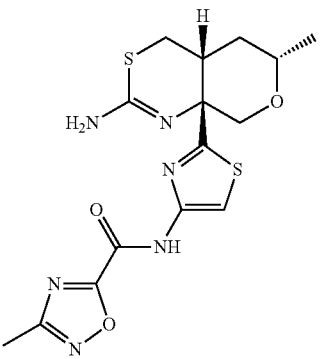 | $^1$H NMR (400 MHz, DMSO-d$_6$) δ 12.03 (br s, 1H), 7.68 (s, 1H), 6.29 (br s, 2H), 3.65-3.72 (m, 2H), 3.57-3.63 (m, 1H), 2.86-2.91 (m, 1H), 2.62-2.70 (m, 2H), 2.46 (s, 3H), 1.55-1.66 (m, 2H), 1.15 (d, J = 6.0 Hz, 3H); 394.8 |
| 52 | Example 3 | 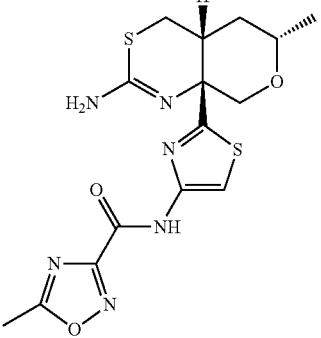 | 9.40 (br s, 1H), 7.75 (s, 1H), 4.70 (br s, 2H), 3.94 (d, J = 11.0 Hz, 1H), 3.81 (d, J = 11.0 Hz, 1H), 3.68-3.77 (m, 1H), 3.14 (dd, J = 12.4, 3.9 Hz, 1H), 2.74-2.82 (m, 1H), 2.71 (s, 3H), 2.59 (dd, J = 12.7, 2.6 Hz, 1H), 1.75-1.86 (m, 1H), 1.50-1.58 (m, 1H), 1.28 (d, J = 6.1 Hz, 3H); 394.9 |
| 53 | Example 3 | 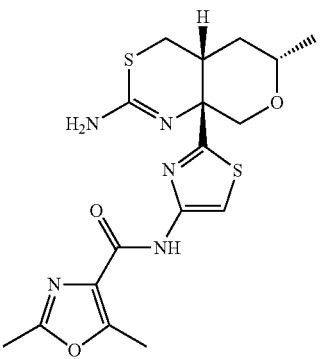 | 9.39 (s, 1H), 7.58 (s, 1H), 4.69 (br s, 2H), 3.93 (d, J = 10.7 Hz, 1H), 3.82 (d, J = 11.0 Hz, 1H), 3.68-3.77 (m, 1H), 3.15 (dd, J = 12.5, 4.0 Hz, 1H), 2.76-2.84 (m, 1H), 2.65 (s, 3H), 2.57 (dd, J = 12.5, 2.6 Hz, 1H), 2.44 (s, 3H), 1.74-1.85 (m, 1H), 1.49-1.56 (m, 1H), 1.28 (d, J = 6.1 Hz, 3H); 407.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 54 | P2$^{12}$ | 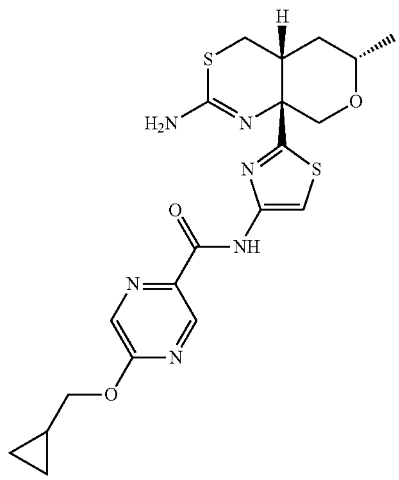 [SMILES: C[C@H]1C[C@H]2CSC(N)=N[C@@]2(c2nc(NC(=O)c3cnc(OCC4CC4)cn3)cs2)CO1] | 10.03 (s, 1H), 8.89 (d, J = 1.2 Hz, 1H), 8.10 (d, J = 1.2 Hz, 1H), 7.63 (s, 1H), 4.20 (d, J = 7.2 Hz, 2H), 3.91 (d, J = 10.9 Hz, 1H), 3.78 (d, J = 11.3 Hz, 1H), 3.62-3.72 (m, 1H), 3.10 (dd, J = 12.7, 4.1 Hz, 1H), 2.72-2.84 (m, 1H), 2.53 (dd, J = 12.9, 2.7 Hz, 1H), 1.66-1.81 (m, 1H), 1.44-1.52 (m, 1H), 1.22 (d, J = 6.2 Hz, 3H), 1.16-1.31 (m, 1H), 0.55-0.66 (m, 2H), 0.28-0.37 (m, 2H); 461.1 |
| 55 | P2$^{12}$ | 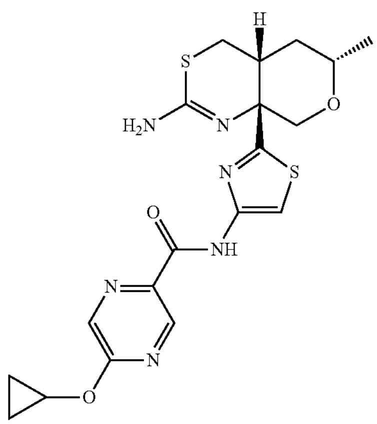 [SMILES: C[C@H]1C[C@H]2CSC(N)=N[C@@]2(c2nc(NC(=O)c3cnc(OC4CC4)cn3)cs2)CO1] | 10.03 (s, 1H), 8.99 (d, J = 1.2 Hz, 1H), 8.06 (d, J = 1.2 Hz, 1H), 7.64 (s, 1H), 4.34 (tt, J = 6.1, 3.1 Hz, 1H), 3.92 (d, J = 11.3 Hz, 1H), 3.78 (d, J = 11.3 Hz, 1H), 3.60-3.72 (m, 1H), 3.10 (dd, J = 12.5, 3.9 Hz, 1H), 2.74-2.82 (m, 1H), 2.53 (dd, J = 12.5, 2.7 Hz, 1H), 1.66-1.83 (m, 1H), 1.44-1.51 (m, 1H), 1.22 (d, J = 5.9 Hz, 3H), 0.74-0.88 (m, 4H); 447.3 |
| 56 | P2$^{12}$ | 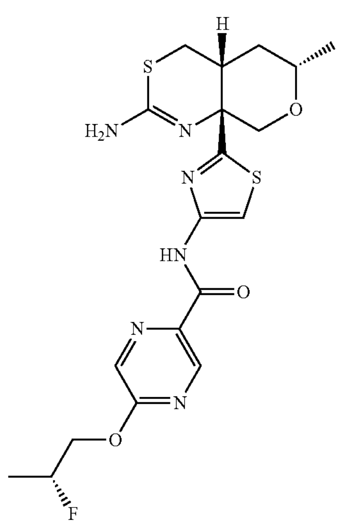 [SMILES: C[C@@H](F)COc1cnc(C(=O)Nc2csc([C@]34CO[C@@H](C)C[C@H]3CSC(N)=N4)n2)cn1] | 10.11 (s, 1H), 8.99 (d, J = 1.2 Hz, 1H), 8.25 (d, J = 1.6 Hz, 1H), 7.70 (s, 1H), [4.97-5.05 and 5.09-5.18 (m, J$_{HF}$ = 49.1 Hz, 1H)], 4.43-4.73 (m, 2H), 4.59 (br s, 2H), 3.95 (d, J = 10.9 Hz, 1H), 3.85 (d, J = 10.9 Hz, 1H), 3.69-3.80 (m, 1H), 3.17 (dd, J = 12.5, 3.9 Hz, 1H), 2.78-2.87 (m, 1H), 2.59 (dd, J = 12.7, 2.9 Hz, 1H), 1.75-1.86 (m, 1H), 1.44-1.57 (m, 4H), 1.29 (d, J = 6.2 Hz, 3H); 467.1 |

TABLE 1-continued

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 57 | P2[12] | 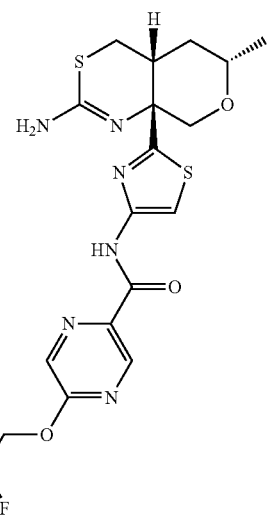 | 10.11 (s, 1H), 8.99 (d, J = 1.6 Hz, 1H), 8.25 (d, J = 1.2 Hz, 1H), 7.70 (s, 1H), [4.97-5.05 and 5.09-5.18 (m, J$_{HF}$ = 49.2 Hz, 1H)], 4.44-4.63 (m, 2H), 4.56 (br s, 2H), 3.95 (d, J = 10.9 Hz, 1H), 3.86 (d, J = 11.3 Hz, 1H), 3.70-3.78 (m, 1H), 3.17 (dd, J = 12.5, 3.9 Hz, 1H), 2.78-2.87 (m, 1H), 2.59 (dd, J = 12.5, 2.7 Hz, 1H), 1.75-1.86 (m, 1H), 1.44-1.57 (m, 4H), 1.29 (d, J = 6.2 Hz, 3H); 467.1 |
| 58 | P2[12] | 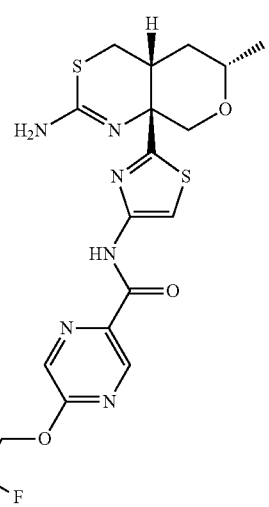 | 10.10 (s, 1H), 9.01 (d, J = 1.2 Hz, 1H), 8.28 (d, J = 1.2 Hz, 1H), 7.71 (s, 1H), 4.62 (t, J$_{HF}$ = 11.9 Hz, 2H), 4.56 (br s, 2H), 3.96 (d, J = 10.9 Hz, 1H), 3.86 (d, J = 10.9 Hz, 1H), 3.70-3.79 (m, 1H), 3.17 (dd, J = 12.5, 3.9 Hz, 1H), 2.82 (dq, J = 12.5, 3.6 Hz, 1H), 2.59 (dd, J = 12.5, 2.7 Hz, 1H), 1.73-1.87 (m, 4H), 1.54 (ddd, J = 13.5, 4.1, 2.3 Hz, 1H), 1.29 (d, J = 6.2 Hz, 3H); 485.1 |
| 87 | Example 3[10] | 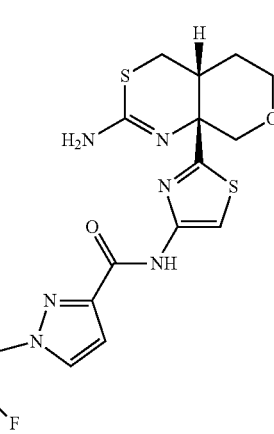 | 9.33 (br s, 1H), 7.64 (s, 1H), 7.54 (d, J = 2.3 Hz, 1H), 6.96 (d, J = 2.3 Hz, 1H), 6.15 (tt, J = 55.3, 4 Hz, 1H), 4.53 (td, J = 13.4, 4.1 Hz, 2H), 4.5-4.7 (v br s, 2H), 3.90 (AB quartet, J$_{AB}$ = 11.0 Hz, Δv$_{AB}$ = 40.2 Hz, 2H), 3.69-3.79 (m, 1H), 3.17 (dd, J = 12.6, 3.9 Hz, 1H), 2.77-2.85 (m, 1H), 2.59 (dd, J = 12.6, 2.6 Hz, 1H), 1.74-1.87 (m, 1H), 1.50-1.57 (m, 1H), 1.29 (d, J = 6.2 Hz, 3H); 442.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 88 | Example 3 | 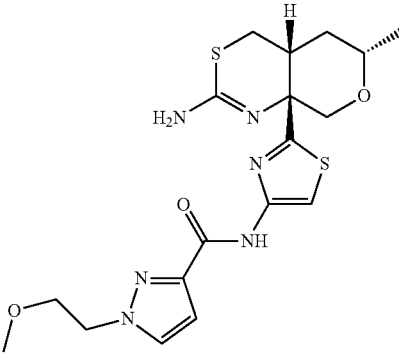 | 9.37 (br s, 1H), 7.63 (s, 1H), 7.52 (d, J = 2.3 Hz, 1H), 6.88 (d, J = 2.3 Hz, 1H), 4.45-4.75 (v br s, 2H), 4.33 (t, J = 5.0 Hz, 2H), 3.90 (AB quartet, J$_{AB}$ = 11.0 Hz, Δv$_{AB}$ = 38.1 Hz, 2H), 3.78 (t, J = 5.1 Hz, 2H), 3.69-3.78 (m, 1H), 3.35 (s, 3H), 3.17 (dd, J = 12.6, 3.9 Hz, 1H), 2.76-2.84 (m, 1H), 2.58 (dd, J = 12.6, 2.5 Hz, 1H), 1.74-1.86 (m, 1H), 1.49-1.57 (m, 1H), 1.29 (d, J = 6.0 Hz, 3H); 436.9 |
| 89 | Example 3[13] | 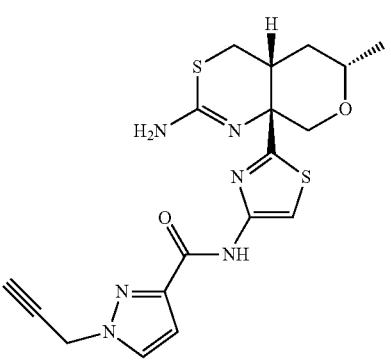 [SMILES: C#CCn1ccc(C(=O)Nc2csc([C@]34CO[C@@H](C)C[C@H]3CSC(N)=N4)n2)n1] | 9.37 (br s, 1H), 7.68 (d, J = 2.1 Hz, 1H), 7.63 (s, 1H), 6.94 (d, J = 2.3 Hz, 1H), 4.99 (d, J = 2.5 Hz, 2H), 4.50-4.74 (br s, 2H), 3.90 (AB quartet, J$_{AB}$ = 11.0 Hz, Δv$_{AB}$ = 40.6 Hz, 2H), 3.68-3.79 (m, 1H), 3.16 (dd, J = 12.6, 3.9 Hz, 1H), 2.76-2.85 (m, 1H), 2.54-2.62 (m, 2H), 1.74-1.86 (m, 1H), 1.49-1.57 (m, 1H), 1.29 (d, J = 6.0 Hz, 3H); 416.9 |
| 90 | Example 3 | 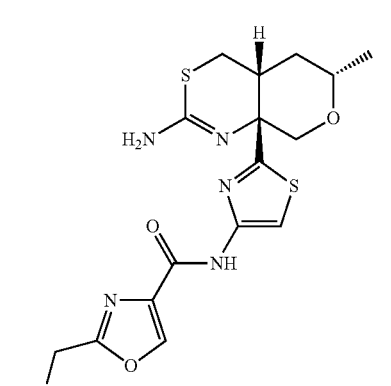 | 9.42 (br s, 1H), 8.30 (s, 1H), 7.64 (s, 1H), 4.59 (s, 2H), 3.89 (AB quartet, J$_{AB}$ = 11.0 Hz, Δv$_{AB}$ = 49.6 Hz, 2H), 3.67-3.79 (m, 1H), 3.51 (s, 3H), 3.11-3.21 (m, 1H), 2.75-2.85 (m, 1H), 2.59 (br d, J = 12 Hz, 1H), 1.73-1.87 (m, 1H), 1.49-1.59 (m, 1H), 1.29 (d, J = 5.9 Hz, 3H); 423.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 91 | Example 3 | 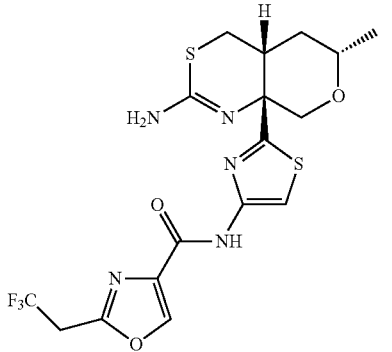 [SMILES: C[C@H]1C[C@H]2CSC(N)=N[C@@]2(c2nc(NC(=O)c3coc(CC(F)(F)F)n3)cs2)CO1] | 9.34 (br s, 1H), 8.33 (s, 1H), 7.65 (s, 1H), 3.90 (AB quartet, J$_{AB}$ = 11.1 Hz, Δv$_{AB}$ = 47.6 Hz, 2H), 3.64-3.80 (m, 3H), 3.11-3.20 (m, 1H), 2.77-2.88 (m, 1H), 2.55-2.64 (m, 1H), 1.73-1.87 (m, 1H, assumed; partially obscured by water peak), 1.50-1.59 (m, 1H), 1.29 (d, J = 5.9 Hz, 3H); 461.9 |
| 92 | Example 89 | 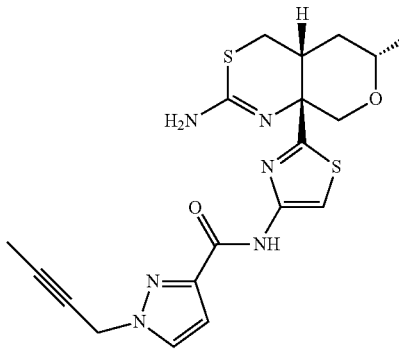 | $^1$H NMR (400 MHz, DMSO-d$_6$) δ 10.22 (br s, 1H), 7.95 (d, J = 2.4 Hz, 1H), 7.56 (s, 1H), 6.93 (d, J = 2.4 Hz, 1H), 6.27 (br s, 2H), 5.07-5.12 (m, 2H), 3.66-3.73 (m, 2H), 3.58-3.67 (m, 1H), 2.86-2.95 (m, 1H), 2.62-2.74 (m, 2H), 1.86 (t, J = 2.4 Hz, 3H), 1.51-1.66 (m, 2H), 1.16 (d, J = 6.0 Hz, 3H); 430.9 |
| 93 | Method B; P2 | 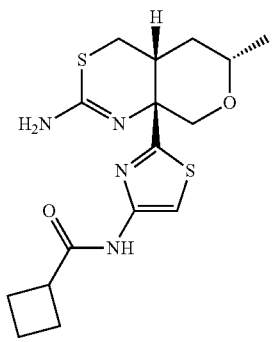 [SMILES: C[C@H]1C[C@H]2CSC(N)=N[C@@]2(c2nc(NC(=O)C3CCC3)cs2)CO1] | 1.57 minutes$^3$; 367.1 |

TABLE 1-continued

Method of Preparation, Structure, and Physicochemical Data for Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 94 | Example 3[10] | 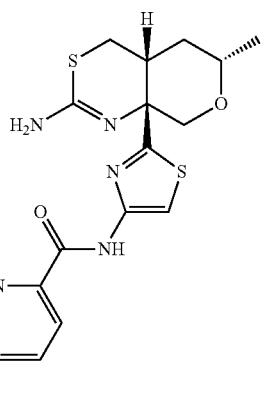 | 10.40 (br s, 1H), 8.33 (br s, 1H), 8.23 (d, J = 8.5 Hz, 1H), 7.68 (s, 1H), 7.44 (br d, J = 8 Hz, 1H), 4.78 (s, 2H), 4.53-4.8 (br s, 2H), 3.90 (AB quartet, J$_{AB}$ = 11.0 Hz, Δν$_{AB}$ = 33.6 Hz, 2H), 3.68-3.80 (m, 1H), 3.12-3.22 (m, 1H), 2.77-2.88 (m, 1H), 2.58 (br d, J = 12.4 Hz, 1H), 1.88 (br s, 3H), 1.73-1.87 (m, 1H), 1.48-1.58 (m, 1H), 1.28 (d, J = 5.8 Hz, 3H); 457.9 |
| 95 | Example 2[14] | 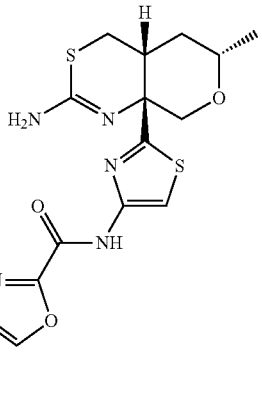 | $^1$H NMR (300 MHz, CDCl$_3$), δ 9.50 (br s, 1H), 8.10 (td, J = 2.2, 0.6 Hz, 1H), 7.69 (s, 1H), 6.72 (td, J = 54.5, 0.7 Hz, 1H), 4.56 (br s, 2H), 3.88 (AB quartet, J$_{AB}$ = 11.0 Hz, Δν$_{AB}$ = 37.8 Hz, 2H), 3.67-3.79 (m, 1H), 3.14 (dd, J = 12.5, 3.9 Hz, 1H), 2.74-2.84 (m, 1H), 2.60 (dd, J = 12.5, 2.7 Hz, 1H), 1.73-1.88 (m, 1H), 1.55 (ddd, J = 13, 4, 2 Hz, 1H), 1.30 (d, J = 6.1 Hz, 3H); 430.3 |
| 96 | Example 3[15] | 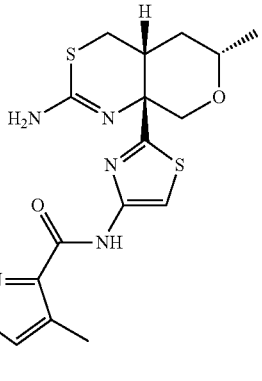 | 9.37 (br s, 1H), 7.67 (br s, 1H), 7.62 (s, 1H), 7.14 (t, J$_{HF}$ = 60.4 Hz, 1H), 4.4-4.9 (v br s, 2H), 3.90 (AB quartet, J$_{AB}$ = 11.2 Hz, Δν$_{AB}$ = 41.7 Hz, 2H), 3.69-3.78 (m, 1H), 3.16 (dd, J = 12.6, 4.0 Hz, 1H), 2.76-2.84 (m, 1H), 2.59 (dd, J = 12.6, 2.8 Hz, 1H), 2.43 (s, 3H), 1.74-1.86 (m, 1H), 1.54 (ddd, J = 13, 4, 2 Hz, 1H), 1.29 (d, J = 6.2 Hz, 3H); 442.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 97 | Example 2[16] | 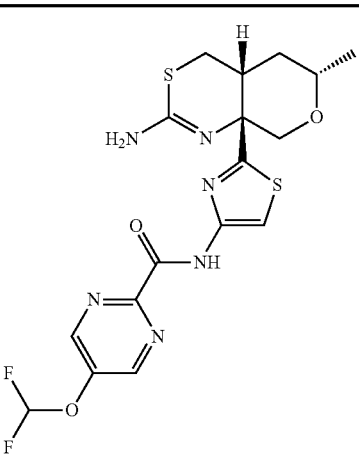 | $^1$H NMR (500 MHz, CDCl$_3$), δ 10.35 (br s, 1H), 8.79-8.81 (m, 2H), 7.86 (s, 1H), 6.72 (t, J$_{HF}$ = 70.9 Hz, 1H), 4.01 (br d, J = 11.3 Hz, 1H), 3.87 (d, J = 11.3 Hz, 1H), 3.71-3.79 (m, 1H), 3.19 (dd, J = 12.6, 4.0 Hz, 1H), 2.83-2.90 (m, 1H), 2.62 (dd, J = 12.6, 2.8 Hz, 1H), 1.81 (ddd, J = 13, 13, 11 Hz, 1H), 1.54-1.60 (m, 1H, assumed; partially obscured by water peak), 1.30 (d, J = 6.2 Hz, 3H); 457.1 |
| 98 | Example 3[17] | 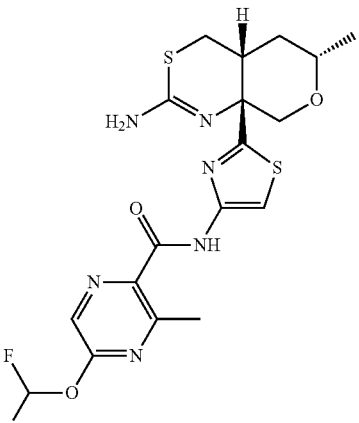 | 10.32 (br s, 1H), 8.18-8.20 (m, 1H), 7.69 (s, 1H), 7.54 (t, J$_{HF}$ = 71.6 Hz, 1H), 4.45-4.85 (v br s, 2H), 3.90 (AB quartet, J$_{AB}$ = 11.1 Hz, Δv$_{AB}$ = 36.0 Hz, 2H), 3.69-3.79 (m, 1H), 3.16 (dd, J = 12.6, 3.9 Hz, 1H), 2.99 (s, 3H), 2.78-2.86 (m, 1H), 2.59 (dd, J = 12.6, 2.7 Hz, 1H), 1.74-1.86 (m, 1H), 1.54 (ddd, J = 13, 4, 2 Hz, 1H), 1.29 (d, J = 6.2 Hz, 3H); 471.0 |
| 99 | Example 3 | 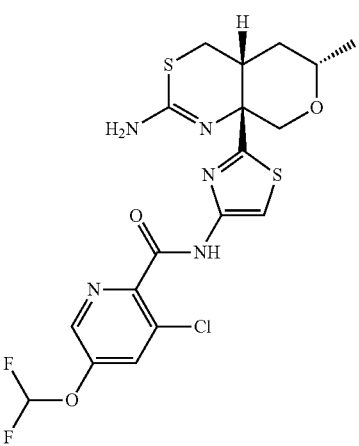 [SMILES: C[C@H]1C[C@H]2CSC(N)=N[C@@]2(c2nc(NC(=O)c3ncc(OC(F)F)cc3Cl)cs2)CO1] | 10.35 (br s, 1H), 8.42 (br d, J = 2.3 Hz, 1H), 7.74 (s, 1H), 7.69 (br d, J = 2.3 Hz, 1H), 6.67 (t, J$_{HF}$ = 71.3 Hz, 1H), 4.47-4.81 (v br s, 2H), 3.91 (AB quartet, J$_{AB}$ = 11.1 Hz, Δv$_{AB}$ = 38.3 Hz, 2H), 3.69-3.79 (m, 1H), 3.16 (dd, J = 12.5, 4.0 Hz, 1H), 2.78-2.86 (m, 1H), 2.59 (dd, J = 12.6, 2.7 Hz, 1H), 1.75-1.86 (m, 1H), 1.54 (ddd, J = 13, 4, 2 Hz, 1H), 1.29 (d, J = 6.2 Hz, 3H); 489.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 100 | Example 3[18,19,20] | 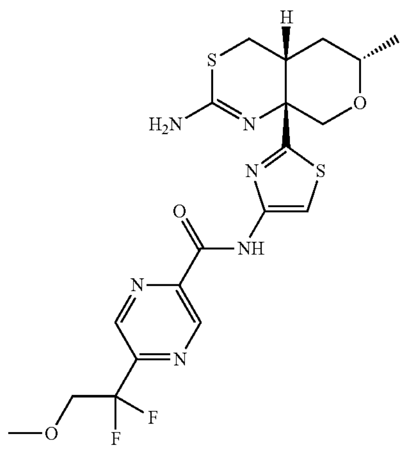 | 10.26 (br s, 1H), 9.53 (s, 1H), 8.94 (s, 1H), 7.80 (s, 1H), 4.12 (t, J$_{HF}$ = 12.4 Hz, 2H), 3.96 (AB quartet, downfield doublet is broadened, J$_{AB}$ = 11.4 Hz, Δv$_{AB}$ = 69.2 Hz, 2H), 3.71-3.81 (m, 1H), 3.43 (s, 3H), 3.20 (dd, J = 12.7, 3.9 Hz, 1H), 2.87-2.97 (m, 1H), 2.65 (dd, J = 12.8, 2.2 Hz, 1H), 1.75-1.87 (m, 1H), 1.56-1.63 (m, 1H), 1.31 (d, J = 6.2 Hz, 3H); 485.2 |
| 101 | Footnote 21 | 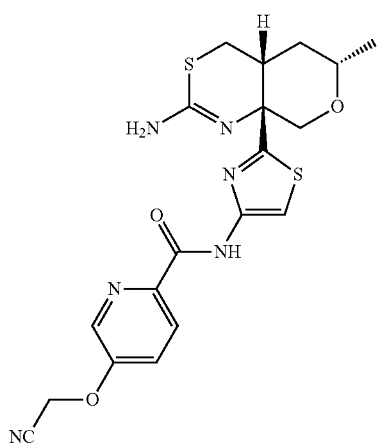 [SMILES: C[C@H]1C[C@H]2CSC(N)=N[C@@]2(c2nc(NC(=O)c3ccc(OCC#N)cn3)cs2)CO1] | 10.38 (br s, 1H), 8.39 (d, J = 2.8 Hz, 1H), 8.31 (d, J = 8.7 Hz, 1H), 7.74 (s, 1H), 7.49 (dd, J = 8.7, 2.9 Hz, 1H), 4.93 (s, 2H), 4.08 (br d, J = 11.5 Hz, 1H), 3.88 (d, J = 11.6 Hz, 1H), 3.71-3.82 (m, 1H), 3.21 (dd, J = 12.7, 3.8 Hz, 1H), 2.91-2.99 (m, 1H), 2.65 (dd, J = 12.7, 2.4 Hz, 1H), 1.74-1.86 (m, 1H), 1.56-1.64 (m, 1H), 1.31 (d, J = 6.2 Hz, 3H); 445.1 |
| 102 | Example 3[22] | 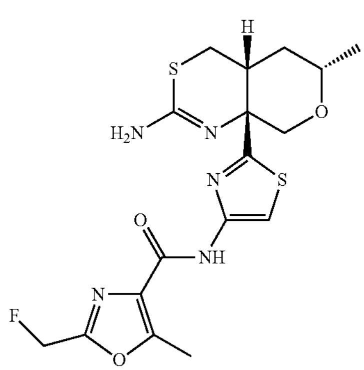 [SMILES: Cc1oc(CF)nc1C(=O)Nc1csc([C@]23CO[C@@H](C)C[C@H]2CSC(N)=N3)n1] | 9.40 (br s, 1H), 7.60 (s, 1H), 5.36 (d, J$_{HF}$ = 47.4 Hz, 2H), 4.35-4.90 (v br s, 2H), 3.88 (AB quartet, J$_{AB}$ = 10.9 Hz, Δv$_{AB}$ = 42 Hz, 2H), 3.68-3.78 (m, 1H), 3.15 (dd, J = 12, 3 Hz, 1H), 2.76-2.84 (m, 1H), 2.74 (s, 3H), 2.54-2.62 (m, 1H), 1.73-1.86 (m, 1H), 1.50-1.57 (m, 1H), 1.29 (d, J = 5.9 Hz, 3H); 425.9 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 103 | Example 3[23,24] | 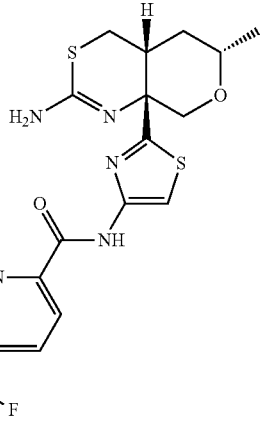 | 10.53 (br s, 1H), 8.76-8.80 (m, 1H), 8.35 (d, J = 8.2 Hz, 1H), 8.06 (dd, J = 8.1, 2.2 Hz, 1H), 7.74 (s, 1H), 4.5-4.7 (br s, 2H), 3.92 (AB quartet, J$_{AB}$ = 11.1 Hz, Δν$_{AB}$ = 35.4 Hz, 2H), 3.88 (t, J$_{HF}$ = 12.2 Hz, 2H), 3.71-3.81 (m, 1H), 3.45 (s, 3H), 3.18 (dd, J = 12.6, 4.0 Hz, 1H), 2.81-2.89 (m, 1H), 2.60 (dd, J = 12.6, 2.8 Hz, 1H), 1.75-1.88 (m, 1H), 1.55 (ddd, J = 13, 4, 2 Hz, 1H), 1.30 (d, J = 6.1 Hz, 3H); 484.1 |
| 104 | Example 3[10,18,25] | 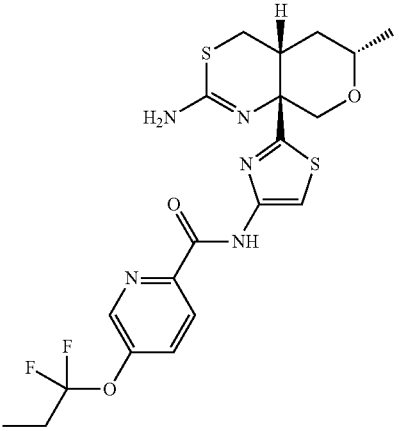 [SMILES: CCC(F)(F)Oc1ccc(C(=O)Nc2csc([C@]34CO[C@@H](C)C[C@H]3CSC(N)=N4)n2)nc1] | 10.42 (s, 1H), 8.47 (s, 1H), 8.28 (d, J = 8.5 Hz, 1H), 7.69-7.78 (m, 2H), 4.3-5.7 (v br s, 2H), 3.94 (AB quartet, J$_{AB}$ = 11.3 Hz, Δν$_{AB}$ = 49.2 Hz, 2H), 3.69-3.81 (m, 1H), 3.19 (dd, J = 12, 3 Hz, 1H), 2.82-2.93 (m, 1H), 2.61 (d, J = 12.5 Hz, 1H), 2.17-2.33 (m, 2H), 1.73-1.88 (m, 1H), 1.51-1.61 (m, 1H), 1.30 (d, J = 6.0 Hz, 3H), 1.22 (t, J = 7.5 Hz, 3H); 484.1 |
| 105 | Example 104 | 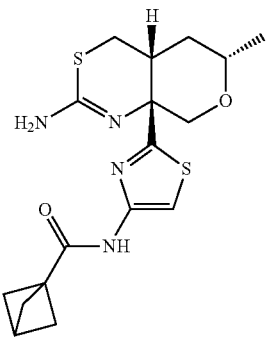 [SMILES: C[C@H]1C[C@H]2CSC(N)=N[C@@]2(c2nc(NC(=O)C34CC(C3)C4)cs2)CO1] | $^1$H NMR (400 MHz, CD$_3$OD) δ 7.47 (s, 1H), 3.84 (AB quartet, J$_{AB}$ = 11.1 Hz, Δν$_{AB}$ = 23.3 Hz, 2H), 3.66-3.76 (m, 1H), 3.03 (dd, J = 12.7, 4.0 Hz, 1H), 2.77-2.85 (m, 1H), 2.65 (dd, J = 12.7, 2.7 Hz, 1H), 2.47 (s, 1H), 2.15 (s, 6H), 1.66-1.77 (m, 1H), 1.58 (ddd, J = 13, 4, 2.5 Hz, 1H), 1.23 (d, J = 6.1 Hz, 3H); 379.1 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|
| 106 | Example 3[10] | 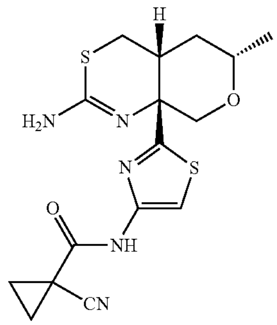 [SMILES: C[C@H]1C[C@H]2CSC(N)=N[C@@]2(c2nc(NC(=O)C3(C#N)CC3)cs2)CO1] | 8.86 (br s, 1H), 7.45 (s, 1H), 4.4-4.8 (v br s, 2H), 3.86 (AB quartet, J$_{AB}$ = 11.1 Hz, Δv$_{AB}$ = 42.6 Hz, 2H), 3.70-3.79 (m, 1H), 3.13 (dd, J = 12.5, 4.0 Hz, 1H), 2.76-2.84 (m, 1H), 2.60 (dd, J = 12.6, 2.7 Hz, 1H), 1.74-1.85 (m 3H), 1.6-1.7 (m, 2H, assumed; partially obscured by water peak), 1.55 (ddd, J = 13, 4, 2 Hz, 1H), 1.29 (d, J = 6.2 Hz, 3H); 378.0 |
| 107 | Method B; P2 | 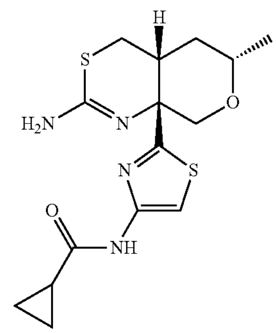 [SMILES: C[C@H]1C[C@H]2CSC(N)=N[C@@]2(c2nc(NC(=O)C3CC3)cs2)CO1] | 1.30 minutes[3]; 353.1 |
| 108 | Example 100 | 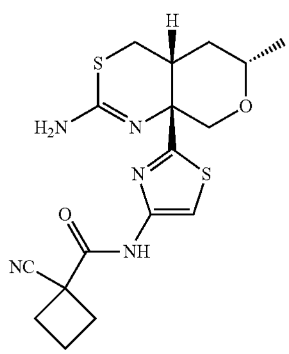 [SMILES: C[C@H]1C[C@H]2CSC(N)=N[C@@]2(c2nc(NC(=O)C3(C#N)CCC3)cs2)CO1] | 8.52 (br s, 1H), 7.55 (s, 1H), 4.37-4.75 (v br s, 2H), 3.85 (AB quartet, J$_{AB}$ = 11.1 Hz, Δv$_{AB}$ = 46.8 Hz, 2H), 3.68-3.78 (m, 1H), 3.12 (dd, J = 12.5, 3.9 Hz, 1H), 2.82-2.97 (m, 2H), 2.73-2.82 (m, 1H), 2.55-2.69 (m, 3H), 2.28-2.41 (m, 1H), 2.16-2.28 (m, 1H), 1.73-1.85 (m, 1H), 1.50-1.58 (m, 1H), 1.29 (d, J = 6.2 Hz, 3H); 392.4 |
| 109 | Example 3[18] | 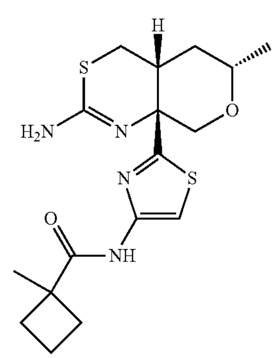 | 7.94 (br s, 1H), 7.55 (s, 1H), 4.35-4.85 (v br s, 2H), 3.87 (AB quartet, J$_{AB}$ = 11.1 Hz, Δv$_{AB}$ = 46.0 Hz, 2H), 3.67-3.77 (m, 1H), 3.14 (dd, J = 12.5, 4.0 Hz, 1H), 2.69-2.78 (m, 1H), 2.48-2.61 (m, 3H), 1.98-2.10 (m, 1H), 1.74-1.96 (m, 4H), 1.54 (s, 3H), 1.49-1.56 (m, 1H), 1.28 (d, J = 6.2 Hz, 3H); 381.0 |

TABLE 1-continued

Method of Preparation, Structure, and Physicochemical Data for
Examples 9-58 and 87-109

| Example Number | Method of Preparation; Non-commercial starting materials | Structure | $^1$H NMR (400 MHz, CDCl$_3$) δ (ppm); Mass spectrum, observed ion m/z (M + H$^+$) or HPLC retention time; Mass spectrum m/z [M + H]$^+$ (unless otherwise indicated) |
|---|---|---|---|

[1] In this case, the amide coupling was carried out by reacting P2 with the acid chloride, which was generated via reaction of the corresponding carboxylic acid with oxalyl chloride and N,N-dimethylformamide.

[2] Reaction of methyl 5-hydroxypyridine-2-carboxylate with bromo(fluoro)methane and cesium carbonate in N,N-dimethylformamide provided methyl 5-(fluoromethoxy)pyridine-2-carboxylate; ester hydrolysis with lithium hydroxide afforded the requisite 5-(fluoromethoxy)pyridine-2-carboxylic acid.

[3] Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

[4] The requisite 5-(trifluoromethyl)-1,2-oxazole-3-carboxylic acid may be prepared using the method of D. W. Piotrowski et al., *PCT International Application*, WO 2003093250 A2, Nov. 13, 2003.

[5] Reaction of 1-cyclobutylethanone with diethyl oxalate and sodium ethoxide provided ethyl 4-cyclobutyl-2,4-dioxobutanoate, which was condensed with hydrazine hydrate to afford ethyl 3-cyclobutyl-1H-pyrazole-5-carboxylate. Subjection to dimethyl sulfate gave ethyl 3-cyclobutyl-1-methyl-1H-pyrazole-5-carboxylate, which was hydrolyzed with sodium hydroxide in ethanol to afford the requisite 3-cyclobutyl-1-methyl-1H-pyrazole-5-carboxylic acid.

[6] Reaction of methyl 5-hydroxypyridine-2-carboxylate with 2-bromo-1,1-difluoroethane and potassium carbonate provided methyl 5-(2,2-difluoroethoxy)pyridine-2-carboxylate; lithium hydroxide-mediated ester hydrolysis afforded the requisite 5-(2,2-difluoroethoxy)pyridine-2-carboxylic acid.

[7] Treatment of 1-(chloromethyl)-4-methoxybenzene with sodium azide was followed by reaction with ethyl prop-2-ynoate and copper(II) sulfate to afford ethyl 2-(4-methoxybenzyl)-2H-1,2,3-triazole-4-carboxylate; this material was deprotected with trifluoroacetic acid and methylated with iodomethane in the presence of potassium carbonate to provide ethyl 2-methyl-2H-1,2,3-triazole-4-carboxylate. Ester hydrolysis with sodium hydroxide yielded the requisite 2-methyl-2H-1,2,3-triazole-4-carboxylic acid.

[8] In this case, the final deprotection was carried out using hydrazine in ethanol, rather than 1,8-diazabicyclo[5.4.0]undec-7-ene.

[9] Potassium hydroxide-mediated reaction of 5-hydroxypyridine-2-carbonitrile and 2-bromo-1,1-difluoroethene provided 5-(2-bromo-1,1-difluoroethoxy)pyridine-2-carbonitrile, which was converted to the methyl ester by exposure to hydrogen chloride in methanol and subsequently hydrogenated to afford methyl 5-(1,1-difluoroethoxy)pyridine-2-carboxylate. Ester hydrolysis with lithium hydroxide gave the requisite 5-(1,1-difluoroethoxy)pyridine-2-carboxylic acid.

[10] In this case, the final deprotection was carried out using hydrazine in ethanol, rather than methoxylamine hydrochloride.

[11] In this case, the final deprotection was carried out using 1,8-diazabicyclo[5.4.0]undec-7-ene, rather than methoxylamine hydrochloride.

[12] Compound P2 was reacted with 5-chloropyrazine-2-carboxylic acid using 2,4,6-tripropyl-1,3,5,2,4,6-trioxatriphosphinane 2,4,6-trioxide and triethylamine, to generate N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-chloropyrazine-2-carboxamide. This was subjected to reaction with the requisite alcohol and cesium carbonate in N,N-dimethylformamide, followed by deprotection with benzyloxylamine hydrochloride and pyridine in ethanol at elevated temperature, to afford the compound of the Example.

[13] After P2 was coupled with 1H-pyrazole-3-carboxylic acid, the resulting N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-1H-pyrazole-3-carboxamide was reacted with 3-bromoprop-1-yne and potassium carbonate in N,N-dimethylformamide to afford N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-1-(prop-2-yn-1-yl)-1H-pyrazole-3-carboxamide. Deprotection provided Example 89.

[14] Conversion of ester C26 to the corresponding aldehyde was carried out via reduction with diisobutylaluminum hydride followed by oxidation using the Dess-Martin reagent. Subsequent reaction with (diethylamino)sulfur trifluoride afforded 4-(difluoromethyl)-2-[(E)-2-phenylethenyl]-1,3-oxazole, which was subjected to osmium tetroxide and 4-methylmorpholine N-oxide, followed by sodium periodate, to provide 4-(difluoromethyl)-1,3-oxazole-2-carbaldehyde. Oxidation with sodium chlorite/2-methylbut-2-ene generated the requisite 4-(difluoromethyl)-1,3-oxazole-2-carboxylic acid.

[15] Ethyl 4-methyl-1H-pyrazole-3-carboxylate was reacted with sodium hydride and chloro(difluoro)methane to provide ethyl 1-(difluoromethyl)-4-methyl-1H-pyrazole-3-carboxylate. Ester hydrolysis with lithium hydroxide in aqueous tetrahydrofuran afforded the requisite 1-(difluoromethyl)-4-methyl-1H-pyrazole-3-carboxylic acid.

[16] Reaction of 2-chloro-5-(difluoromethoxy)pyrimidine with zinc cyanide, tris(dibenzylideneacetone)dipalladium(0), 1,1'-bis(diphenylphosphino)ferrocene, and zinc dust in N,N-dimethylacetamide at elevated temperature provided 5-(difluoromethoxy)pyrimidine-2-carbonitrile. This material was hydrolyzed with aqueous sodium hydroxide solution to afford the requisite 5-(difluoromethoxy)pyrimidine-2-carboxylic acid.

[17] Treatment of methyl 5-methoxy-3-methylpyrazine-2-carboxylate with trimethylsilyl chloride and potassium iodide provided methyl 3-methyl-5-oxo-4,5-dihydropyrazine-2-carboxylate, which was subjected to reaction with sodium chloro(difluoro)acetate and cesium carbonate to afford methyl 5-(difluoromethoxy)-3-methylpyrazine-2-carboxylate. Ester hydrolysis with lithium hydroxide in aqueous tetrahydrofuran afforded the requisite 5-(difluoromethoxy)-3-methylpyrazine-2-carboxylic acid.

[18] The amide coupling step employed triethylamine in this case, rather than pyridine.

[19] In this case, the final deprotection was carried out using methylamine, rather than methoxylamine hydrochloride.

[20] Reaction of 2-bromo-5-chloropyrazine with copper powder and ethyl bromo(difluoro)acetate in dimethyl sulfoxide provided ethyl (5-chloropyrazin-2-yl)(difluoro)acetate. Reduction to the alcohol with sodium borohydride in ethanol was followed by methyl ether formation with iodomethane and silver(I) oxide. The resulting 2-chloro-5-(1,1-difluoro-2-methoxyethyl)pyrazine was reacted with carbon monoxide, 1-propanol, [(R)-(+)-1,1'-binaphthalene-2,2'-diylbis(diphenylphosphane)]palladium (II) chloride, and triethylamine, followed by ester hydrolysis with sodium hydroxide in aqueous tetrahydrofuran, to provide the requisite 5-(1,1-difluoro-2-methoxyethyl)pyrazine-2-carboxylic acid.

21. Amide coupling of P2 with 5-hydroxypyridine-2-carboxylic acid was effected with 1-[3-(dimethylamino)propyl]-3-ethylcarbodiimide hydrochloride, 1H-benzotriazol-1-ol, and triethylamine. The resulting N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-hydroxypyridine-2-carboxamide was reacted with bromoacetonitrile and potassium carbonate to provide N-{2-[(4aR,6S,8aR)-2-(benzoylamino)-6-methyl-4,4a,5,6-tetrahydropyrano[3,4-d][1,3]thiazin-8a(8H)-yl]-1,3-thiazol-4-yl}-5-(cyanomethoxy)pyridine-2-carboxamide; deprotection with hydrazine then afforded Example 101.

[22] In this case, the hydrochloride salt of methyl 2-amino-3-hydroxybutanoate was used as starting material, providing methyl 2-(dichloromethyl)-5-methyl-4,5-dihydro-1,3-oxazole-4-carboxylate. Treatment with sodium methoxide provided methyl 2-(chloromethyl)-5-methyl-1,3-oxazole-4-carboxylate, which was carried on using the general methods of Example 3 to provide the requisite 2-(fluoromethyl)-5-methyl-1,3-oxazole-4-carboxylic acid.

[23] In this case, the final deprotection was carried out using O-benzylhydroxylamine hydrochloride, rather than methoxylamine hydrochloride.

[24] Subjection of ethyl bromo(difluoro)acetate and tert-butyl 5-bromopyridine-2-carboxylate to copper powder in dimethyl sulfoxide provided tert-butyl 5-(2-ethoxy-1,1-difluoro-2-oxoethyl)pyridine-2-carboxylate. Reduction of the ethyl ester to the primary alcohol was carried out with sodium borohydride in ethanol; subsequent methyl ether formation with iodomethane and silver(I) oxide afforded tert-butyl 5-(1,1-difluoro-2-methoxyethyl)pyridine-2-carboxylate. Treatment with trifluoroacetic acid then generated the requisite 5-(1,1-difluoro-2-methoxyethyl)pyridine-2-carboxylic acid.

[25] Silver(I) oxide-mediated reaction of methyl 5-hydroxypyridine-2-carboxylate with 3-bromo-3,3-difluoroprop-1-ene provided methyl 5-[(1,1-difluoroprop-2-en-1-yl)oxy]pyridine-2-carboxylate. Olefin reduction with palladium on carbon and triethylsilane, followed by ester hydrolysis using lithium hydroxide in aqueous tetrahydrofuran, afforded the requisite 5-(1,1-difluoropropoxy)pyridine-2-carboxylic acid.

TABLE 2
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 59 | Method A; P2 | 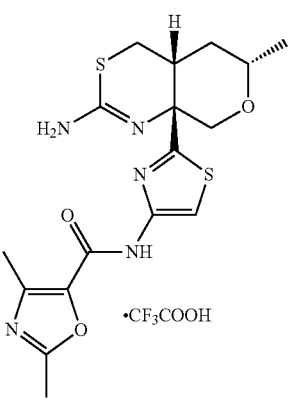 | 408.2 |
| 60 | Method A; P2 | 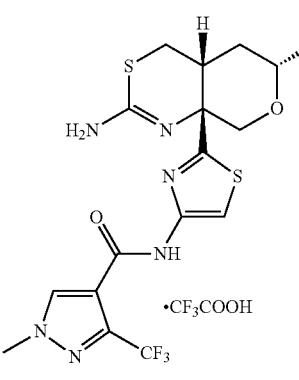 | 461.1 |
| 61 | Method A; P2 | 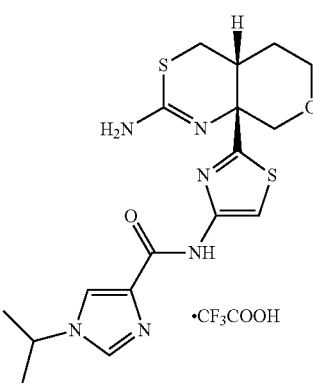 | 421.2 |

TABLE 2-continued

Method of Preparation, Structure, and Physicochemical Data for Examples 59-86

| Example Number | Method of Preparation; Non-commercial starting materials | Structure | Mass spectrum m/z [M + H]⁺ (unless otherwise indicated) |
|---|---|---|---|
| 62 | Method A; P2 | (structure) ·CF₃COOH | 436.2 |
| 63 | Method A; P2 | (structure) ·CF₃COOH | 393.2 |
| 64 | Method A; P2 | (structure) ·CF₃COOH | 394.2 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 65 | Method A; P2 | 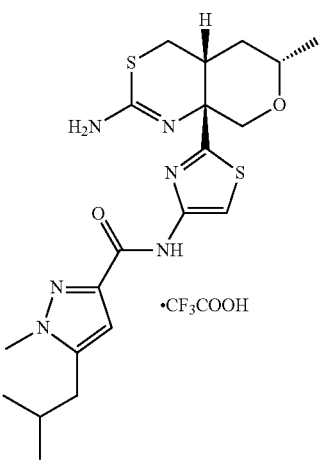 [SMILES: CC(C)Cc1cc(C(=O)Nc2csc([C@]34CO[C@@H](C)C[C@H]3CSC(N)=N4)n2)nn1C ; "·CF3COOH"] | 449.2 |
| 66 | Method A; P2 | 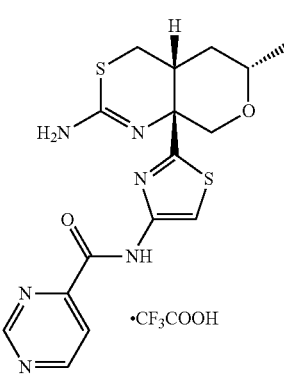 | 391.2 |
| 67 | Method A; P2 | 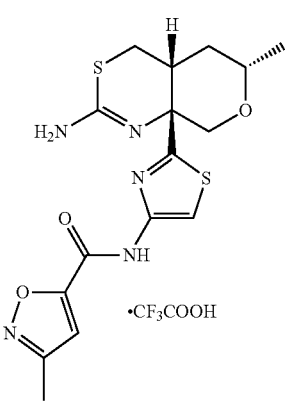 [SMILES: Cc1cc(C(=O)Nc2csc([C@]34CO[C@@H](C)C[C@H]3CSC(N)=N4)n2)on1 ; "·CF3COOH"] | 394.2 |

TABLE 2-continued

Method of Preparation, Structure, and Physicochemical Data for Examples 59-86

| Example Number | Method of Preparation; Non-commercial starting materials | Structure | Mass spectrum m/z [M + H]+ (unless otherwise indicated) |
|---|---|---|---|
| 68 | Method A; P2 | (structure) ·CF$_3$COOH | 405.2 |
| 69 | Method A; P2 | (structure) ·CF$_3$COOH | 419.2 |
| 70 | Method A; P2 | (structure) ·CF$_3$COOH | 435.2 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 71 | Method A; P2 | 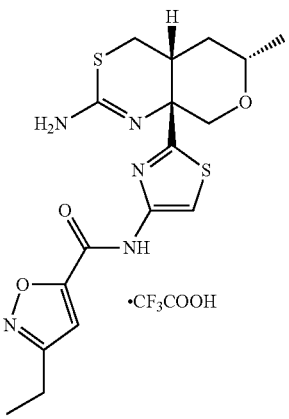 [SMILES: CCc1cc(C(=O)Nc2csc([C@]34CO[C@@H](C)C[C@H]3CSC(N)=N4)n2)on1 ; "·CF3COOH"] | 408.2 |
| 72 | Method A; P2 | 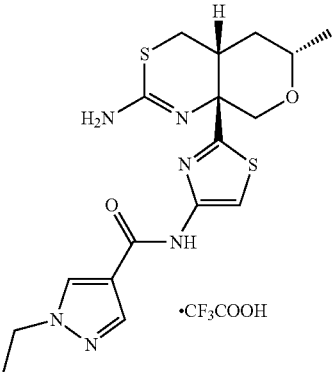 [SMILES: CCn1cc(C(=O)Nc2csc([C@]34CO[C@@H](C)C[C@H]3CSC(N)=N4)n2)cn1 ; "·CF3COOH"] | 407.2 |
| 73 | Method A; P2 | 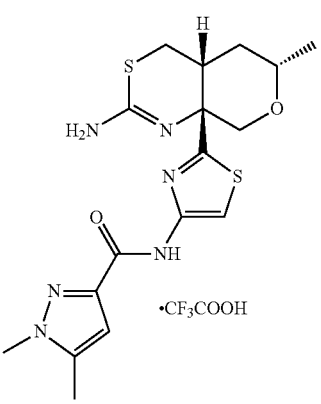 | 407.2 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 74 | Method A; P2 | 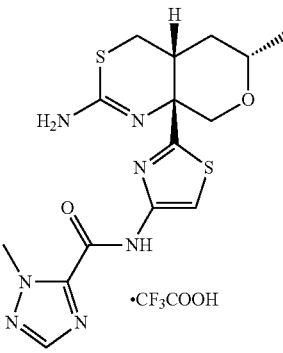 | 394.2 |
| 75 | Method A; P2 | 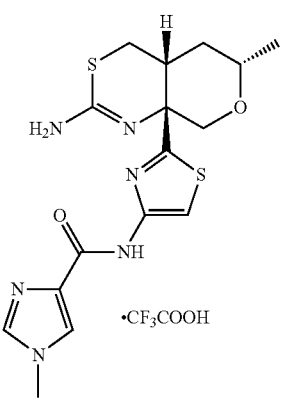 [SMILES: C[C@H]1C[C@H]2CSC(N)=N[C@@]2(c2nc(NC(=O)c3cn(C)cn3)cs2)CO1 ; "·CF3COOH"] | 393.2 |
| 76 | Method A; P2 | 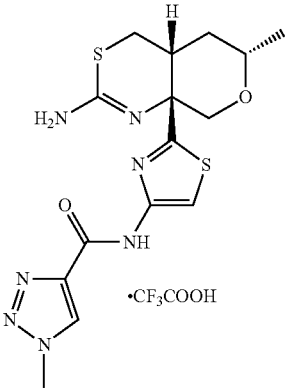 [SMILES: C[C@H]1C[C@H]2CSC(N)=N[C@@]2(c2nc(NC(=O)c3cn(C)nn3)cs2)CO1 ; "·CF3COOH"] | 394.2 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 77 | Method A; P2 | 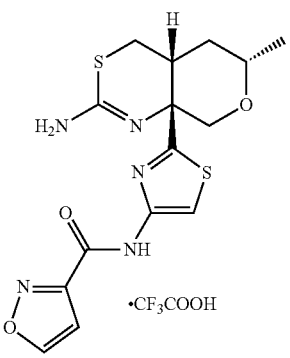 [SMILES: C[C@H]1C[C@H]2CSC(N)=N[C@@]2(c2nc(NC(=O)c3ccon3)cs2)CO1 ; "·CF3COOH"] | 380.2 |
| 78 | Method A; P2 | 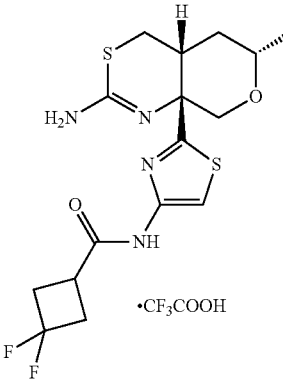 | 403.2 |
| 79 | Method A; P2 | 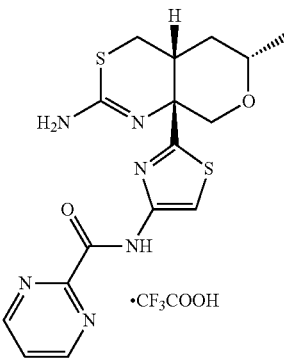 | 391.1 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 80 | Example 3[1,2] | 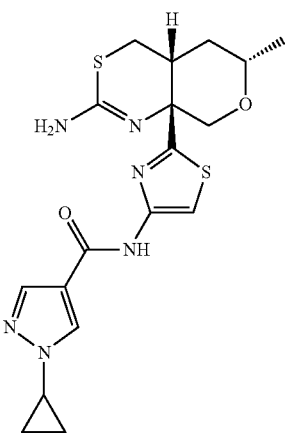 [SMILES: C[C@H]1C[C@H]2CSC(N)=N[C@@]2(c2nc(NC(=O)c3cnn(C4CC4)c3)cs2)CO1] | 418.9 |
| 81 | Example 4 | 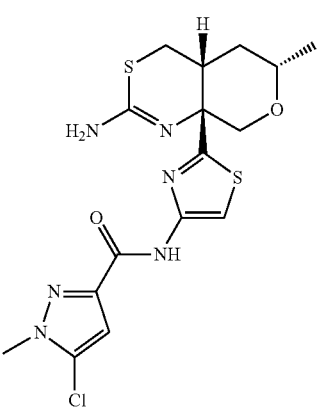 | 426.8 |
| 82 | Example 4 | 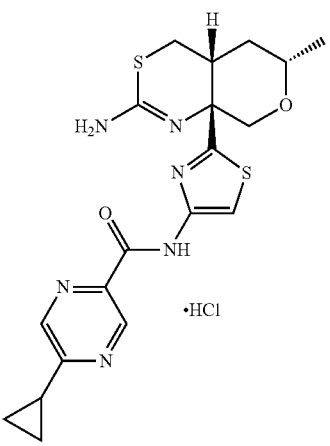 [SMILES: C[C@H]1C[C@H]2CSC(N)=N[C@@]2(c2nc(NC(=O)c3cnc(C4CC4)cn3)cs2)CO1 ; Cl] | 430.9 |

TABLE 2-continued
Method of Preparation, Structure, and Physicochemical Data for Examples 59-86
| Example Number | Method of Preparation; Non-commercial starting materials | Structure | Mass spectrum m/z [M + H]+ (unless otherwise indicated) |
|---|---|---|---|
| 83 | Example 4 | 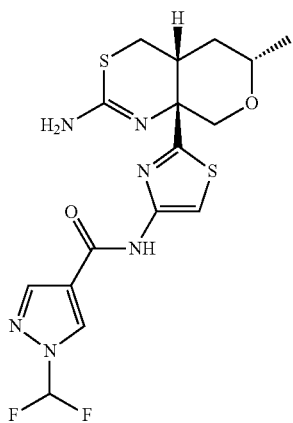 [SMILES: C[C@H]1C[C@H]2CSC(N)=N[C@@]2(c2nc(NC(=O)c3cnn(C(F)F)c3)cs2)CO1] | 428.8 |
| 84 | Example 4[1,3] | 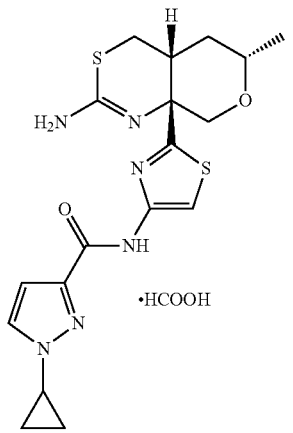 [SMILES: C[C@H]1C[C@H]2CSC(N)=N[C@@]2(c2nc(NC(=O)c3ccn(C4CC4)n3)cs2)CO1 ; "·HCOOH"] | 418.9 |
| 85 | Example 4[1] | 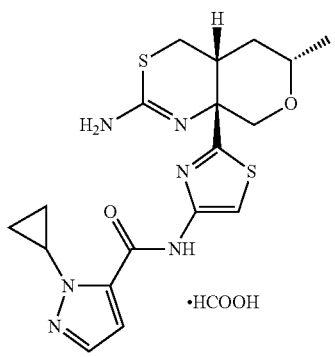 [SMILES: C[C@H]1C[C@H]2CSC(N)=N[C@@]2(c2nc(NC(=O)c3ccnn3C3CC3)cs2)CO1 ; "·HCOOH"] | 418.9 |

TABLE 2-continued

Method of Preparation, Structure, and Physicochemical Data for Examples 59-86

| Example Number | Method of Preparation; Non-commercial starting materials | Structure | Mass spectrum m/z [M + H]+ (unless otherwise indicated) |
|---|---|---|---|
| 86 | Example 4 | 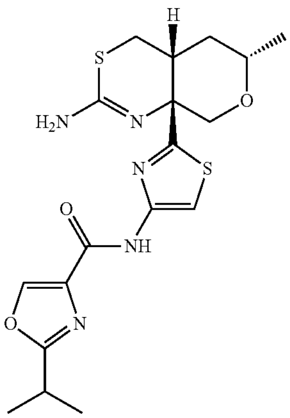 [SMILES: CC(C)c1nc(C(=O)Nc2csc([C@]34CO[C@@H](C)C[C@H]3CSC(N)=N4)n2)co1] | 421.8 |

[1] In this case, the final deprotection was carried out using hydrazine in ethanol, rather than methoxylamine hydrochloride.
[2] Methyl 1H-pyrazole-4-carboxylate was reacted with cyclopropylboronic acid and copper(II) acetate to generate methyl 1-cyclopropyl-1H-pyrazole-4-carboxylate, which was hydrolyzed with lithium hydroxide to afford 1-cyclopropyl-1H-pyrazole-4-carboxylic acid.
[3] Reaction of methyl 1H-pyrazole-3-carboxylate with potassium cyclopropyl(trifluoro)borate and copper(II) acetate provided methyl 1-cyclopropyl-1H-pyrazole-3-carboxylate, which was hydrolyzed with lithium hydroxide to afford the requisite 1-cyclopropyl-1H-pyrazole-3-carboxylic acid.

Biological Assays

BACE1 Cell-Free Assay:

Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 µM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 µL assay buffer [100 mM sodium acetate, pH 4.5 (brought to pH with acetic acid), and 0.001% Tween-20]. Plates are covered and incubated for 3 hours at 37° C. The reaction is stopped with the addition of 30 µL of 1.5 µM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

TABLE 3

Biological Data and IUPAC Names for Examples 1-109

| Example Number | BACE1 Cell-free Assay $IC_{50}$ (µM)[a] | IUPAC Name |
|---|---|---|
| 1 | 0.041[b] | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide |
| 1•HCl | 0.031[b] | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide, hydrochloride salt |

TABLE 3-continued

Biological Data and IUPAC Names for Examples 1-109

| Example Number | BACE1 Cell-free Assay IC$_{50}$ (µM)$^a$ | IUPAC Name |
|---|---|---|
| 2 | 0.073$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyrazine-2-carboxamide |
| 3 | 0.007$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide |
| 4 | 0.009$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide |
| 5 | 0.022$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyanopyridine-2-carboxamide |
| 6 | 0.004$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-chloro-1-(difluoromethyl)-1H-pyrazole-3-carboxamide |
| 7 | 0.033$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloropyridine-2-carboxamide |
| 7•HCl | 0.019 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloropyridine-2-carboxamide, hydrochloride salt |
| 8 | 0.011$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(difluoromethyl)-1,3-oxazole-4-carboxamide |
| 9 | 0.189$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide |
| 10 | 0.536 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxypyrazine-2-carboxamide |
| 11 | 0.315 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(fluoromethyl)pyrazine-2-carboxamide |
| 12 | 0.280 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoroethoxy)pyrazine-2-carboxamide |
| 13 | 0.090 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoro-3-methylpyridine-2-carboxamide, formate salt |
| 14 | 0.866 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-fluorobenzamide, formate salt |
| 15 | 0.145$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethyl)pyrazine-2-carboxamide |
| 16 | 0.193 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)pyrazine-2-carboxamide, formate salt |
| 17 | 0.054 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)pyridine-2-carboxamide |
| 18 | 0.153 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3,5-difluoropyridine-2-carboxamide |
| 19 | 0.259 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxypyridine-2-carboxamide |
| 20 | 0.108$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethoxy)pyridine-2-carboxamide |
| 21 | 0.106 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-(difluoromethoxy)benzamide |
| 22 | 0.013 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(but-2-yn-1-yloxy)pyrazine-2-carboxamide |
| 23 | 1.00 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrazolo[1,5-a]pyridine-2-carboxamide |
| 24 | 0.081 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-pyrazole-3-carboxamide |

TABLE 3-continued

Biological Data and IUPAC Names for Examples 1-109

| Example Number | BACE1 Cell-free Assay IC$_{50}$ (μM)$^a$ | IUPAC Name |
|---|---|---|
| 25 | 0.074 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethyl)pyridine-2-carboxamide |
| 26 | 0.068 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(fluoromethoxy)pyridine-2-carboxamide |
| 27 | 1.31 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-cyclopropyl-1,3-oxazole-4-carboxamide |
| 28 | 0.647 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrazine-2-carboxamide |
| 29 | 1.99 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,3-dimethyl-1H-pyrazole-4-carboxamide |
| 30 | 2.16 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyridazine-3-carboxamide |
| 31 | 3.82 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyclopropyl-1,2-oxazole-3-carboxamide |
| 32 | 1.40$^c$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(trifluoromethyl)-1,2-oxazole-3-carboxamide, trifluoroacetate salt |
| 33 | 34.1 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclobutyl-1H-imidazole-4-carboxamide |
| 34 | 1.48 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-cyclobutyl-1-methyl-1H-pyrazole-5-carboxamide |
| 35 | 5.86 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(methoxymethyl)-1,2-oxazole-3-carboxamide |
| 36 | 1.41 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-6-oxo-1,6-dihydropyridine-3-carboxamide |
| 37 | 0.485 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoroethoxy)pyridine-2-carboxamide, formate salt |
| 38 | 0.145 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-methyl-5-(trifluoromethyl)-1,3-oxazole-4-carboxamide, trifluoroacetate salt |
| 39 | 0.369 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-ethyl-1-methyl-1H-pyrazole-5-carboxamide, trifluoroacetate salt |
| 40 | 0.134 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-methyl-2H-1,2,3-triazole-4-carboxamide, trifluoroacetate salt |
| 41 | 0.364 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,3-dimethyl-1H-pyrazole-5-carboxamide, trifluoroacetate salt |
| 42 | 0.341 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-ethyl-1,3-oxazole-4-carboxamide, trifluoroacetate salt |
| 43 | 0.435 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,4-triazole-3-carboxamide, trifluoroacetate salt |
| 44 | 0.185 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoroethoxy)pyridine-2-carboxamide |
| 45 | 0.023$^b$ | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide |
| 46 | 0.320 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxy-3-methylpyrazine-2-carboxamide |

TABLE 3-continued

Biological Data and IUPAC Names for Examples 1-109

| Example Number | BACE1 Cell-free Assay IC$_{50}$ (μM)$^a$ | IUPAC Name |
| --- | --- | --- |
| 47 | 0.101 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methoxy-3-methylpyridine-2-carboxamide |
| 48 | 0.232 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-6-(difluoromethoxy)pyridine-3-carboxamide |
| 49 | 0.103 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-methyl-1,3-oxazole-4-carboxamide |
| 50 | 0.189 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(trifluoromethyl)-1,3-oxazole-4-carboxamide |
| 51 | 0.098 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-methyl-1,2,4-oxadiazole-5-carboxamide |
| 52 | 0.091 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methyl-1,2,4-oxadiazole-3-carboxamide |
| 53 | 0.065 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2,5-dimethyl-1,3-oxazole-4-carboxamide |
| 54 | 0.161 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyclopropylmethoxy)pyrazine-2-carboxamide |
| 55 | 0.519 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyclopropyloxy)pyrazine-2-carboxamide |
| 56 | 0.360 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-{[(2R)-2-fluoropropyl]oxy}pyrazine-2-carboxamide |
| 57 | 0.372 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-{[(2S)-2-fluoropropyl]oxy}pyrazine-2-carboxamide |
| 58 | 0.161 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide |
| 59 | 0.740 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2,4-dimethyl-1,3-oxazole-5-carboxamide, trifluoroacetate salt |
| 60 | 3.84 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-3-(trifluoromethyl)-1H-pyrazole-4-carboxamide, trifluoroacetate salt |
| 61 | 1.83 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(propan-2-yl)-1H-imidazole-4-carboxamide, trifluoroacetate salt |
| 62 | 9.69 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(2-methylpropyl)-1,2-oxazole-3-carboxamide, trifluoroacetate salt |
| 63 | 3.94 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-pyrazole-4-carboxamide, trifluoroacetate salt |
| 64 | 2.62 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methyl-1,2-oxazole-3-carboxamide, trifluoroacetate salt |
| 65 | 51.0 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-5-(2-methylpropyl)-1H-pyrazole-3-carboxamide, trifluoroacetate salt |
| 66 | 0.575 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrimidine-4-carboxamide, trifluoroacetate salt |
| 67 | 5.04 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-methyl-1,2-oxazole-5-carboxamide, trifluoroacetate salt |

TABLE 3-continued

Biological Data and IUPAC Names for Examples 1-109

| Example Number | BACE1 Cell-free Assay IC$_{50}$ (µM)$^a$ | IUPAC Name |
|---|---|---|
| 68 | 2.11 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-methylpyrazine-2-carboxamide, trifluoroacetate salt |
| 69 | 6.20 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5,6-dihydro-4H-pyrrolo[1,2-b]pyrazole-2-carboxamide, trifluoroacetate salt |
| 70 | 10.4 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-3-(propan-2-yl)-1H-pyrazole-5-carboxamide, trifluoroacetate salt |
| 71 | 9.26 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-ethyl-1,2-oxazole-5-carboxamide, trifluoroacetate salt |
| 72 | 7.48 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-ethyl-1H-pyrazole-4-carboxamide, trifluoroacetate salt |
| 73 | 12.4 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,5-dimethyl-1H-pyrazole-3-carboxamide, trifluoroacetate salt |
| 74 | 4.56 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,4-triazole-5-carboxamide, trifluoroacetate salt |
| 75 | 18.2 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-imidazole-4-carboxamide, trifluoroacetate salt |
| 76 | 28.1 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methyl-1H-1,2,3-triazole-4-carboxamide, trifluoroacetate salt |
| 77 | 0.777 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1,2-oxazole-3-carboxamide, trifluoroacetate salt |
| 78 | 1.49 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3,3-difluorocyclobutanecarboxamide, trifluoroacetate salt |
| 79 | 1.08 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}pyrimidine-2-carboxamide, trifluoroacetate salt |
| 80 | 8.07 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-4-carboxamide |
| 81 | 3.38 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-chloro-1-methyl-1H-pyrazole-3-carboxamide |
| 82 | 1.08 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-cyclopropylpyrazine-2-carboxamide, hydrochloride salt |
| 83 | 0.671 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-1H-pyrazole-4-carboxamide |
| 84 | 1.66 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-3-carboxamide, formate salt |
| 85 | 4.24 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyclopropyl-1H-pyrazole-5-carboxamide, formate salt |
| 86 | 16.2 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(propan-2-yl)-1,3-oxazole-4-carboxamide |
| 87 | 0.398 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(2,2-difluoroethyl)-1H-pyrazole-3-carboxamide |
| 88 | 0.418 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(2-methoxyethyl)-1H-pyrazole-3-carboxamide |
| 89 | 0.017 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(prop-2-yn-1-yl)-1H-pyrazole-3-carboxamide |

TABLE 3-continued

Biological Data and IUPAC Names for Examples 1-109

| Example Number | BACE1 Cell-free Assay IC$_{50}$ (μM)$^a$ | IUPAC Name |
|---|---|---|
| 90 | 0.175 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(methoxymethyl)-1,3-oxazole-4-carboxamide |
| 91 | 0.215 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(2,2,2-trifluoroethyl)-1,3-oxazole-4-carboxamide |
| 92 | 0.082 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(but-2-yn-1-yl)-1H-pyrazole-3-carboxamide |
| 93 | 0.376 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}cyclobutanecarboxamide |
| 94 | 0.018 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide |
| 95 | 0.075 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-4-(difluoromethyl)-1,3-oxazole-2-carboxamide |
| 96 | 0.002 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-(difluoromethyl)-4-methyl-1H-pyrazole-3-carboxamide |
| 97 | 0.177 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)pyrimidine-2-carboxamide |
| 98 | 0.033 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide |
| 99 | 0.025 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide |
| 100 | 0.220 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoro-2-methoxyethyl)pyrazine-2-carboxamide |
| 101 | 0.447 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(cyanomethoxy)pyridine-2-carboxamide |
| 102 | 0.012 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-2-(fluoromethyl)-5-methyl-1,3-oxazole-4-carboxamide |
| 103 | 0.282 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoro-2-methoxyethyl)pyridine-2-carboxamide |
| 104 | 0.308 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(1,1-difluoropropoxy)pyridine-2-carboxamide |
| 105 | 0.085 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}bicyclo[1.1.1]pentane-1-carboxamide |
| 106 | 0.348 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyanocyclopropanecarboxamide |
| 107 | 0.475 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}cyclopropanecarboxamide |
| 108 | 0.094 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-cyanocyclobutanecarboxamide |
| 109 | 0.461 | N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-1-methylcyclobutanecarboxamide |

$^a$Reported IC$_{50}$ values are the geometric mean of 2-4 determinations, unless otherwise indicated.
$^b$The reported IC$_{50}$ value is the geometric mean of ≥5 determinations.
$^c$The IC$_{50}$ value is from a single determination.

The following biological assays were used to generate the biological data as provided in Tables 4-6 provided hereinbelow.

BACE1 Cell-Free Assay:

Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY'EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 µM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 µL assay buffer [100 mM sodium acetate, pH 4.5 (brought to pH with acetic acid), and 0.001% Tween-20]. Plates are covered and incubated for 3 hours at 37° C. The reaction is stopped with the addition of 30 µL of 1.5 µM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

sAPPβ Whole-Cell Assay (WCA):

sAPPβ, the primary cleavage product of BACE1, was determined in H4 human neuroglioma cells over-expressing the wild-type human $APP_{695}$. Cells were treated for 18 h with compound in a final concentration of 1% DMSO. sAPPβ levels were measured by ELISA with a capture APP N-terminal antibody (Affinity BioReagents, OMA1-03132), wild-type sAPPβ-specific reporter antibody p192 (Elan), and tertiary anti-rabbit-HRP (GE Healthcare). The colorimetric reaction was read by an EnVision (PerkinElmer) plate-reader.

BACE2/BACE1 Binding Ratio:

The BACE1 and BACE2 binding assays measured beta-site amyloid precursor protein-cleaving enzyme (BACE) binding as a decrease in the counts of radioligand bound in a scintillation proximity assay (SPA). Utilizing a radiolabeled small molecule BACE active site binding inhibitor and crude HEK cell membrane preparations over-expressing full length BACE1 or BACE2, the binding of enzyme by test compound was monitored as a reduction of specific counts bound at pH 6.0. Full length human BACE1 or BACE2 over-expressed in HEK cells was prepared by Pfizer scientists. Frozen stock cell paste was reacted in 50 mM sodium acetate buffer (pH=6.0) containing 3H-(4aR,6R,8aS)-8a-(2,4-difluorophenyl)-6-(1-methyl-1H-pyrazol-4-yl)-4,4a,5,6,8,8a-hexahydropyrano[3,4-d][1,3]thiazin-2-amine ligand, SPA bead and 60 µM to 600 pM of test compound in an assay volume of 27 uL. The compound plate also contained positive (BACE inhibitor) and negative (DMSO) control wells. The binding was carried out at room temperature for 30 minutes and then the plates were read on a TriLux Microbeta reader to determine the number of counts bound. The raw data was converted to percent effect compared to positive and negative control wells and the compound concentrations and % effect values for tested compounds were plotted to determine the 50% effect (IC50) with a four-parameter logistic dose response equation.

General Multi-Point Cocktail DDI $IC_{50}$ Assay Conditions:

Standard marker activity substrates are incubated with pooled human liver microsomes (HL-MIX-102) in the presence of NADPH (1.2 mM) in 100 mM $KH_2PO_4$, pH 7.4 containing 3.3 mM $MgCl_2$ at 37° C. The incubation volume is 0.1 mL, utilizing a 384-well plate format. The microsomal protein concentrations (0.1 mg/mL) and P450 concentration (0.035 µM) was used for each probe substrate at the following concentrations [tacrine (1A2) 2 uM; diclofenac (2C9) 5 µM; dextromethorphan (2D6) 5 µM; midazolam (3A4) 2 µM; taxol (2C8) 5 µM; S-mephenytoin (2C19) 40 µM]. Substrate concentrations are near $K_m$ values that had been previously determined and incubation times are selected based on determinations of reaction velocity linearity. Each test compound/prototypical inhibitors are tested at a concentration range of 0-30 µM in triplicate, in final vehicle solvent concentrations of 0.9% acetonitrile and 0.1% DMSO. Incubations are initiated with the addition of NADPH. At the end of the incubation period, termination solvent containing internal standard is added, the terminated incubation mixture is centrifuged to precipitate microsomal protein. Samples are directly injected on an HPLC/MS/MS system. A Biomek FX workstation is used for liquid handling and sample incubation.

Pgp liability MDR1 Er:

MDR1 Efflux Ratio (MDR Er) from MDR1-transfected MDCK line cell line represents the ratio of permeability, Papp BA/AB. Procedure utilized from (Feng, B.; Mills, J. B.; Davidson, R. E.; Mireles, R. J.; Janiszewski, J. S.; Troutman, M. D.; de Morais, S. M. In vitro P-glycoprotein assays to predict the in vivo interactions of P-glycoprotein with drugs in the central nervous system. *Drug Metab. Dispos.* 2008, 36, 268-275.

hERG Patch Clamp Assay:

All testing was carried out in CHO cells transfected with the hERG gene purchased from Millipore (PrecisiON hERG-CHO Recombinant Cell Line CYL3038). The cell line was grown in DMEM/F-12, GlutaMAX™ with 10% fetal bovine serum, 1% Penicillin-Streptomycin, 1% Geneticin and 1% of 1M HEPES buffer solution, and maintained at approximately 37° C. in a humidified atmosphere containing 5% carbon dioxide. The cells were passaged every 3-5 days based on confluency. On the day of the experiment, 50%-80% confluent cells were harvested from a 175 $cm^2$ culture flask using Detachin™. After 10 minutes of exposure to Detachin™ at 37° C., the cells were centrifuged for 1 minute at 1000 RPM. The supernatant was removed and the cell pellet was reconstituted in 5-8 mL of serum free media with 2.5% of 1M HEPES, placed on the Qstirrer™, and allowed to recover. After a ~30 minute recovery period, experiments were initiated.

hERG Potassium Channel Current Recordings and Data Analysis:

hERG current was elicited and recorded using the automated Qpatch HT™ system.[14] The suspended cells in the Qstirrer™ were transferred to 48 individual recording chambers on a Qplate 48™ containing extracellular recording saline composed of (in µM): 132 NaCl, 4 KCl, 1.8 $CaCl_2$, 1.2 $MgCl_2$, 10 HEPES, 11.1 Glucose, and adjusted to pH 7.35±0.1 with NaOH. The intracellular recording saline was composed of (in µM): 70 KF, 60 KCl, 15 NaCl, 5 EGTA, 5 HEPES, and adjusted to pH 7.2±0.1 with KOH. Membrane currents were recorded at room temperature. hERG current was elicited from a holding potential of −80 mV with a voltage step to +30 mV for 1 second, followed by a ramp back to −80 mV at 0.55 mV/ms. Test pulses were delivered at a frequency of 0.25 Hz. Up to 4 different concentrations were studied on each cell, each exposure lasting 5 minutes or until steady-state effects were observed. In a separate set of experiments, full concentration-response relationships were determined for the positive control, Cisapride, and an $IC_{50}$ was reported in this study. Using Sophion Qpatch Assay Software, the amplitude of the peak outward hERG current upon repolarizing ramp was measured. Current amplitude was determined by taking the average of the last 5 current peaks under each treatment condition. Percent inhibition was determined by taking the ratio of the current measured at steady state in the presence of test article ($I_{Test\ article}$) versus the control current ($I_{Control}$), and expressed as: % inhibition=100−($I_{Test\ article}/I_{Control}$)*100. When possible, a concentration-response curve was plotted and the data were fitted using Qpatch software to determine an $IC_{50}$. The P<0.05 was considered statistically significant.

GSH Incubation Assay:

The test compound (10 μM in DMSO) was incubated with L-glutathione (50 mM, prepared in 100 mM potassium phosphate buffer) at 37° C. for 4 hours and then analyzed by HPLC-UV/MS/MS without work-up. Thermo Accela HPLC and Velos Pro Orbitrap Elite (S/N: SN05189B) operating in positive mode with a source voltage of 3.5 kV with data dependant processing. HPLC with a Phenomenox Kinetex $C_{18}$, 1.7 μM, 2.1×100 mm. column (P/N: 00D-4475-AN), 5% acetonitrile/95% 0.1% formic acid for 0.5 min then a 7.0 min linear gradient to 40% acetonitrile/60% 0.1% formic acid, 400 μL/min., column temperature 45° C. Product assignments were based on high resolution mass spectrometer fragmentation.

Tables 4-6, below, provide biological data for the compounds of examples 1, 2, 7 and 45 as well as comparator compounds 1-7. Comparator compounds 1-3 are novel compounds whereas comparator compounds 4-7 are the compounds of examples 58, 64, 42 and 6 of U.S. Pat. No. 8,198,269 and can be prepared as described therein.

Table 4, below, provides BACE1 Cell Free $IC_{50}$, sAPPβ Whole Cell $IC_{50}$ and BACE2/BACE1 Binding Ratio data for the compounds of Examples 1, 2, 7 and 45 and Comparators 1-7, whose structures are provided below. The data was obtained using the BACE1 Cell Free, sAPPβ Whole Cell and BACE2/BACE1 Ratio assays as described hereinabove.

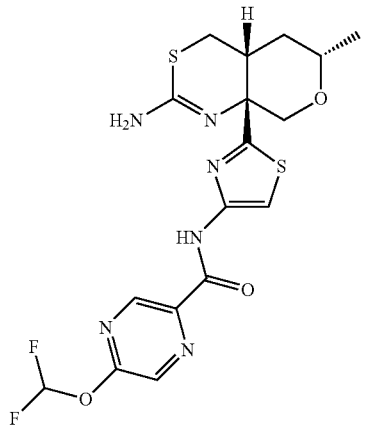

Example 2

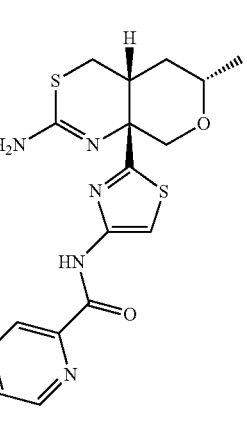

Example 7

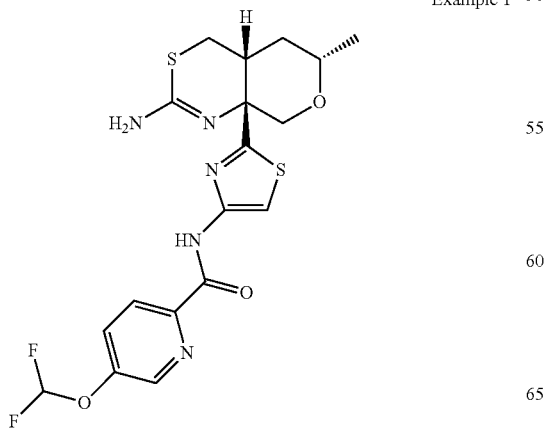

Example 1

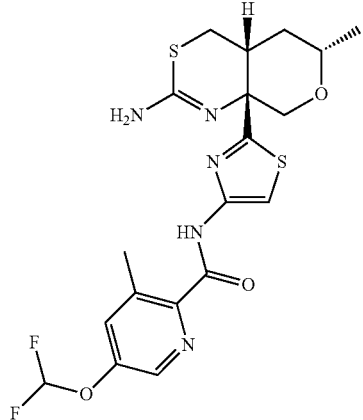

Example 45

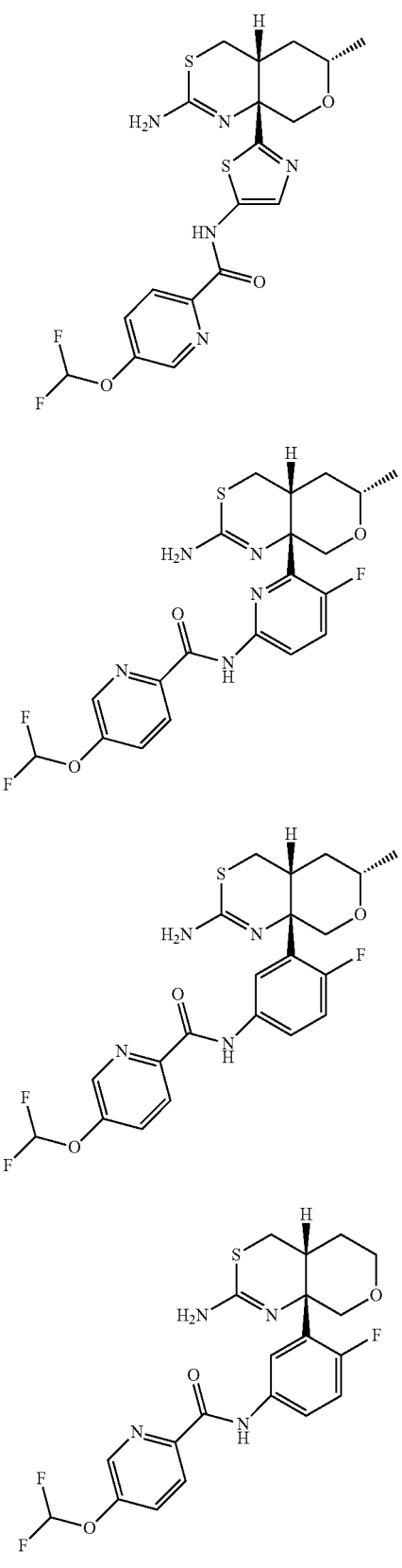
Ex. 58 pf U.S. Pat. No. 8,198,269
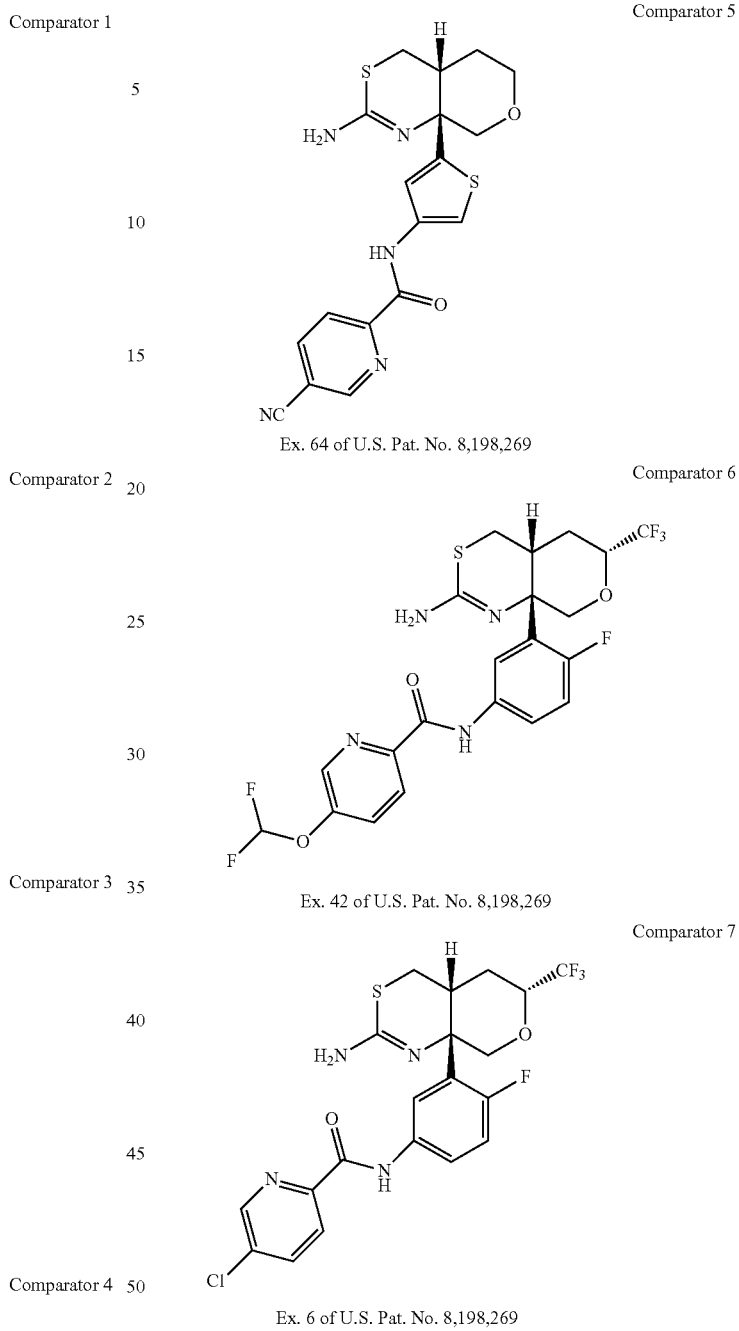
Ex. 64 of U.S. Pat. No. 8,198,269
Ex. 42 of U.S. Pat. No. 8,198,269
Ex. 6 of U.S. Pat. No. 8,198,269
TABLE 4
| Compound | BACE1 Cell Free IC$_{50}$ | sAPPβ Whole Cell IC$_{50}$ | BACE2/BACE1 Binding Ratio |
|---|---|---|---|
| Example 1 | 41 nM | 5 nM | 27.9 |
| Example 2 | 73 nM | 7 nM | 25.8 |
| Example 7 | 33 nM | 4 nM | 3.8 |
| Example 45 | 23 nM | 3 nM | 6.4 |
| Comparator 1 | >100 μM | 13.6 μM | 0.5 |
| Comparator 2 | 43 nM | 1 nM | 2.9 |
| Comparator 3 | 3 nM | <1 nM | ND |
| Comparator 4 (Ex. 58 of U.S. Pat. No. 8,198,269) | 9 nM | <1 nM | 2.1 |

TABLE 4-continued

| Compound | BACE1 Cell Free $IC_{50}$ | sAPPβ Whole Cell $IC_{50}$ | BACE2/BACE1 Binding Ratio |
| --- | --- | --- | --- |
| Comparator 5 (Ex. 64 of U.S. Pat. No. 8,198,269) | 19 nM | 2 nM | 3.1 |
| Comparator 6 (Ex. 42 of U.S. Pat. No. 8,198,269) | 6 nM | <1 nM | 1.0 |
| Comparator 7 (Ex. 6 of U.S. Pat. No. 8,198,269) | 1 nM | <1 nM | 1.0 |

The accumulation and aggregation of amyloid-β (Aβ) peptides is believed to be one of the underlying causes of Alzheimer's disease (AD), which is the most common reason for cognitive decline in the elderly.[1] AD pathology is characterized by the presence of extracellular plaques in the hippocampal and cortical regions of the brain, accompanied by intraneuronal neurofibrillary tangles and extensive neuronal loss.[2] Aβ, the major protein constituent of amyloid plaques, is derived from sequential cleavage of the type I integral membrane protein, amyloid precursor protein (APP), by two proteases: BACE1 and γ-secretase.[3] Proteolytic cleavage of APP by BACE1, a member of the aspartyl protease family of enzymes, takes place within the endosome at low pH, generating a soluble N-terminal ectodomain of APP (sAPPβ) and C-terminal fragment (C99).[4] Subsequent cleavage of the membrane-bound C99 fragment by γ-secretase liberates the various Aβ peptide species, of which $Aβ_{40}$ and $Aβ_{42}$ are the predominant forms.[5] The determination of BACE1 potency in a cell-free fluorescence polarization assay (BACE1 Cell Free) and whole cell assay (BACE1 WCA) in H4 human neuroglioma cells measuring sAPPβ is shown in Table 4. Those skilled in the art will appreciate that different assay formats are available to measure the inhibition of BACE1. One skilled in the art will appreciate that acceptable potency for inhibiting BACE1 for a viable drug candidate is typically less than 100 nM in both a cell free and whole cell assays. Surprisingly, there was a significant difference between the thiazole containing compounds with respect to the regioisomeric position of the amide linker. For example, the compounds of examples 1, 2, 7, and 45 display potent BACE1 inhibition while Comparator 1 is surprisingly and unexpectedly >1000 fold less active at BACE1, clearly showing the criticality that the position of the amide substitution on the thiazole has on the BACE1 potency of the compounds.

Selectivity for BACE1 inhibitors against related aspartyl proteases is an important factor for determining the potential safety for a viable drug candidate.[6] The related aspartyl protease BACE2 has recently been reported to impact pigmentation in cellular and in vivo models. For example, BACE2 processes pigment cell-specific melanocyte protein (PMEL) which is believed to play a role in melanogenesis.[7] The selectivity ratio for BACE2 to BACE1 inhibition was determined using a ratio of IC50 from respective binding assays as shown in Table 4. Surprisingly, there was a significant improvement in selectivity for BACE1 over BACE2 for examples 1, 2, and 45 relative to comparator compounds 4 through 7 which are the compounds of examples 58, 64, 42, and 6 from U.S. Pat. No. 8,198,269. Those skilled in the art will appreciate the potential impact of selectivity over BACE2 with respect to skin pigmentation changes in human clinical trials.

Table 5, below, provides HLM Clint, CYP2D6 $IC_{50}$ and observed glutathione (GSH) adduct data for the compounds of examples 1, 2, 7 and 45 and comparators 1-7, whose structures are provided below. The data was obtained using the General Multi-Point Cocktail DDI $IC_{50}$ and GSH incubation assays as described hereinabove.

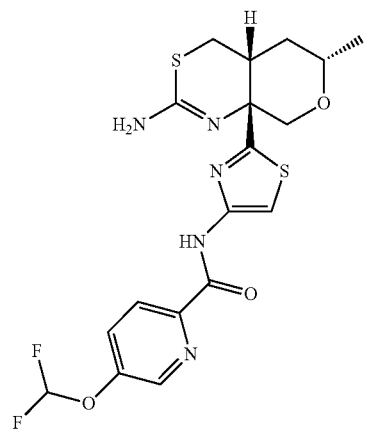

Example 1

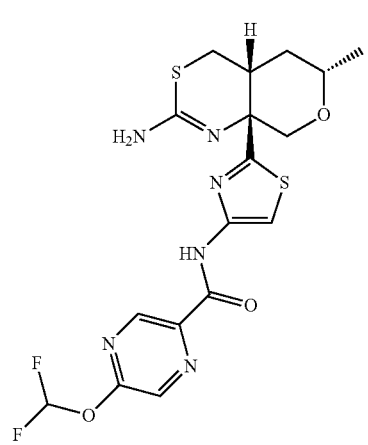

Example 2

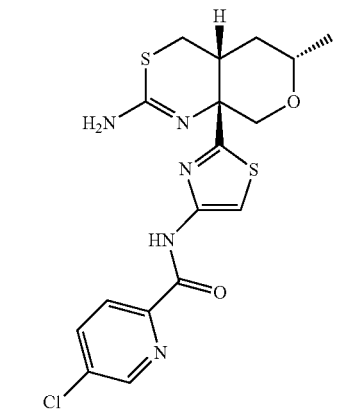

Example 7

Example 45
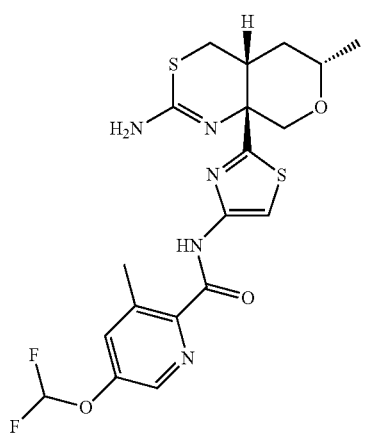
Comparator 1
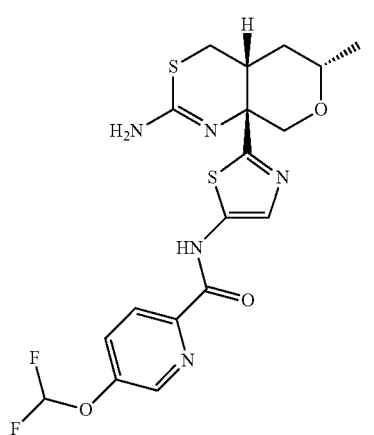
Comparator 2
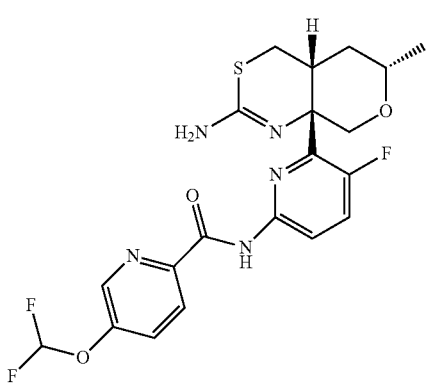
Comparator 3
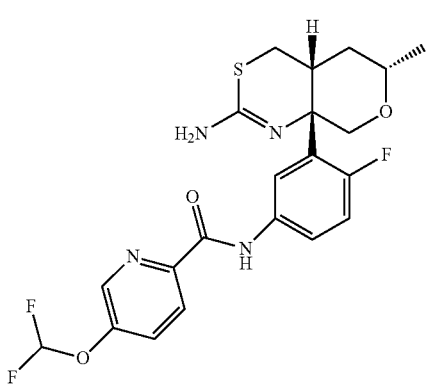
Comparator 4
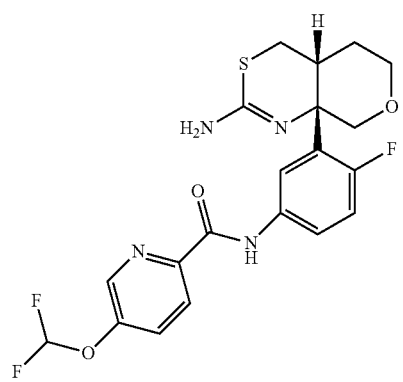
Ex. 58 pf U.S. Pat. No. 8,198,269
Comparator 5
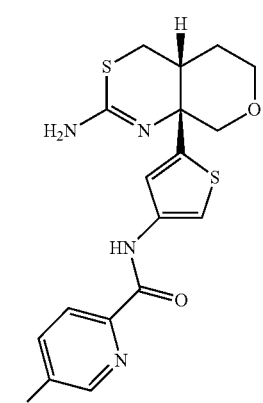
Ex. 64 of U.S. Pat. No. 8,198,269
Comparator 6
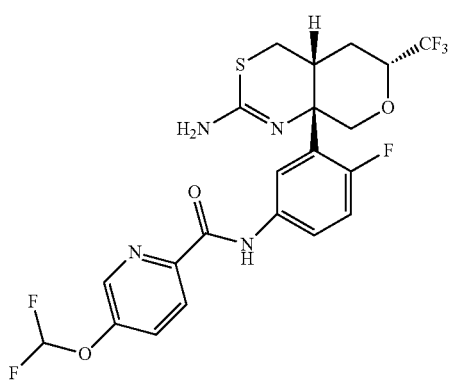
Ex. 42 of U.S. Pat. No. 8,198,269

-continued

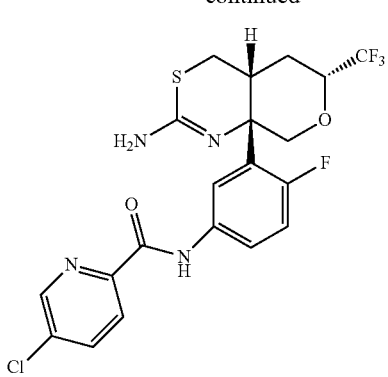

Comparator 7
Ex. 6 of U.S. Pat. No. 8,198,269

TABLE 5

| Compound | HLM CLint | CYP2D6 IC$_{50}$[a] | Observed GSH adducts[b] |
|---|---|---|---|
| Example 1 | <8 mL/min/kg | >30 µM | Negative |
| Example 2 | <8 mL/min/kg | >30 µM | Negative |
| Example 7 | <8 mL/min/kg | >30 µM | Negative |
| Example 45 | <8 mL/min/kg | >30 µM | Negative |
| Comparator 1 | <8 mL/min/kg | 14% inh @ 3 mM | Not Determined |
| Comparator 2 | 22.9 mL/min/kg | <30 nM | Not Determined |
| Comparator 3 | 19.8 mL/min/kg | <30 nM | Not Determined |
| Comparator 4 (Ex. 58 of U.S. Pat. No. 8,198,269) | 8.3 mL/min/kg | 65 nM | Not Determined |
| Comparator 5 (Ex. 64 of U.S. Pat. No. 8,198,269) | <8 mL/min/kg | <10% inh @ 3 µM | Positive |
| Comparator 6 (Ex. 42 of U.S. Pat. No. 8,198,269) | <12.8 mL/min/kg | <30 nM | Not Determined |
| Comparator 7 (Ex. 6 of U.S. Pat. No. 8,198,269) | 34.4 mL/min/kg | <30 nM | Not Determined |

[a]CYP2D6 inhibition was obtained by measuring inhibition of 5 uM Dextromethorphan in pooled HLM (HL-MIX-102);
[b]Incubations with glutathione (50 mM) at 37° C. in buffer for 4 hours.

The hepatic clearance of BACE1 inhibitors is an important consideration for the selection of viable drug candidates. Those skilled in the art will appreciate the negative impact of higher clearance compounds on projected human dose and dosing regimen in human. In general, compounds with low clearance (CLint<8 mL/min/Kg) in human liver microsomes are more desirable than higher clearance compounds (CLint>15 mL/min/kg). From the data presented above it will be apparent to those skilled in the art that the compounds of examples 1, 2, 7 and 45 each possess an advantageously low hepatic clearance profile with a Clint<8 mL/min/Kg. The low hepatic clearance values exhibited by the compounds of examples 1, 2, 7 and 45 should allow for acceptable dosages and dosing regimens for use of these compounds in humans.

The inhibition of CYP-P450s increases the risk for clinical drug-drug interactions (DDIs). For example, inhibition of CYP2D6 is of particular concern due to the potential for victim based DDIs and variable clinical exposure due to polymorphic nature of this enzyme.[8] Those skilled in the art will appreciate the desire to eliminate the potential to inhibit CYP2D6 in a viable clinical candidate. As shown in Table 5, examples 1, 2, 7, and 45 display IC50s>30 µM for inhibiting CYP2D6 relative to comparators 2, 3, and comparators 4, 6 and 7 (the compounds of examples 58, 42, and 6 from U.S. Pat. No. 8,198,269) which display IC50s<100 nM. From the data presented above it will be apparent to those skilled in the art that the compounds of examples 1, 2, 7 and 45 each possess an advantageously low CYP2D6 inhibitor profile and thus these compounds minimize the risk of DDIs which could result from inhibition of that CYP-P450 isozyme in a patient.

The potential clinical hepatotoxicity or drug induced liver injury (DILI) is one of the major reasons for the withdrawal of compounds from the market.[9] Those skilled in the art will appreciate that bioactivation or covalent binding of compounds to proteins is a potential mechanism for hepatotoxicity. A common assay for understanding the impact of covalent binding is to monitor for the formation of glutathione (GSH) adducts. For examples 1, 2, 7, and 45 in Table 5, the formation of GSH adducts was not detected following incubations. This is advantageous as it indicates that the compounds of examples 1, 2, 7 and 45 are not compounds which would lead to the potential for a glutathione-adduct induced mechanism of hepatotoxicity. However, incubation of comparator 5 (example 64 from U.S. Pat. No. 8,198,269) in human liver microsomes in the presence of GSH showed the formation of chemical adducts which has the potential to lead to DILI.

Table 6, below, provides hERG IC$_{50}$, Pgp liability MDR1 Er and pKa data as well as an indication of an aniline structural alert and for the compounds of examples 1, 2, 7 and 45 and comparators 1-7, whose structures are provided below. The hERG IC50 and Pgp liability MDR1 Er data was obtained using the hERG and Pgp liability MDR1 Er assays as described hereinabove.

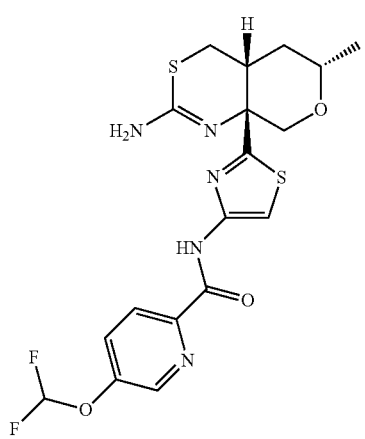

Example 1

Example 2
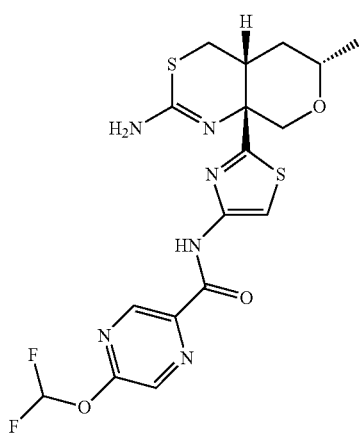
Example 7
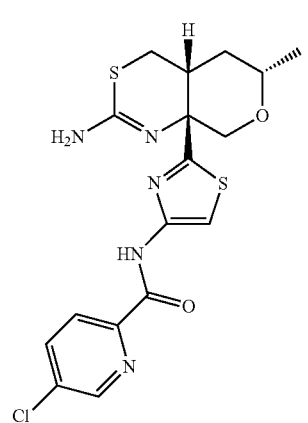
Example 45
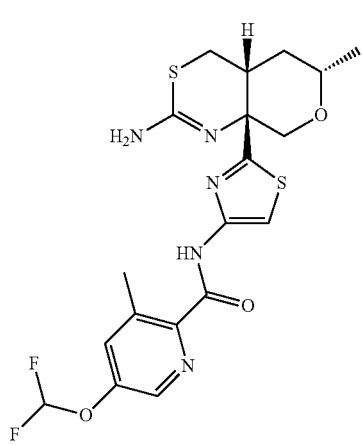
Comparator 1
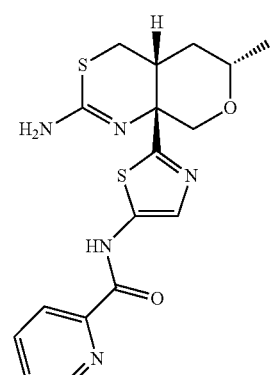
Comparator 2
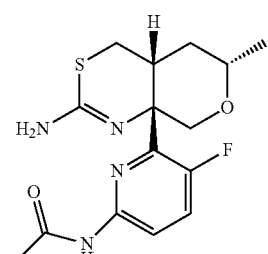
Comparator 3
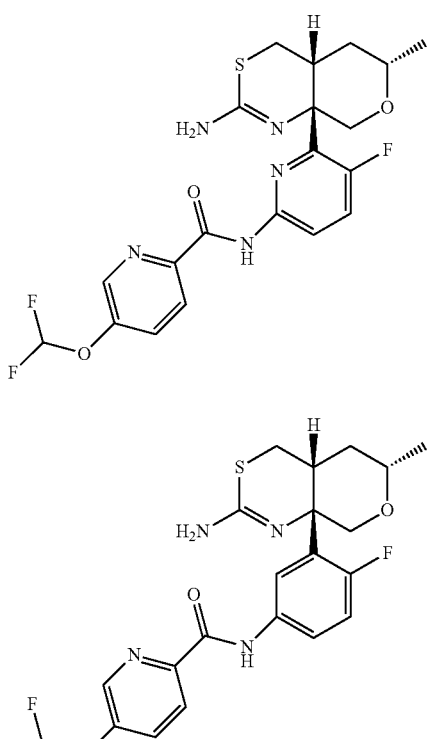
Comparator 4
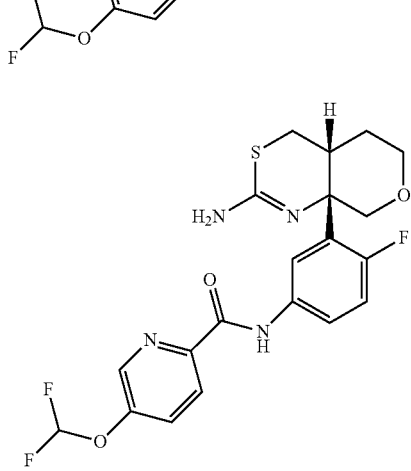
Ex. 58 of U.S. Pat. No. 8,198,269

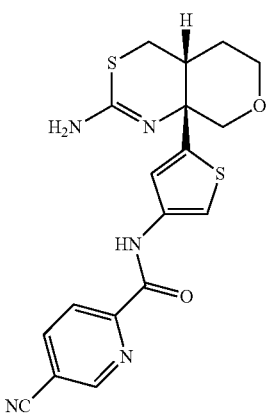

Ex. 64 of U.S. Pat. No. 8,198,269

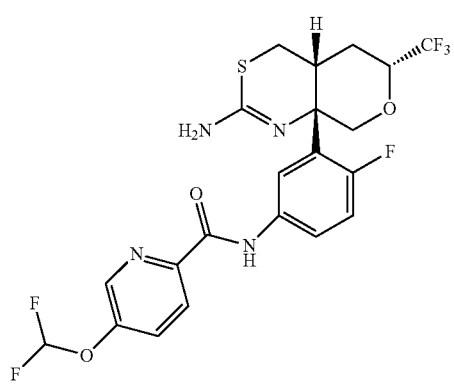

Ex. 42 of U.S. Pat. No. 8,198,269

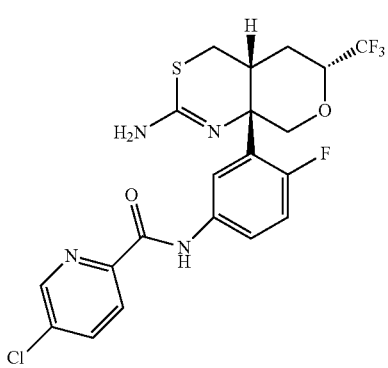

Ex. 6 of U.S. Pat. No. 8,198,269

TABLE 6

| Compound | hERG IC$_{50}$[a] | Pgp liability MDR1 Er[b] | pKa[c] | Aniline Structural Alert |
|---|---|---|---|---|
| Example 1 | 9.9 μM | 2.2 | 6.8 | No |
| Example 2 | 23.6 μM | 1.8 | 6.8 | No |
| Example 7 | 9.0 μM | 2.4 | 6.9 | No |
| Example 45 | 9.6 μM | 2.9 | 6.9 | No |
| Comparator 1 | ND | 7.1 | 7.0 | No |
| Comparator 2 | ND | 14.2 | 8.7 | No |

TABLE 6-continued

| Compound | hERG IC$_{50}$[a] | Pgp liability MDR1 Er[b] | pKa[c] | Aniline Structural Alert |
|---|---|---|---|---|
| Comparator 3 | 0.4 μM | 5.1 | 8.3 | Yes |
| Comparator 4 (Ex. 58 of U.S. Pat. No. 8,198,269) | 0.5 μM | 6.8 | 8.2 | Yes |
| Comparator 5 (Ex. 64 of U.S. Pat. No. 8,198,269) | 1.8 μM | 8.9 | 8.1 | No |
| Comparator 6 (Ex. 42 of U.S. Pat. No. 8,198,269) | ND | 3.2 | 7.7 | Yes |
| Comparator 7 (Ex. 6 of U.S. Pat. No. 8,198,269) | 0.2 μM | 3.03 | 8.2 | Yes |

[a]hERG testing was conducted in CHO cell transfected with hERG gene and current was elicited and recorded using the automated Qpatch HT ™ system.
ND means not determined.
[b]MDR1 Efflux Ratio (MDR Er) from MDR1-transfected MDCK line cell line represents the ratio of permeability, Papp BA/AB. Procedure utilized from (Feng, B.; Mills, J. B.; Davidson, R. E.; Mireles, R. J.; Janiszewski, J. S.; Troutman, M. D.; de Morais, S. M. In vitro P-gylcoprotein assays to predict the in vivo interactions of P-gylcoprotein with drugs in the central nervous system. *Drug Metab. Dispos.* 2008, 36, 268-275.
[c]Measurement determined at Analyza.

Understanding potential cardiovascular risks such as QT prolongation as a result of inhibition of hERG (human ether a go-go) is an important factor in selecting compounds for clinical development.[10] Those skilled in the art will appreciate that a compound with appropriate cardiovascular safety margins is relative to the targeted plasma concentrations in human. In addition, an important factor in reducing the targeted plasma concentration is optimizing brain penetration by reducing activity against efflux transporters located at the blood brain barrier such as P-glycoprotein (Pgp).[11] Those skilled in the art will appreciate that the potential for CNS penetration can be assessed in vitro by determining whether a compound can be subjected to Pgp efflux and that compounds can be assessed using various known in vitro Pgp assays. One such in vitro assay is the Pgp MDR1 Er assay described above. In general, compounds with low efflux potential (Er<2.5) as measured in the MDR1 assay are highly desirable when combined with weak inhibition of the hERG channel (hERG IC50>5 μM). Examples 1, 2, 7, and 45 in Table 6, advantageously show both weak inhibition of the hERG channel (hERG IC50 >5 μM) as well as low Pgp efflux potential (MDR1 Er<2.5).

Those skilled in the art will appreciate the impact of a highly basic pK$_a$ on activity at the hERG channel, P-gp transporters, and inhibition of CYP2D6.[12] Surprisingly, the thiazole group present in examples 1, 2, 7, and 45 significantly lowers the pKa of these compounds relative to comparators 2-7 as shown in Table 6. This result was unexpected based on the increase in pKa (8.7) for the pyridine containing compound comparator 2.

Those skilled in the art will also appreciate that structural alerts may be associated with idiosyncratic adverse drug reactions (IADRs). For example, compounds containing an aniline structural alert have been withdrawn from commercial use or have received a black box warning for an IADR.[13] Those skilled in the art will appreciate that predicting IADR is challenging but a key consideration to avoiding a potential IADR is to remove structural alerts from viable clinical candidates. Examples 58, 42, and 6 from U.S. Pat. No. 8,198,269 each have an aniline structural alert.

1. (a) Hardy, J.; Allsop, D., Amyloid deposition as the central event in the aetiology of Alzheimer's disease. *Trends Pharmacol. Sci.* 1991, 12 (10), 383; (b) Walsh, D. M.; Minogue, A. M.; Sala Frigerio, C.; Fadeeva, J. V.; Wasco, W.; Selkoe, D. J., The APP family of proteins: similarities and differences. *Biochem. Soc. Trans.* 2007, 35 (2), 416-420.
2. Tanzi, R. E.; Bertram, L., Twenty years of the Alzheimer's disease amyloid hypothesis: a genetic perspective. *Cell* 2005, 120 (4), 545-55.
3. De Strooper, B., Proteases and proteolysis in Alzheimer disease: a multifactorial view on the disease process. *Physiol Rev* 2010, 90 (2), 465-94.
4. Vassar, R.; Kovacs, D. M.; Yan, R.; Wong, P. C., The beta-secretase enzyme BACE in health and Alzheimer's disease: regulation, cell biology, function, and therapeutic potential. *J. Neurosci.* 2009, 29 (41), 12787-94.
5. Marks, N.; Berg, M. J., *Neurochem. Res.* 2010, 35 (2), 181.
6. Vassar, R.; Kuhn, P.-H.; Haass, C.; Kennedy, M. E.; Rajendran, L.; Wong, P. C.; Lichtenthaler, S. F., Function, therapeutic potential and cell biology of BACE proteases: current status and future prospects. *J. Neurochem.* 2014, 130 (1), 4-28.
7. Rochin, L.; Hurbain, I.; Serneels, L.; Fort, C.; Watt, B.; Leblanc, P.; Marks, M. S.; De Strooper, B.; Raposo, G.; van Niel, G., BACE2 processes PMEL to form the melanosome amyloid matrix in pigment cells. *Proc. Natl. Acad. Sci. U.S.A.* 2013, 110 (26), 10658-10663, S10658/1-S10658/7.
8. (a) Rendic, S.; Di Carlo, F. J., Human cytochrome P450 enzymes: a status report summarizing their reactions, substrates, inducers, and inhibitors. *Drug Metab. Rev.* 1997, 29 (1 & 2), 413-580; (b) Teh, L. K.; Bertilsson, L., Pharmacogenomics of CYP2D6: molecular genetics, interethnic differences and clinical importance. *Drug Metab. Pharmacokinet.* 2012, 27 (1), 55-67; (c) Bertilsson, L.; Dahl, M.-L.; Dalen, P.; Al-Shurbaji, A., Molecular genetics of CYP2D6: clinical relevance with focus on psychotropic drugs. *Br. J. Clin. Pharmacol.* 2002, 53 (2), 111-122.
9. Sakatis, M. Z.; Reese, M. J.; Harrell, A. W.; Taylor, M. A.; Baines, I. A.; Chen, L.; Bloomer, J. C.; Yang, E. Y.; Ellens, H. M.; Ambroso, J. L.; Lovatt, C. A.; Ayrton, A. D.; Clarke, S. E., Preclinical Strategy to Reduce Clinical Hepatotoxicity Using in Vitro Bioactivation Data for >200 Compounds. *Chem. Res. Toxicol.* 2012, 25 (10), 2067-2082.
10. (a) Sanguinetti, M. C.; Tristani-Firouzi, M., hERG potassium channels and cardiac arrhythmia. *Nature (London, U. K.)* 2006, 440 (7083), 463-469; (b) Sanguinetti, M. C.; Jiang, C.; Curran, M. E.; Keating, M. T., A mechanistic link between an inherited and an acquired cardiac arrhythmia: HERG encodes the IKr potassium channel. *Cell* 1995, 81 (2), 299-307; (c) Roden, D. M., Drug-induced prolongation of the QT interval. *N. Engl. J. Med.* 2004, 350 (10), 1013-1022.
11. Doan, K. M. M.; Humphreys, J. E.; Webster, L. O.; Wring, S. A.; Shampine, L. J.; Serabjit-Singh, C. J.; Adkison, K. K.; Polli, J. W., Passive permeability and P-glycoprotein-mediated efflux differentiate central nervous system (CNS) and non-CNS marketed drugs. *J. Pharmacol. Exp. Ther.* 2002, 303 (3), 1029-1037.
12. (a) Jamieson, C.; Moir, E. M.; Rankovic, Z.; Wishart, G., Medicinal chemistry of hERG optimizations: Highlights and hang-ups. *J. Med. Chem.* 2006, 49 (17), 5029-5046; (b) Price, D. A.; Armour, D.; de Groot, M.; Leishman, D.; Napier, C.; Perros, M.; Stammen, B. L.; Wood, A., Overcoming hERG affinity in the discovery of maraviroc; a CCR5 antagonist for the treatment of HIV. *Curr. Top. Med. Chem. (Sharjah, United Arab Emirates)* 2008, 8 (13), 1140-1151; (c) Waring, M. J.; Johnstone, C., A quantitative assessment of hERG liability as a function of lipophilicity. *Bioorg. Med. Chem. Lett.* 2007, 17 (6), 1759-1764; (d) Ginman, T.; Viklund, J.; Malmstroem, J.; Blid, J.; Emond, R.; Forsblom, R.; Johansson, A.; Kers, A.; Lake, F.; Sehgelmeble, F.; Sterky, K. J.; Bergh, M.; Lindgren, A.; Johansson, P.; Jeppsson, F.; Faelting, J.; Gravenfors, Y.; Rahm, F., Core Refinement toward Permeable β-Secretase (BACE-1) Inhibitors with Low hERG Activity. *J. Med. Chem.* 2013, 56 (11), 4181-4205.
13. Kalgutkar, A. S., Should the Incorporation of Structural Alerts be Restricted in Drug Design? An Analysis of Structure-Toxicity Trends with Aniline-Based Drugs. *Curr Med Chem* 2015, 22 (4), 438-64.
14. Kutchinsky, J.; Friis, S.; Asmild, M.; Taboryski, R.; Pedersen, S.; Vestergaard, R. K.; Jacobsen, R. B.; Krzywkowski, K.; Schroder, R. L.; Ljungstrom, T.; Helix, N.; Sorensen, C. B.; Bech, M.; Willumsen, N. J., Characterization of Potassium Channel Modulators with QPatch Automated Patch-Clamp Technology: System Characteristics and Performance. *Assay Drug Dev. Technol.* 2003, 1 (5), 685-693.

We claim:

1. A method of treating Alzheimer's disease in a patient, the method comprising administering to the patient a therapeutically effective amount of a pharmaceutical combination, the pharmaceutical combination comprising a compound selected from the group consisting of N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide;

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; and N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer; and one or more additional pharmaceutical agent.

2. The method of claim 1 wherein the additional pharmaceutical agent is selected from the group consisting of an anti-obesity agent, an anti-diabetic agent, a lipid lowering agent, an anti-hypertensive agent, an acetylcholinesterase inhibitor, an antibody to amyloid-β, an amyloid-lowering or amyloid-inhibiting agent, an alpha-adrenergic receptor agonist, a beta-adrenergic blocking agent, an anticholinergic, an anticonvulsant, an antipsychotic, a calcium channel blocker, an O-methyltransferase inhibitor, a central nervous system stimulant, a corticosteroid, a dopamine receptor agonist or antagonist, a dopamine reuptake inhibitor, a gamma-aminobutyric receptor agonist, an immunosuppressant, an interferon, a muscarinic receptor agonist, a nicotinic receptor agonist, a norepinephrine reuptake inhibitor, a histamine 3 antagonist, a N-methyl-D-aspartate receptor antagonist, a monoamine oxidase inhibitor, a phosphodiesterase inhibitor, a serotonin 5-HT$_{1A}$ receptor antagonist, a serotonin 5-HT$_{2C}$ receptor agonist, a serotonin 5-HT$_4$ receptor agonist/antagonist, a serotonin 5-HT$_{3C}$ receptor antagonist, a serotonin 5-HT$_6$ receptor antagonist, a serotonin 5-HT reuptake inhibitor, a glycine transporter-1 inhibitor, a P450 inhibitor and an anti-tau agent.

3. The method of claim 2 wherein the additional pharmaceutical agent is an amyloid-lowering or amyloid-inhibiting agent which is selected from the group consisting of a BACE inhibitor, a gamma secretase modulator and a RAGE inhibitor.

4. The method of claim 1 in which the compound is N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

5. The method of claim 1 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide; or a tautomer thereof or a pharmaceutically acceptable salt of said compound or tautomer.

6. The method of claim 1 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide; or a tautomer thereof or a pharmaceutically acceptable salt of said compound or tautomer.

7. The method of claim 1 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide; or a tautomer thereof or a pharmaceutically acceptable salt of said compound or tautomer.

8. The method of claim 1 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide; or a tautomer thereof or a pharmaceutically acceptable salt of said compound or tautomer.

9. The method of claim 1 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; or a tautomer thereof or a pharmaceutically acceptable salt of said compound or tautomer.

10. The method of claim 1 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer.

11. A method of inhibiting the production of an Aβ peptide in a patient, the method comprising administering to the patient a pharmaceutical combination, the pharmaceutical combination comprising a compound selected from the group consisting of N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide;

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide;

N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-fluoropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; and N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer; and one or more additional pharmaceutical agent.

12. The method of claim 11 wherein the additional pharmaceutical agent is selected from the group consisting of an anti-obesity agent, an anti-diabetic agent, a lipid lowering agent, an anti-hypertensive agent, an acetylcholinesterase inhibitor, an antibody to amyloid-β, an amyloid-lowering or amyloid-inhibiting agent, an alpha-adrenergic receptor agonist, a beta-adrenergic blocking agent, an anticholinergic, an anticonvulsant, an antipsychotic, a calcium channel blocker, an O-methyltransferase inhibitor, a central nervous system stimulant, a corticosteroid, a dopamine receptor agonist or antagonist, a dopamine reuptake inhibitor, a gamma-aminobutyric receptor agonist, an immunosuppressant, an interferon, a muscarinic receptor agonist, a nicotinic receptor agonist, a norepinephrine reuptake inhibitor, a histamine 3 antagonist, a N-methyl-D-aspartate receptor antagonist, a monoamine oxidase inhibitor, a phosphodiesterase inhibitor, a serotonin 5-HT$_{1A}$ receptor antagonist, a serotonin 5-HT$_{2C}$ receptor agonist, a serotonin 5-HT$_4$ receptor agonist/antagonist, a serotonin 5-HT$_{3C}$ receptor antagonist, a serotonin 5-HT$_6$ receptor antagonist, a serotonin 5-HT reuptake inhibitor, a glycine transporter-1 inhibitor, a P450 inhibitor and an anti-tau agent.

13. The method of claim 12 wherein the additional pharmaceutical agent is an amyloid-lowering or amyloid-inhibiting agent which is selected from the group consisting of a BACE inhibitor, a gamma secretase modulator and a RAGE inhibitor.

14. The method of claim 11 in which the compound is N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

15. The method of claim 11 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide; or a tautomer thereof or a pharmaceutically acceptable salt of said compound or tautomer.

16. The method of claim 11 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide; or a tautomer thereof or a pharmaceutically acceptable salt of said compound or tautomer.

17. The method of claim 11 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide; or a tautomer thereof or a pharmaceutically acceptable salt of said compound or tautomer.

18. The method of claim 11 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide; or a tautomer thereof or a pharmaceutically acceptable salt of said compound or tautomer.

19. The method of claim 11 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; or a tautomer thereof or a pharmaceutically acceptable salt of said compound or tautomer.

20. The method of claim 11 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer.

21. A method of inhibiting β-site amyloid precursor protein (APP) Cleaving Enzyme 1 (BACE1) in a patient, the method comprising administering to the patient a pharmaceutical combination, the combination comprising a compound selected from the group consisting of
  N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;
  N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide;
  N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide;
  N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide;
  N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;
  N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; and
  N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer; and one or more additional pharmaceutical agent.

22. The method of claim 21 wherein the additional pharmaceutical agent is selected from the group consisting of an anti-obesity agent, an anti-diabetic agent, a lipid lowering agent, an anti-hypertensive agent, an acetylcholinesterase inhibitor, an antibody to amyloid-β, an amyloid-lowering or amyloid-inhibiting agent, an alpha-adrenergic receptor agonist, a beta-adrenergic blocking agent, an anticholinergic, an anticonvulsant, an antipsychotic, a calcium channel blocker, an O-methyltransferase inhibitor, a central nervous system stimulant, a corticosteroid, a dopamine receptor agonist or antagonist, a dopamine reuptake inhibitor, a gamma-aminobutyric receptor agonist, an immunosuppressant, an interferon, a muscarinic receptor agonist, a nicotinic receptor agonist, a norepinephrine reuptake inhibitor, a histamine 3 antagonist, a N-methyl-D-aspartate receptor antagonist, a monoamine oxidase inhibitor, a phosphodiesterase inhibitor, a serotonin 5-$HT_{1A}$ receptor antagonist, a serotonin 5-$HT_{2C}$ receptor agonist, a serotonin 5-$HT_4$ receptor agonist/antagonist, a serotonin 5-$HT_{3C}$ receptor antagonist, a serotonin 5-$HT_6$ receptor antagonist, a serotonin 5-HT reuptake inhibitor, a glycine transporter-1 inhibitor, a P450 inhibitor and an anti-tau agent.

23. The method of claim 22 wherein the additional pharmaceutical agent is an amyloid-lowering or amyloid-inhibiting agent which is selected from the group consisting of a BACE inhibitor, a gamma secretase modulator and a RAGE inhibitor.

24. The method of claim 21 in which the compound is N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

25. The method of claim 21 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide; or a tautomer thereof or a pharmaceutically acceptable salt of said compound or tautomer.

26. The method of claim 21 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide; or a tautomer thereof or a pharmaceutically acceptable salt of said compound or tautomer.

27. The method of claim 21 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide; or a tautomer thereof or a pharmaceutically acceptable salt of said compound or tautomer.

28. The method of claim 21 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide; or a tautomer thereof or a pharmaceutically acceptable salt of said compound or tautomer.

29. The method of claim 21 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; or a tautomer thereof or a pharmaceutically acceptable salt of said compound or tautomer.

30. The method of claim 21 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer.

31. A pharmaceutical composition comprising a therapeutically effective amount of a compound selected from the group consisting of
  N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;
  N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide;
  N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; and N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer;

one or more additional pharmaceutical agent; and a pharmaceutically acceptable vehicle, diluent or carrier.

32. The pharmaceutical composition of claim 31 wherein the additional pharmaceutical agent is selected from the group consisting of an anti-obesity agent, an anti-diabetic agent, a lipid lowering agent, an anti-hypertensive agent, an acetylcholinesterase inhibitor, an antibody to amyloid-β, an amyloid-lowering or amyloid-inhibiting agent, an alpha-adrenergic receptor agonist, a beta-adrenergic blocking agent, an anticholinergic, an anticonvulsant, an antipsychotic, a calcium channel blocker, an O-methyltransferase inhibitor, a central nervous system stimulant, a corticosteroid, a dopamine receptor agonist or antagonist, a dopamine reuptake inhibitor, a gamma-aminobutyric receptor agonist, an immunosuppressant, an interferon, a muscarinic receptor agonist, a nicotinic receptor agonist, a norepinephrine reuptake inhibitor, a histamine 3 antagonist, a N-methyl-D-aspartate receptor antagonist, a monoamine oxidase inhibitor, a phosphodiesterase inhibitor, a serotonin 5-HT$_{1A}$ receptor antagonist, a serotonin 5-HT$_{2C}$ receptor agonist, a serotonin 5-HT$_4$ receptor agonist/antagonist, a serotonin 5-HT$_{3C}$ receptor antagonist, a serotonin 5-HT$_6$ receptor antagonist, a serotonin 5-HT reuptake inhibitor, a glycine transporter-1 inhibitor, a P450 inhibitor and an anti-tau agent.

33. The pharmaceutical composition of claim 32 wherein the additional pharmaceutical agent is an amyloid-lowering or amyloid-inhibiting agent which is selected from the group consisting of a BACE inhibitor, a gamma secretase modulator and a RAGE inhibitor.

34. The pharmaceutical composition of claim 31 in which the compound is N-{2-[(4aR,6S,8aR)-2-Amino-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

35. The pharmaceutical composition of claim 31 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-(difluoromethoxy) pyrazine-2-carboxamide; or a tautomer thereof or a pharmaceutically acceptable salt of said compound or tautomer.

36. The pharmaceutical composition of claim 31 in which the compound is N-{2-[(4aR,6S,8aR)-2-Amino-6-methyl-4,4a,5,6-tetrahydropyrano[3,4-d][1,3]thiazin-8a(8H)-yl]-1,3-thiazol-4-yl}-5-chloropyridine-2-carboxamide; or a tautomer thereof or a pharmaceutically acceptable salt of said compound or tautomer.

37. The pharmaceutical composition of claim 31 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-fluoropyridine-2-carboxamide; or a tautomer thereof or a pharmaceutically acceptable salt of said compound or tautomer.

38. The pharmaceutical composition of claim 31 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide; or a tautomer thereof or a pharmaceutically acceptable salt of said compound or tautomer.

39. The pharmaceutical composition of claim 31 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-5-(difluoromethoxy)-3-methylpyrazine-2-carboxamide; or a tautomer thereof or a pharmaceutically acceptable salt of said compound or tautomer.

40. The pharmaceutical composition of claim 31 in which the compound is N-{2-[(4aR,6S,8aR)-2-amino-6-methyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide; or a tautomer thereof or a pharmaceutically acceptable salt of said compound or tautomer.

* * * * *